(12) United States Patent
Zhang et al.

(10) Patent No.: US 7,994,161 B2
(45) Date of Patent: Aug. 9, 2011

(54) DERIVATIVES OF 2-ALKOXY-3,4,5-TRIHYDROXY-ALKYL AMIDES, PREPARATION AND USE THEREOF, AND COMPOSITIONS CONTAINING THE SAME

(75) Inventors: Jidong Zhang, Paris (FR); Yannick Benedetti, Rosny sous Bois (FR); Alain Commerçon, Vitry-sur-Seine (FR)

(73) Assignee: Sanofi-Aventis, Paris (FR)

( * ) Notice: Subject to any disclaimer, the term of this patent is extended or adjusted under 35 U.S.C. 154(b) by 315 days.

(21) Appl. No.: 12/267,692

(22) Filed: Nov. 10, 2008

(65) Prior Publication Data

US 2009/0075971 A1    Mar. 19, 2009

Related U.S. Application Data

(63) Continuation of application No. PCT/FR2007/000868, filed on May 23, 2007.

(30) Foreign Application Priority Data

May 24, 2006    (FR) ..................................... 06 04736

(51) Int. Cl.
- C07D 243/24 (2006.01)
- C07D 243/12 (2006.01)
- C07D 267/02 (2006.01)
- A61K 31/55 (2006.01)

(52) U.S. Cl. .................. 514/211.06; 514/221; 540/491; 540/509; 540/517

(58) Field of Classification Search .................. 540/491, 540/509, 517; 514/211.06, 221
See application file for complete search history.

(56) References Cited

U.S. PATENT DOCUMENTS

| | | | |
|---|---|---|---|
| 4,477,464 A * | 10/1984 | Slade et al. ............. | 514/211.04 |
| 4,692,522 A | 9/1987 | Parsons et al. | |
| 4,831,135 A | 5/1989 | Crews et al. | |
| 5,283,241 A | 2/1994 | Bochis et al. | |
| 6,239,127 B1 | 5/2001 | Kinder, Jr. et al. | |
| 7,153,846 B2 | 12/2006 | Hoffmann et al. | |
| 2002/0128474 A1 | 9/2002 | Xu et al. | |
| 2007/0065929 A1 | 3/2007 | Hoffmann et al. | |
| 2007/0065932 A1 | 3/2007 | Hoffmann et al. | |
| 2007/0244087 A1 | 10/2007 | Zhang et al. | |
| 2007/0249584 A1 | 10/2007 | Zhang et al. | |

FOREIGN PATENT DOCUMENTS

| | | |
|---|---|---|
| EP | 0 687 673 A1 | 12/1995 |
| JP | 2004262793 | 9/2004 |
| WO | WO 98/35941 | 8/1998 |
| WO | WO 00/29382 | 5/2000 |
| WO | WO 01/85697 A1 | 11/2001 |
| WO | WO 02/39990 A2 | 5/2002 |
| WO | WO 2005/014574 A1 | 2/2005 |
| WO | WO 2005/044803 | 5/2005 |
| WO | WO 2006/056696 A2 | 6/2006 |

OTHER PUBLICATIONS

U.S. Appl. No. 12/267,689, filed Nov. 10, 2008, Zhang et al.
U.S. Appl. No. 12/267,691, filed Nov. 10, 2008, Zhang et al.
Adamczeski et al, Novel Sponge-Derived Amino Acids. 5. Structures, Stereochemistry, and Synthesis of Several New Heterocycles, J. Am. Chem. Soc. 1989, 111, pp. 647-654.
Chang et al, Synthesis of optically active alpha-aminobenzolactam via an oxidative-cyclization reaction, Tetrahedron: Asymmetry 14 (2003) pp. 2081-2085.
Groweiss, et al., Cytotoxic Metabolites from an Australian Collection of the Sponge, J. Nat. Prod.; 1999; 62; pp. 1691-1693.
Kinder et al, Synthesis and Antitumor Activity of Ester-Modified Analogues of Bengamide B, J. Med. Chem. 2001, 44, pp. 3692-3699.
Morton et al, Novel Solid-Phase Sythesis of 1,5-benzothiazepine-4-one Derivatives, Tetrahedron Letters 41 (2000) pp. 3029-3033.
Parsons et al, Cholecystokinin Antagonists. Synthesis and Biological Evaluation of a 3-Substituted Benzolactams, J. Med. Chem. 1989, 32, pp. 1681-1685.
Quinoa et al, Bengamides, Heterocyclic Anthelminthics from a Jaspidae Marine Sponge, J. Org. Chem. (1986) 51, pp. 4494-4497.
Ramana et al, A Carbohydrate-Based Approach for the Total Synthesis of 1,3-Polyol/alpha-Pyrone Antifungal Natural Products, J. Org. Chem. 2005, 70, pp. 8216-8219.
Slade et al, Angiotensin Converting Enzyme Inhibitors: 1,5-Benzothiazepine Derivatives, J. Med. Chem., 1985, 28, pp. 1517-1521.
Thale et al, Bengamides Revisited: New Structures and Antitumor Studies, J. Org. Chem. 2001, 66, pp. 1733-1741.

* cited by examiner

*Primary Examiner* — Bruck Kifle
(74) *Attorney, Agent, or Firm* — Scully, Scott, Murphy & Presser, P.C.

(57) ABSTRACT

The present invention relates to 2-alkoxy-3,4,5-trihydroxy-alkylamide derivatives, to pharmaceutical compositions comprising such compounds, to methods of treatment comprising administering such compounds, to processes for the preparation of such compounds, and to intermediate precursors to such compounds.

31 Claims, No Drawings

DERIVATIVES OF 2-ALKOXY-3,4,5-TRIHYDROXY-ALKYL AMIDES, PREPARATION AND USE THEREOF, AND COMPOSITIONS CONTAINING THE SAME

The present invention relates in particular to 2-alkoxy-3,4,5-trihydroxy-alkylamide derivatives, their preparation, compositions containing them and their use as medicament.

More particularly, according to a first aspect, the invention relates to 2-alkoxy-3,4,5-trihydroxy-alkylamide derivatives which are useful as anticancer agents.

2-Methoxy-3,4,5-trihydroxy-alkylamides have been described in U.S. Pat. No. 6,239,127, US 20010044433 A1, WO 01/85697, WO 00/29382, U.S. Pat. No. 4,831,135, EP 687673, and US 20020128474 A1. These documents disclose mainly analogues and derivatives of bengamide, a natural product isolated from a marine sponge, Jaspis coriacea.

These same products have been described in the literature: J. Org. Chem. (1986), 51(23), 4494-7; J. Org. Chem. (2001), 66(5), 1733-41; J. Med. Chem. 2001, 44, 3692-9.

The problem which the present invention proposes to solve is to obtain novel products having anticancer activity. In addition to maintaining an anticancer activity, some of these novel products may also have advantageous properties with respect to their pharmacological activity, such as their pharmacokinetics, bioavailability, solubility, stability, toxicity, absorption or metabolism.

The subject of the present invention is products corresponding to the following general formula (I):

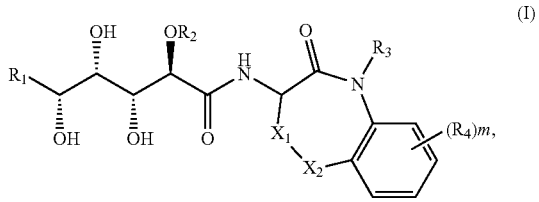

in which:
a) $R_1$ is independently chosen from the group consisting of (C1-C12)alkyl, (C2-C12)alkenyl, (C2-C12)alkynyl, cycloalkyl, heterocyclyl, aryl, heteroaryl, cycloalkyl(C1-C12)alkyl, cycloalkyl(C2-C12)alkenyl, cycloalkyl(C2-C12)alkynyl, heterocyclyl(C1-C12)alkyl, heterocyclyl(C2-C12)alkenyl, heterocyclyl(C2-C12)alkynyl, aryl(C1-C12)alkyl, aryl(C2-C12)alkenyl, aryl(C2-C12)alkynyl, heteroaryl(C1-C12)alkyl, heteroaryl(C2-C12)alkenyl, heteroaryl(C2-C12)alkynyl, the aryl group of each $R_1$ being optionally substituted with one or more halogens;
b) $R_2$ is chosen from the group consisting of (C1-C6)alkyl, aryl(C1-C6)alkyl, heteroaryl(C1-C6)alkyl, aryl, heteroaryl, (C1-C6)alkylthio(C1-C6)alkyl, di(C1-C6)alkylamino(C1-C6)alkyl, aryloxy(C1-C6)alkyl, (C1-C6)alkoxy(C1-C6)alkyl;
c) $R_3$ is chosen from the group consisting of H, COO($R_5$), CONH($R_5$), CO($R_5$), O($R_5$), $R_5$;
d) $R_4$ is independently chosen from the group consisting of H, F, Cl, Br, $N(R_5)_2$, $NO_2$, CN, COO($R_5$), $CON(R_5)_2$, NHCO($R_5$), NHCOO($R_5$), OCONH($R_5$), O($R_5$), $R_5$ or alternatively two substituents $R_4$ linked to 2 adjacent carbons of the phenyl form together a ring chosen from cycloalkyl, heterocyclyl, aryl or heteroaryl, optionally substituted with one or more $R_4$;
e) $X_1$ is —$CH_2$— and $X_2$ is independently chosen from the group consisting of O, N($R_5$), or alternatively, $X_1$ and $X_2$ form together a divalent group independently chosen from —N=C($R_5$)—, —N($R_5$)—C($R_5$)($R_5$)—, it being possible for the two substituents $R_5$ to be identical or different;
f) m has the value 0, 1, 2, 3, or 4;
g) $R_5$ is independently chosen from non-bonding electron doublet, H, (C1-C12)alkyl, (C2-C12)alkenyl, (C2-C12)alkynyl, halo(C1-C12)alkyl, aryl(C1-C12)alkyl, heteroaryl(C1-C12)alkyl, heteroarylaryl(C1-C12)alkyl, aryl, heteroaryl, cycloalkyl, in which each $R_5$ is optionally substituted with at least one substituent chosen from OH, halogen, (C1-C4)alkyl, (C1-C4)alkoxy, aryl(C1-C4)alkyl, aryl, heteroaryl(C1-C4)alkyl, heteroaryl, —$N(CH_3)_2$, —$NH_2$, $CONH_2$,

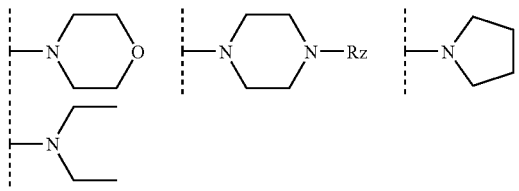

each of the Rz is independently chosen from the group consisting of H, COO($R_5$), CONH($R_5$), CON($R_5)_2$, CO($R_5$), $R_5$, in which each $R_5$ is independently chosen from (C1-C4)alkyl, halo(C1-C4)alkyl, aryl(C1-C4)alkyl, heteroaryl(C1-C4)alkyl, in which each $R_5$ is optionally substituted with one substituent chosen from OH, halogen, (C1-C4)alkyl, (C1-C4)alkoxy, aryl(C1-C4)alkyl, aryl, heteroaryl(C1-C4)alkyl, heteroaryl.

The subject of the present invention is the products of general formula (I) above, in which $R_1$ is independently chosen from the group consisting of (C1-C12)alkyl, (C2-C12)alkenyl, (C2-C12)alkynyl, cycloalkyl, heterocyclyl, aryl, heteroaryl, aryl(C1-C12)alkyl, aryl(C2-C12)alkenyl, aryl(C2-C12)alkynyl, heteroaryl(C1-C12)alkyl, heteroaryl(C2-C12)alkenyl, heteroaryl(C2-C12)alkynyl.

The subject of the present invention is the products of general formula (I) above, in which $R_2$ is chosen from the group consisting of (C1-C6)alkyl, aryl(C1-C6)alkyl, heteroaryl(C1-C6)alkyl, aryl, heteroaryl, (C2-C12)alkenylaryl, (C2-C12)alkenylheteroaryl, (C1-C6)alkylthio(C1-C6)alkyl, di(C1-C6)alkylamino(C1-C6)alkyl, aryloxy(C1-C6)alkyl.

According to the invention, $R_1$ is preferably chosen from —C($R_6$)=C($R_7$)($R_8$) in which $R_6$, $R_7$ and $R_8$ are independently chosen from H, (C1-C6)alkyl, cycloalkyl, heterocyclyl, aryl, heteroaryl.

More preferably, $R_1$ is chosen from (E) —CH=CH—CH($CH_3$)($C_2H_5$), (E) —CH—CH=CH—CH($CH_3)_2$, (E) —CH—CH=CH—C($CH_3)_3$ or alternatively from (E) —C($CH_3$)=CH—CH($CH_3$)($C_2H_5$), (E) —C($CH_3$)=CH—CH($CH_3)_2$ and (E) —C($CH_3$)=CH—C($CH_3)_3$. More preferably, $R_1$ is chosen from (E) —CH—CH=CH—$C_5H_9$, (E) —CH—CH=CH-thiophene, (E) —CH=CH—$C_6H_5$ where the phenyl is optionally substituted with a bromine atom.

According to the invention, $R_2$ is preferably methyl.

Among the subjects of the present invention, a first group is characterized in that $R_3$ is H. A second group is characterized in that $R_3$ is methyl. A third group is characterized in that $R_3$ is (C1-C6)alkyl, (C1-C6)alkenyl, benzyl or (3,5-difluoro)benzyl.

Among these subjects, another subgroup is characterized in that $X_1$ —$CH_2$— and $X_2$ is O or N($R_5$) in which $R_5$ is H, benzyl or methyl, or $X_1$ and $X_2$ form together a divalent group —N=C($R_5$)— where $R_5$ is phenyl.

Among these subjects, another subgroup is characterized in that m has the value 0 or alternatively $R_4$ is phenyl.

Preferably, the invention relates to the products exemplified in Table 1.

According to another aspect, the invention relates to the methods of preparing the products of general formula (I) or (I'). The products of general formula (I') are optionally active precursors of the products of general formula (I). The products of general formula (I) are obtained from the products of general formula (I') by methods described or by one or more reactions which are classic for persons skilled in the art such as for example a cyclopropanation, an oxidation or a chiral separation.

The products of general formula (I) or (I') may be obtained by hydrolysis of a product of general formula (II):

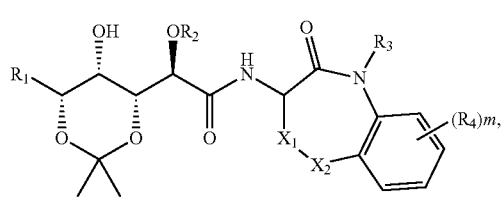

(II)

in which $R_1$, $R_2$, $R_3$, $R_4$, $X_1$, $X_2$ and m are as defined above.

The products of general formula (II) may be obtained by the reaction of a product of general formula (III):

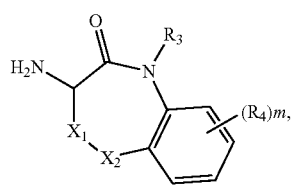

(III)

in which $R_3$, $R_4$, $X_1$, $X_2$ and m are as defined above, with a product of general formula (IV):

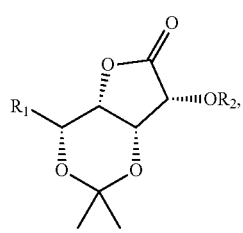

(IV)

in which $R_1$ and $R_2$ are as defined above.

The products of general formula (I) or (I') may also be obtained by the reaction of a product of general formula (III) as defined above, with a product of general formula (V):

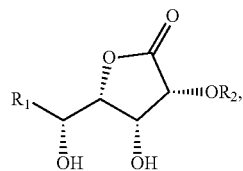

(V)

in which $R_1$ and $R_2$ are as defined above.

The products of general formula (V) may be obtained by hydrolysis of a product of general formula (IV):

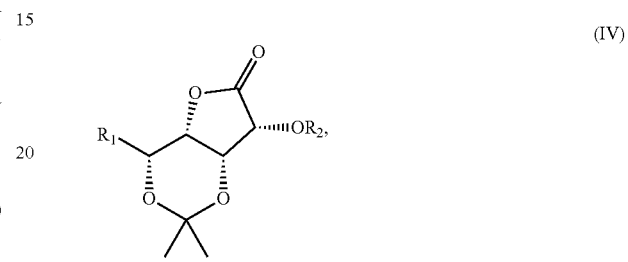

(IV)

in which $R_1$ and $R_2$ are as defined above. Products of general formula (V) for which $R_1$ represents —CH=CH—$R'_1$ may also be obtained by hydrolysis of a product of general formula (VII):

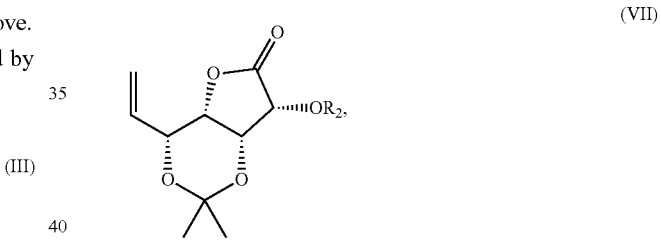

(VII)

in which $R_2$ is as defined above, in order to obtain a product of general formula (VI):

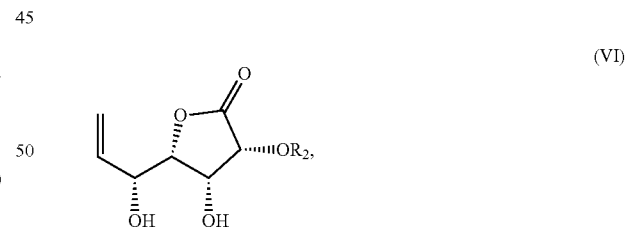

(VI)

in which $R_2$ is as defined above, which undergoes metathesis in order to obtain a product of general formula (V):

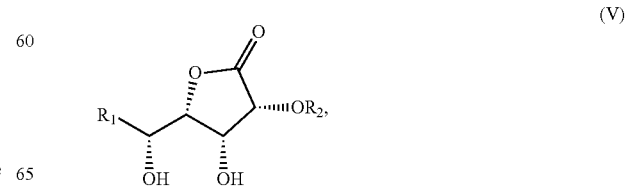

(V)

for which R₁ represents —CH═CH—R'₁ and R'₁ represents a (C1-C6)alkyl, cycloalkyl, heterocyclyl, aryl or heteroaryl group.

The products of general formula (VII) may be obtained by double dehydration of a product of general formula (VIII):

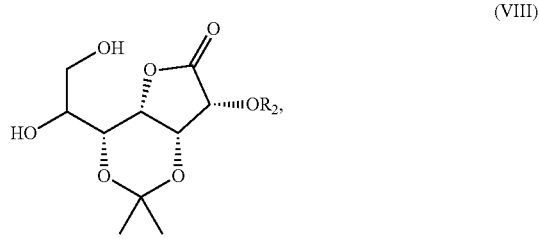

(VIII)

in which R₂ is as defined above.

The products of general formula (I'), (II) and (III) as defined above are a subject of the present invention.

The products of general formula (IV) and (V) as defined above for which R₂ is methyl or ethyl and R1 is -(E) —CH═CH—C₅H₉, -(E) —CH═CH-thiophene or -(E) —CH═CH—C₆H₅ where the phenyl is substituted with a bromine atom, are a subject of the present invention.

The products of general formula (VI) for which R₂ is methyl or ethyl are a subject of the present invention. The products of general formula (VII) for which R₂ is methyl or ethyl are a subject of the present invention.

The products according to the present invention may exist in the form of bases, addition salts with acids, solvates, hydrates or prodrugs.

The products according to the invention may be in non—CHiral or racemic form, or a form enriched with a stereoisomer, or enriched with an enantiomer; and may be optionally salified. The products for which the carbon linked to the exocyclic amine is of (S) configuration are preferred.

A product in accordance with the invention can be used for the manufacture of a medicament useful for preventing or treating a pathological condition, in particular a cancer.

The products of the present invention may also be used for the manufacture of a medicament useful for preventing or treating a pathological condition in which neovascularization or angiogenesis occurs inappropriately, that is to say in cancers in general and in specific cancers such as Kaposi's sarcoma or infantile haemangioma, but also in rheumatoid arthritis, osteoarthritis and/or associated pain, inflammatory bowel diseases such as haemorrhagic rectocolitis or Crohn's disease, eye diseases such as age-related macular degeneration, diabetic retinopathies, chronic inflammation and psoriasis.

Angiogenesis is a process of generation of new capillary vessels from pre-existing vessels. Tumour angiogenesis (formation of blood new vessels), essential for tumour growth, is also one of the main factors in metastatic dissemination (Oncogene. 2003 May 19; 22(20):3172-9; Nat. Med. 1995 January; 1(1):27-31.).

The present invention also relates to therapeutic compositions containing a compound according to the invention, in combination with a pharmaceutically acceptable excipient according to the mode of administration chosen. The pharmaceutical composition may be provided in solid, liquid or liposome form.

Among the solid compositions, there may be mentioned powders, gelatin capsules and tablets. Among the oral forms, it is also possible to include the solid forms which are protected against the acid medium of the stomach. The carriers used for the solid forms consist in particular of inorganic carriers such as phosphates or carbonates, or organic carriers such as lactose, celluloses, starch or polymers. The liquid forms consist of solutions, suspensions or dispersions. They contain, as dispersive carrier, either water, an organic solvent (ethanol, NMP or the like) or mixtures of surfactants and solvents or of complexing agents and solvents.

The liquid forms will be preferably injectable and as a result will have a formulation which is acceptable for such a use.

Acceptable routes of administration by injection include the intravenous, intraperitoneal, intramuscular and subcutaneous routes, the intravenous route being preferred.

The administered dose of the compounds of the invention will be adjusted by the practitioner according to the route of administration, the patient and the condition of the latter.

The compounds of the present invention may be administered alone or as a mixture with other anticancer agents. Among the possible combinations, there may be mentioned:

alkylating agents, and in particular cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine platinum derivatives such as in particular cisplatin, carboplatin or oxaliplatin antibiotic agents such as in particular bleomycin, mitomycin, dactinomycin antimicrotubule agents such as in particular vinblastine, vincristine, vindesine, vinorelbine, taxoids (paclitaxel and docetaxel)

anthracyclines such as in particular doxorubicin, daunorubicin, idarubicin, epirubicin, mitoxantrone, losoxantrone groups I and II topoisomerases such as etoposide, teniposide, amsacrine, irinotecan, topotecan and tomudex fluoropyrimidines such as 5-fluorouracil, UFT, floxuridine cytidine analogues such as 5-azacytidine, cytarabine, gemcitabine, 6-mercaptopurine, 6-thioguanine adenosine analogues such as pentostatin, cytarabine or fludarabine phosphate methotrexate and folinic acid various enzymes and compounds such as L-asparaginase, hydroxyurea, trans-retinoic acid, suramin, dexrazoxane, amifostine, herceptin as well as oestrogenic and androgenic hormones antivascular agents such as combretastatin derivatives, for example CA4P, chalcones or colchicine, for example ZD6126, and their prodrugs kinase inhibitors such as ertonilib or imatinib biotherapeutic agents such as antibodies such as rituximab, bevacizumab, cetuximab, trastuzumab or alemtuzumab proteasome inhibitors such as bortezomib.

It is also possible to combine the compounds of the present invention with a radiation treatment. These treatments may be administered simultaneously, separately or sequentially. The treatment will be adapted by the practitioner according to the disease to be treated.

DEFINITIONS

The term "halogen" refers to an element chosen from F, Cl, Br and I.

The term "alkyl" refers to a linear or branched, saturated hydrocarbon substituent having from 1 to 12 carbon atoms. The methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl substituents are examples of an alkyl substituent.

The term "alkenyl" refers to a linear or branched hydrocarbon substituent having one or more unsaturations, having from 2 to 12 carbon atoms. The ethylenyl, 1-methylethylenyl, prop-1-enyl, prop-2-enyl, Z-1-methylprop-1-enyl, E-1-methylprop-1-enyl, Z-1,2-dimethyl-prop-1-enyl, E-1,2-dimethylprop-1-enyl, but-1,3-dienyl, 1-methylidenyl-prop-2-enyl, Z-2-methyl but-1,3-dienyl, E-2-methyl but-1,3-dienyl, 2-methyl-1-methylidenylprop-2-enyl, undec-1-enyl and undec-10-enyl substituents are examples of an alkylene substituent.

The term "alkynyl" refers to a linear or branched hydrocarbon substituent having at least two unsaturations carried by a pair of vicinal carbon atoms, having from 2 to 12 carbon atoms. The ethynyl; prop-1-ynyl; prop-2-ynyl; and but-1-ynyl substituents are examples of an alkynyl substituent.

The term "aryl" refers to a mono- or polycyclic aromatic substituent having from 6 to 14 carbon atoms. The phenyl, naphth-1-yl; naphth-2-yl; anthracen-9-yl; 1,2,3,4-tetrahydronaphth-5-yl; and 1,2,3,4-tetrahydronaphth-6-yl substituents are examples of an aryl substituent.

The term "heteroaryl" refers to a mono- or polycyclic heteroaromatic substituent having from 1 to 13 carbon atoms and from 1 to 4 heteroatoms. The pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinoleyl; isoquinoleyl; carbazolyl; and acridyl substituents are examples of a heteroaryl substituent.

The term "heteroatom" refers here to an at least divalent atom, different from carbon, N; O; S; and Se are examples of a heteroatom.

The term "cycloalkyl" refers to a saturated or partially unsaturated cyclic hydrocarbon substituent having from 3 to 12 carbon atoms. The cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronaphthyl substituents are examples of a cycloalkyl substituent.

The term "heterocyclyl" refers to a saturated or partially unsaturated cyclic hydrocarbon substituent having from 1 to 13 carbon atoms and from 1 to 4 heteroatoms. Preferably, the saturated or partially unsaturated cyclic hydrocarbon substituent will be monocyclic and will comprise 4 or 5 carbon atoms and 1 to 3 heteroatoms.

As regards the fused phenyl, when m has the value zero, it is understood that this is a phenyl which is unsubstituted (or substituted with 4 hydrogen atoms), and when m has the value 1, 2, 3 or 4, it is understood that 1, 2, 3 or 4 hydrogen atoms are replaced by a substituent $R_4$.

The advantages of the invention will be more particularly illustrated by the following examples:

Abbreviations:

Ac acetate; Bn benzyl; ° C. degrees Celsius; cat. catalyst; TLC thin-layer chromatography; PCC preparative column chromatography; cm centimeter; δ chemical shift; d doublet; dd doublet of doublets; DMF dimethylformamide; DMSO-$d^6$ deuterated dimethylsulphoxide; dt doublet of triplets; eq. equivalent; ES+/−electrospray (positive/negative modes); Et ethyl; g gram; h hour; Hz hertz; $IC_{50}$ constant for 50% inhibition of activity; iPr isopropyl; d. day; J coupling constant; LCMS liquid chromatography coupled with mass spectrometry; m multiplet; Me methyl; mg milligram; MHz megahertz; mL milliliter; μL microliter; mm millimeter; μm micrometer; mmol millimole; mn minute; N mol·$L^{-1}$; m.p. melting point; Ph phenyl; ppm parts per million; q quadruplet; Y yield; Rf retardation factor; $^1H$ NMR proton nuclear magnetic resonance; s singlet; bs broad singlet; t triplet; RT room temperature; tBu tert-butyl; TFA trifluoroacetic acid; THF tetrahydrofuran; $t_R$ retention time; U.V. ultraviolet; V volt.

Ex1: N-((S)-8-oxo-6,7,8,9-tetrahydro-5-oxa-9-aza-benzocyclohepten-7-yl)-(E)-(2R,3R,4S,5R)-3,4,5-trihydroxy-2-methoxy-8,8-dimethylnon-6-enamide Ex1

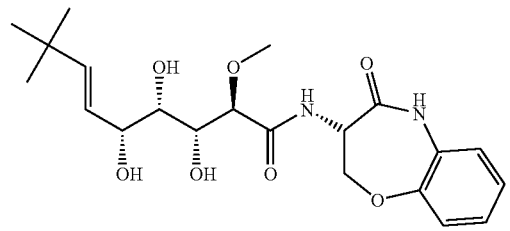

Step 1: Preparation of (3R,4R,5S)-4-hydroxy-5-((E)-(R)-1-hydroxy-4,4-dimethylpent-2-enyl)-3-methoxy-dihydrofuran-2-one (2)

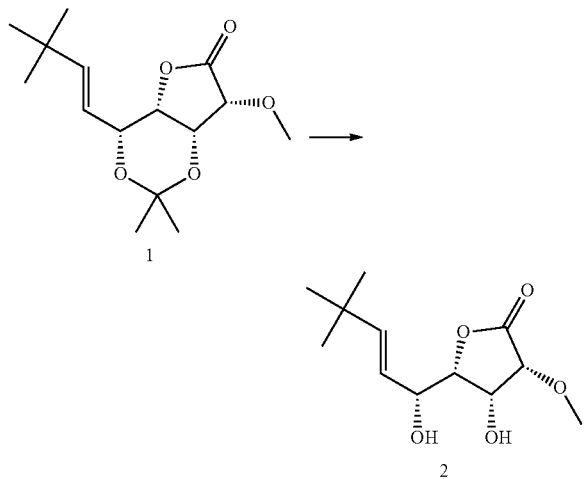

To a 250 mL round-bottomed flask containing 40 mL of water and 3.6 g of 1 (which may be prepared according to the procedures described in Org. Process Res. Dev. 2003, 7(6), 856-865) in suspension are added 17 mL of TFA in solution in 10 mL of water. The medium is stirred for 1.5 h at RT and then the medium is diluted with 290 mL of water, frozen and freeze-dried. 4 g of an oil are obtained, which oil crystallizes in 20 mL of isopropyl ether at RT. After draining, washing with isopropyl ether and drying under vacuum at 40° C., 2.46 g of expected product 2 (white crystals) are obtained.

m.p.: 123° C.

CI: m/z=262 $MNH_4^+$.

$^1$H NMR (400 MHz, DMSO-d$_6$), δ(ppm): 1.00 (s, 9H); 3.41 (s, 3H); 3.93 (dd, J=2.5 and 9.0 Hz, 1H); from 4.22 to 4.31 (m, 3H); 5.19 (d, J=5.0 Hz, 1H); 5.42 (dd, J=5.0 and 16.0 Hz, 1H); 5.43 (d, J=4.5 Hz, 1H); 5.87 (d, J=16.0 Hz, 1H).

IR (KBr): 3239; 2964; 2914; 1701; 1499; 1312; 1253; 1047 & 751 cm$^{-1}$.

Step 2: Preparation of (S)-7-amino-6,7-dihydro-9H-5-oxa-9-azabenzocyclohepten-8-one hydrochloride (4)

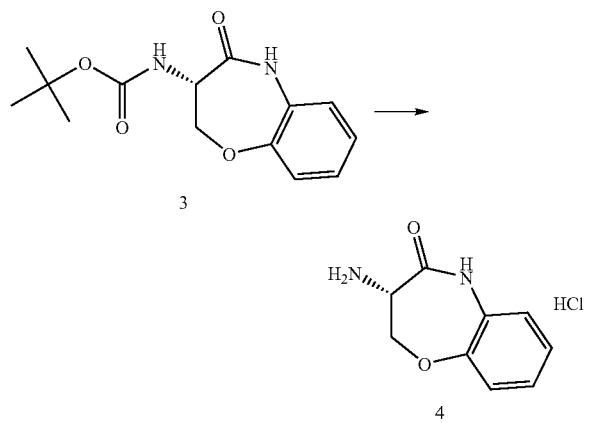

To a 25 mL round-bottomed flask containing 400 mg of 3 (1.44 mmol) (which may be prepared according to the procedures described in Chem. Pharm. Bull. 1986, 34(3), 1128-1147) are added 11 mL of a solution of hydrochloric acid in dioxane (4M). The mixture is stirred for 6 h at RT under argon. A white precipitate is formed, which precipitate is drained, washed with dioxane and then with isopropyl ether. 288 mg of amine 4 are thus obtained in the hydrochloride form.

EI: m/z=178 M$^+$.

[α]$_D$: −239.1+/−2.5 (c=5.160 mg/0.5 mL MeOH)

$^1$H NMR (400 MHz, DMSO-d$_6$), δ(ppm): 4.32 (dd, J=5.5 and 10.0 Hz, 1H); 4.40 (t, J=10.0 Hz, 1H); 4.59 (dd, J=5.5 and 10.0 Hz, 1H); 7.14 (m, 4H); 8.55 (broad s, 3H); 10.5 (s, 1H).

IR (KBr): 3239; 2964; 2914; 1701; 1499; 1312; 1253; 1047 & 751 cm$^{-1}$.

Step 3: Preparation of N-((S)-8-oxo-6,7,8,9-tetrahydro-5-oxa-9-azabenzocyclohepten-7-yl)-(E)-(2R,3R,4S,5R)-3,4,5-trihydroxy-2-methoxy-8,8-dimethyl-non-6-enamide (Ex1)

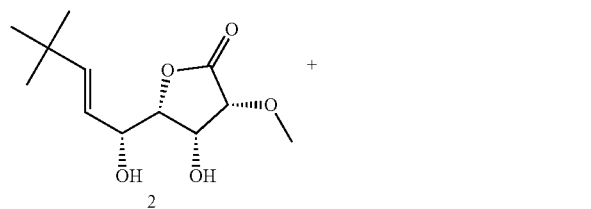

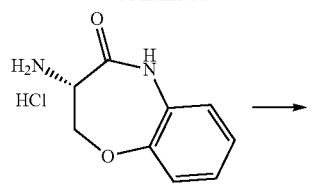

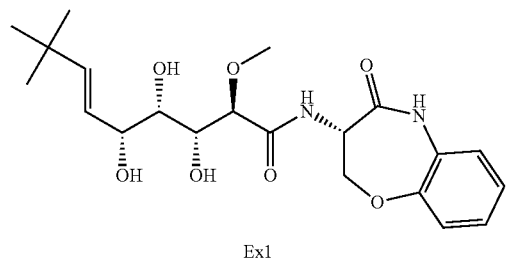

There are successively introduced into a 10 mL round-bottomed flask, with stirring and under an argon atmosphere, 57 mg of 2 (187 μmol), 80 mg of 4 (373 μmol), 140 mg of sodium 2-ethylhexanoate (0.84 mmol) in 1.8 mL of THF. The stirring is maintained at RT for 24 h. 30 mL of ethyl acetate are added to the reaction medium. The mixture is successively washed with 20 mL of an HCl solution (0.1N), and then 20 mL of a saturated aqueous NaCl solution. The organic phase is dried over anhydrous magnesium sulphate, filtered and then evaporated to dryness. 340 mg of a brown solid are obtained, which solid is chromatographed on a silica cartridge (25 g, eluent CH$_2$Cl$_2$/MeOH— in a 5 to 20% MeOH gradient). 24 mg of expected product Ex1 are obtained.

ES: m/z=421 (M−H)$^-$.

[α]$_D$: −64+/−2.7 (c=0.556 mg/0.5 mL MeOH)

$^1$H NMR (400 MHz, DMSO-d$_6$), δ(ppm): 0.96 (s, 9H); 3.24 (s, 3H); from 3.25 to 3.32 (m partially masked, 1H); 3.52 (m, 1H); 3.71 (d, J=8.0 Hz, 1H); 3.94 (m, 1H); from 4.28 to 4.39 (m, 4H); 4.55 (d, J=4.5 Hz, 1H); 4.68 (m, 1H); 5.30 (dd, J=7.0 and 16.0 Hz, 1H); 5.63 (d, J=16.0 Hz, 1H); from 7.07 to 7.16 (m, 4H); 8.14 (d, J=8.0 Hz, 1H); 10.05 (s, 1H).

IR (KBr): 3420; 2958; 1667; 1499; 1419; 1364; 1111; 978 & 757 cm$^{-1}$

Ex2: N-((S)-9-methyl-8-oxo-6,7,8,9-tetrahydro-5-oxa-9-azabenzocyclohepten-7-yl)-(E)-(2R,3R,4S,5R)-3,4,5-trihydroxy-2-methoxy-8,8-dimethylnon-6-enamide

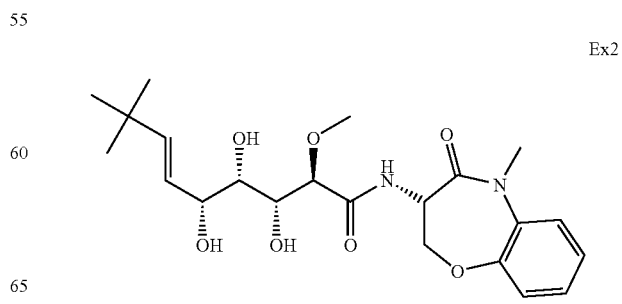

Step 1: Preparation of tert-butyl ((S)-9-methyl-8-oxo-6,7,8,9-tetrahydro-5-oxa-9-azabenzocyclohepten-7-yl)carbamate (5)

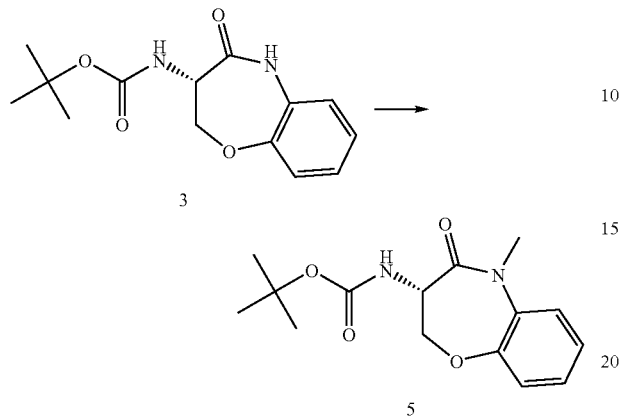

A solution of 500 mg of 3 (1.8 mmol) in 3 mL of DMF is introduced dropwise into a 10 mL round-bottomed flask, with stirring and under an argon atmosphere, containing 1 mL of DMF and 72 mg of sodium hydride in suspension at 60% in oil (1.8 mmol). The medium is stirred for 1 h, and then 258 mg (1.82 mmol) of methyl iodide are added. The medium is kept stirring overnight and then 10 mL of water are added. A precipitate forms, which precipitate is drained, washed with water and dried under vacuum. 452 mg of expected product 5 (white solid, m.p.: 152.4° C.) are obtained.

ES: m/z=293 MH$^+$.

$^1$H NMR (400 MHz, DMSO-d$_6$), δ(ppm): 1.34 (s, 9H); 3.28 (s, 3H); from 4.25 to 4.40 (m, 3H); 7.13 (d, J=8.0 Hz, 1H); 7.18 (dd, J=2.0 and 7.5 Hz, 1H); from 7.22 to 7.33 (m, 2H); 7.46 (dd, J=2.0 and 7.5 Hz, 1H)

IR (KBr): 3354; 2976; 1709; 1673; 1533; 1500; 1368; 1254; 1173; 998 & 771 cm$^{-1}$

Step 2: Preparation of 7-(S)-amino-9-methyl-6,7-dihydro-9H-5-oxa-9-azabenzocyclohepten-8-one hydrochloride (6)

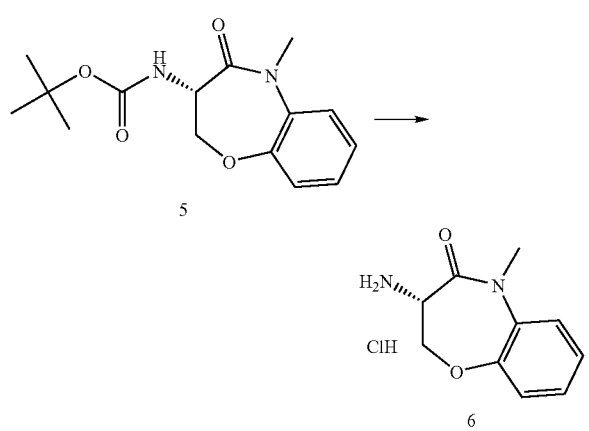

0.45 g of 5 (1.54 mmol) is taken up in a 50 mL round-bottomed flask and 11 mL of a hydrochloric acid solution in dioxane (4M) are added. The medium is stirred overnight at RT under argon. After evaporation of the solvent, the residue is taken up in 30 mL of isopropyl ether. The solid formed is drained and dried under vacuum. 260 mg of expected product 6 (ecru-coloured solid) are thus recovered.

EI: m/z=192 M$^+$.

[α]$_D$: −257.5+/−2.72 (c=5.842 mg/0.5 mL MeOH)

$^1$H NMR (400 MHz, DMSO-d$_6$), δ(ppm): 3.35 (s, 3H); 4.25 (dd, J=7.5 and 10.5 Hz, 1H); 4.43 (t, J=10.5 Hz, 1H); 4.57 (dd, J=7.5 and 10.5 Hz, 1H); from 7.24 to 7.38 (m, 3H); 7.52 (broad d, J=7.5 Hz, 1H); 8.43 (broad s, 3H).

IR (KBr): 2985; 1684; 1500; 1478; 1374; 1272; 1246; 1052; 805; 776 & 754 cm$^{-1}$

Step 3: Preparation of N-((S)-9-methyl-8-oxo-6,7,8,9-tetrahydro-5-oxa-9-azabenzocyclohepten-7-yl)-(E)-(2R,3R,4S,5R)-3,4,5-trihydroxy-2-methoxy-8,8-dimethylnon-6-enamide (Ex2)

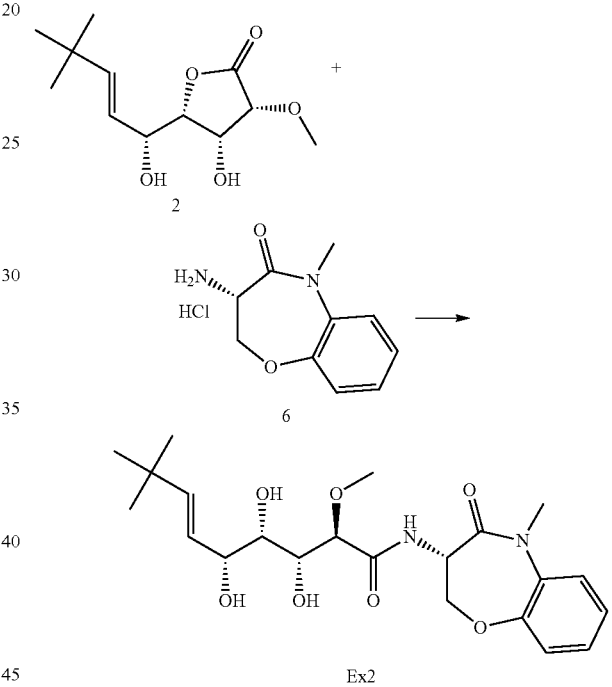

There are successively introduced into a 10 mL round-bottomed flask, with stirring and under an argon atmosphere, 55 mg of 2 (225 μmol), 103 mg of 6 (450 μmol), 168 mg of sodium 2-ethylhexanoate (1.01 mmol) in 2.5 mL of THF. The stirring is maintained at RT for 48 h. 30 mL of ethyl acetate are added to the reaction medium. The mixture is washed with 20 mL of a saturated aqueous NaCl solution. The organic phase is dried over anhydrous magnesium sulphate, filtered and then evaporated to dryness. 174 mg of crude product are obtained, which product is chromatographed on a silica cartridge (12 g, eluent CH$_2$Cl$_2$/MeOH 90/10). 37 mg of expected product Ex2 are recovered.

ES: m/z=435 (M−H)$^-$.

[α]$_D$: −94+/−1.7 (c=1.611 mg/0.5 mL MeOH)

$^1$H NMR (400 MHz, DMSO-d$_6$), δ(ppm): 0.96 (s, 9H); 3.21 (s, 3H); from 3.24 to 3.32 (m masked, 1H); 3.30 (s, 3H); 3.49 (m, 1H); 3.69 (d, J=8.0 Hz, 1H); 3.92 (m, 1H); from 4.28 to 4.37 (m, 4H); 4.54 (broad d, J=4.5 Hz, 1H); 4.71 (m, 1H); 5.29 (dd, J=7.0 and 16.0 Hz, 1H); 5.62 (d, J=16.0 Hz, 1H); 7.21 (dd, J=2.0 and 7.5 Hz, 1H); from 7.24 to 7.34 (m, 2H); 7.48 (dd, J=2.0 and 7.5 Hz, 1H); 8.15 (d, J=8.0 Hz, 1H).

Ex3: N-((S)-2-oxo-2,3,4,5-tetrahydro-1H-1,5-benzo-diazepin-3-yl)-(E)-(2R,3R,4S,5R)-3,4,5-trihydroxy-2-methoxy-8,8-dimethylnon-6-enamide

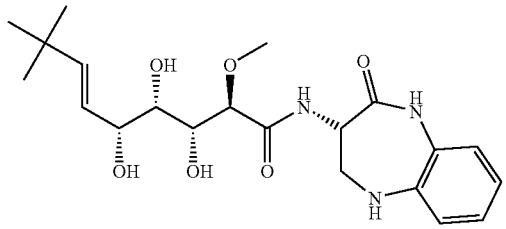

Step 1: Preparation of 3-(S)-amino-1,3,4,5-tetrahydro-1,5-benzodiazepin-2-one hydrochloride (8)

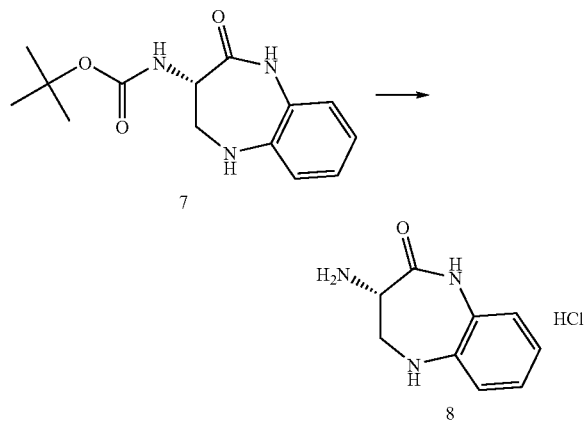

To a 25 mL round-bottomed flask containing 300 mg of 7 (1.08 mmol) (which may be prepared according to the procedures described in Bioorg. Med. Chem. Lett. 2002, 12, 1225-1227) are added 5 mL of a solution of hydrochloric acid in dioxane (4M). The medium is stirred for 6 h at RT under argon. A white precipitate forms, which precipitate is drained, washed with CH$_2$Cl$_2$ and dried under vacuum. 221 mg of amine 8 are thus obtained in hydrochloride form.

ES: m/z=178 MH$^+$.

[α]$_D$: −101.1+/−1.5 (c=2.422 mg/0.5 mL MeOH)

Step 2: Preparation of N-((S)-2-oxo-2,3,4,5-tetrahydro-1H-1,5-benzodiazepin-3-yl)-(E)-(2R,3R,4S,5R)-3,4,5-trihydroxy-2-methoxy-8,8-dimethylnon-6-enamide (Ex3)

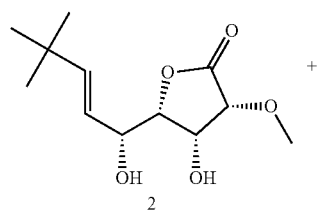

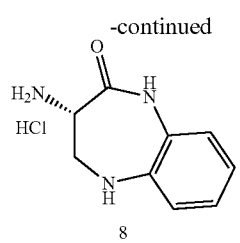

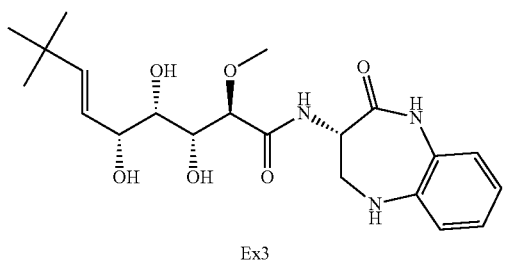

82 mg of 2 (336 μmol), 101 mg of 8 (403 μmol), 251 mg of sodium 2-ethylhexanoate (1.51 mmol) in 1.2 mL of THF are successively introduced into a 10 mL round-bottomed flask, with stirring and under an argon atmosphere. The stirring is maintained at RT for 24 h. 30 mL of ethyl acetate are added to the reaction medium. The mixture is washed with 20 mL of a solution of water saturated with NaCl. The organic phase is dried over anhydrous magnesium sulphate, filtered and then evaporated to dryness. 248 mg of a brown solid are obtained, which solid is chromatographed on a silica cartridge (25 g, eluent CH$_2$Cl$_2$/MeOH— as a 5 to 20% MeOH gradient). 36 mg of expected product Ex3 are recovered.

ES: m/z=422 MH$^+$; m/z=404 MH$^+$—H$_2$O.

[α]$_D$: +6.0+/−0.7 (c=1.512 mg/0.5 mL MeOH)

$^1$H NMR (400 MHz, DMSO-d$_6$), δ(ppm): 0.97 (s, 9H); 3.25 (s, 3H); from 3.25 to 3.36 (m masked, 2H); from 3.51 to 3.61 (m, 2H); 3.72 (d, J=7.5 Hz, 1H); 3.95 (m, 1H); 4.33 (d, J=6.5 Hz, 1H); 4.39 (d, J=7.0 Hz, 1H); 4.46 (m, 1H); 4.54 (d, J=4.5 Hz, 1H); 5.32 (dd, J=7.0 and 16.0 Hz, 1H); 5.64 (d, J=16.0 Hz, 1H); 5.78 (d, J=6.5 Hz, 1H); 6.69 (dt, J=2.0 and 7.5 Hz, 1H); 6.72 (broad d, J=7.5 Hz, 1H); from 6.87 to 6.94 (m, 2H); 7.92 (d, J=7.5 Hz, 1H); 9.82 (s, 1H).

Ex4: N-((S)-1-methyl-2-oxo-2,3,4,5-tetrahydro-1H-1,5-benzodiazepin-3-yl)-(E)-(2R,3R,4S,5R)-3,4,5-trihydroxy-2-methoxy-8,8-dimethylnon-6-enamide

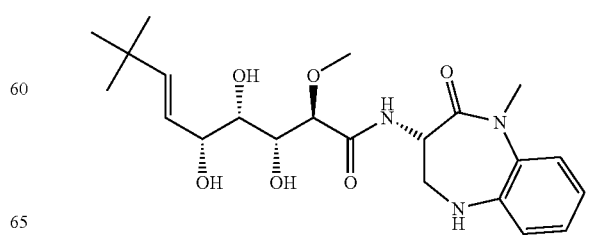

Step 1: Preparation of tert-butyl ((S)-1-methyl-2-oxo-2,3,4,5-tetrahydro-1H-1,5-benzodiazepin-3-yl)carbamate (9)

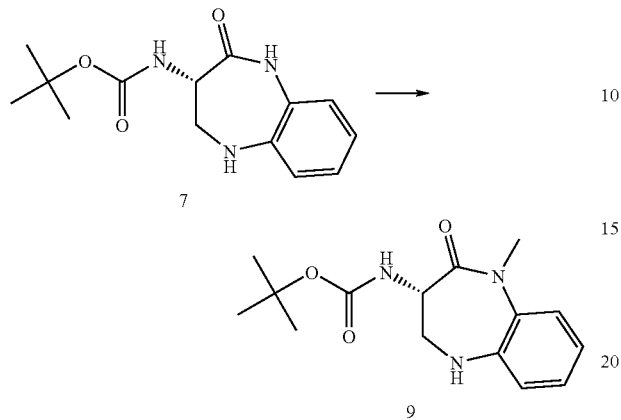

A solution of 250 mg of 7 (0.90 mmol) in 2 mL of THF is introduced dropwise into a 10 mL round-bottomed flask, with stirring and under an argon atmosphere, containing 2 mL of THF and 36 mg of sodium hydride in suspension at 60% in oil (0.90 mmol). The medium is stirred for 1 h and then 130 mg (0.91 mmol) of methyl iodide are added. The medium is kept stirring for 48 h, 5 mL of water are added and the mixture is extracted with 3 times 25 mL of AcOEt. The organic phases are combined, dried over MgSO$_4$, filtered and evaporated to dryness. 295 mg of crude product are obtained, which product is chromatographed on a silica cartridge (25 g, eluent heptane/AcOEt—in an AcOEt gradient: 25 to 100%). 169 mg of expected product 9 are recovered.

ES: m/z=292 MH$^+$.

Step 2: Preparation of 3-(S)-amino-1-methyl-1,3,4,5-tetrahydro-1,5-benzodiazepin-2-one hydrochloride (10)

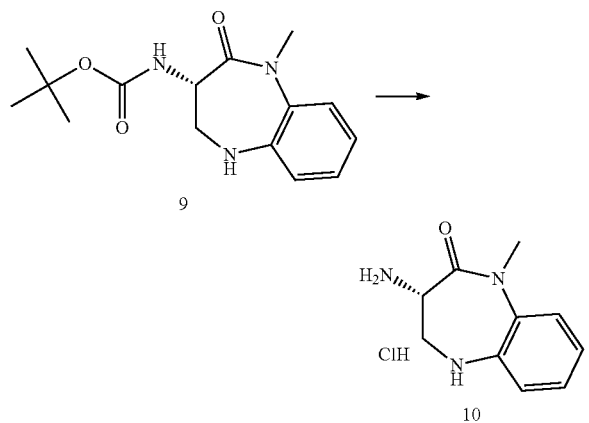

0.168 g of 9 (0.58 mmol) is taken up in a 25 mL round-bottomed flask and 6 mL of a solution of hydrochloric acid in dioxane (4M) are added. The medium is stirred for 4 h at RT under argon. A precipitate forms which is drained and dried under vacuum, 174 mg of expected product 10 are obtained in hydrochloride form.

ES: m/z=192 MH$^+$.

$[\alpha]_D$: −113+/−1.8 (c=1.987 mg/0.5 mL MeOH)

Step 3: Preparation of N-((S)-1-methyl-2-oxo-2,3,4,5-tetrahydro-1H-1,5-benzodiazepin-3-yl)-(E)-(2R,3R,4S,5R)-3,4,5-trihydroxy-2-methoxy-8,8-dimethyl-non-6-enamide (Ex4)

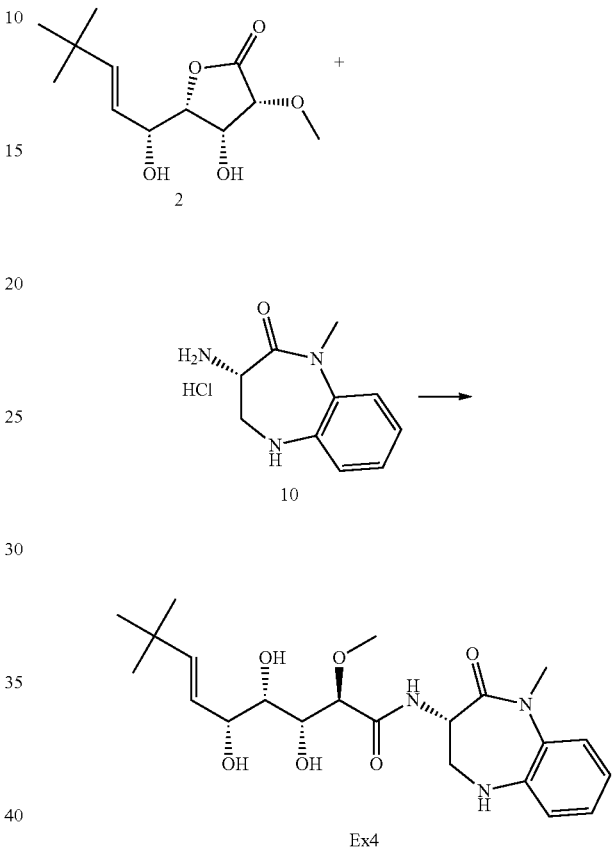

80 mg of 2 (328 μmol), 104 mg of 10 (393 μmol), 245 mg of sodium 2-ethylhexanoate (1.47 mmol) in 2.0 mL of THF are successively introduced into a 10 mL round-bottomed flask, with stirring and under an argon atmosphere. The stirring is maintained at RT for 48 h. 30 mL of ethyl acetate are added to the reaction medium.

The mixture is washed with 20 mL of a saturated aqueous NaCl solution. The organic phase is dried over anhydrous magnesium sulphate, filtered and then evaporated to dryness. 250 mg of crude product are obtained, which product is chromatographed on a silica cartridge (12 g, eluent CH$_2$Cl$_2$/MeOH 90/10). 117 mg of expected product Ex4 are recovered.

ES: m/z=458 MNa$^+$; m/z=436 MH$^+$.

$[\alpha]_D$: −3.3+/−0.4 (c=3.007 mg/0.5 mL MeOH)

$^1$H NMR (400 MHz, DMSO-d$_6$), δ(ppm): 0.96 (s, 9H); 3.22 (s, 3H); 3.25 (s, 3H); from 3.25 to 3.37 (m masked, 2H); from 3.47 to 3.62 (m, 2H); 3.69 (d, J=8.0 Hz, 1H); 3.93 (m, 1H); 4.31 (m, 2H); from 4.49 to 4.59 (m, 2H); 5.28 (d, J=6.0 Hz, 1H); 5.30 (dd, J=7.0 and 16.0 Hz, 1H); 5.62 (d, J=16.0 Hz, 1H); from 6.94 to 7.01 (m, 2H); 7.08 (broad t, J=8.0 Hz, 1H); 7.27 (d, J=8.0 Hz, 1H); 7.95 (d, J=8.0 Hz, 1H).

Ex5: N-((S)-1-methyl-4-oxo-2,3,4,5-tetrahydro-1H-
1,5-bezodiazepin-3-yl)-(E)-(2R,3R,4S,5R)-3,4,5-
trihydroxy-2-methoxy-8,8-dimethylnon-6-enamide

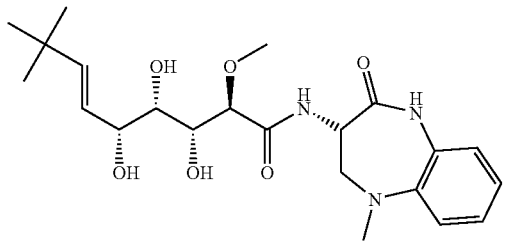

Step 1: Preparation of tert-butyl ((S)-1-methyl-4-
oxo-2,3,4,5-tetrahydro-1H-1,5-benzodiazepin-3-yl)
carbamate (11)

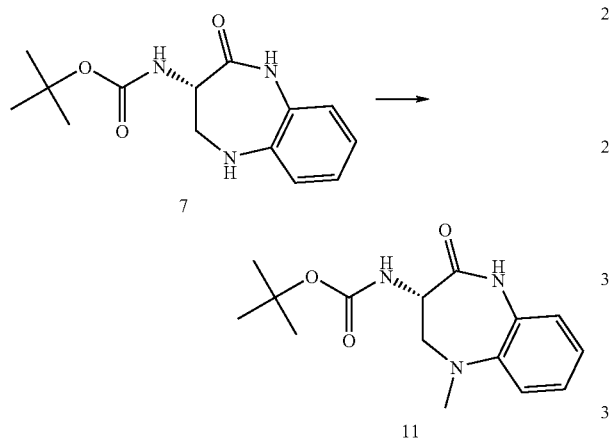

In a 30 mL vial, containing 300 mg of 7 (1.08 mmol), 200 mg of K$_2$CO$_3$ (1.45 mmol) and 3.07 g of methyl iodide (21.6 mmol) and 20 mL of acetone. The reaction medium is heated at 120° C. for 30 min in a microwave oven (300 Watt, Biotage). The mixture is filtered and evaporated to dryness. 395 mg of crude product are obtained, which product is chromatographed on a silica cartridge (25 g, eluent heptane/AcOEt—in a 25 to 100% AcOEt gradient). 211 mg of expected product 11 (white solid) are recovered.

ES: m/z=292 MH$^+$.

$^1$H NMR (400 MHz, DMSO-d$_6$), δ(ppm): 1.34 (s, 9H); 2.71 (s, 3H); 3.15 (m, 1H); 3.41 (m, 1H); 4.03 (m, 1H); from 6.92 to 7.04 (m, 3H); 7.10 (d, J=8.0 Hz, 1H); 7.17 (dt, J=1.5 and 8.0 Hz, 1H); 9.67 (s, 1H).

Step 2: Preparation of 3-(S)-amino-5-methyl-1,3,4,5-
tetrahydro-1,5-benzodiazepin-2-one hydrochloride
(12)

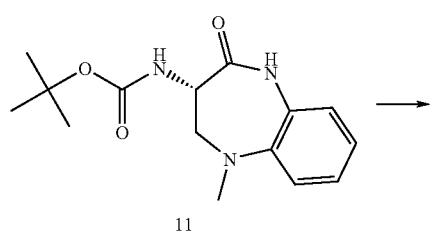

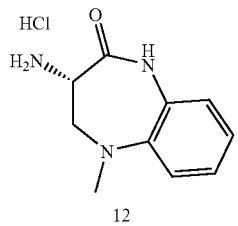

0.21 g of 11 (0.72 mmol) is taken up in a 25 mL round-bottomed flask and 5 mL of a solution of hydrochloric acid in dioxane (4M) is added. The medium is stirred overnight at RT under argon. A precipitate forms which is drained and dried under vacuum, 175 mg of expected product 12 are obtained in hydrochloride form.

ES: m/z=192 MH$^+$.

[α]$_D$: −52.4+/−1.1 (c=2.019 mg/0.5 mL MeOH)

Step 3: Preparation of N-((S)-1-methyl-4-oxo-2,3,4,
5-tetrahydro-1H-1,5-benzodiazepin-3-yl)-(E)-(2R,
3R,4S,5R)-3,4,5-trihydroxy-2-methoxy-8,8-dimeth-
ylnon-6-enamide (Ex5)

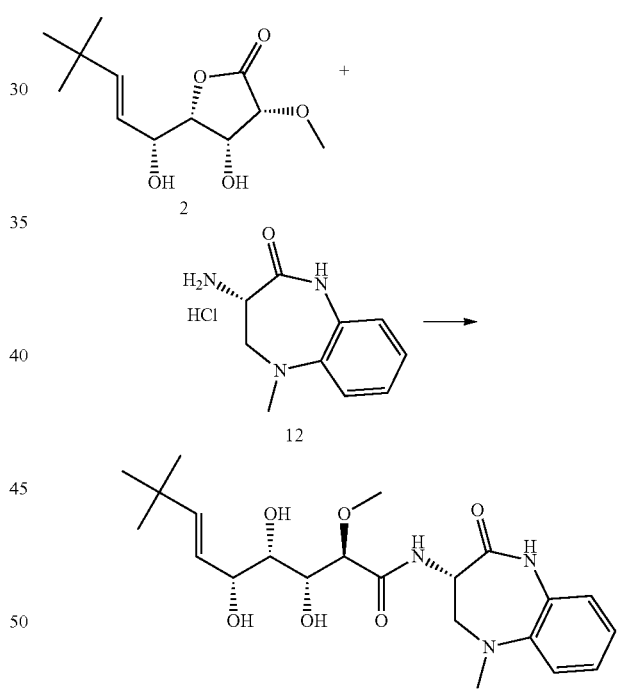

80 mg of 2 (328 μmol), 104 mg of 12 (393 μmol) and 245 mg of sodium 2-ethylhexanoate (1.47 mmol) in 2.0 mL of THF are successively introduced into a 10 mL round-bottomed flask, with stirring and under an argon atmosphere. The stirring is maintained at RT for 48 h. 30 mL of ethyl acetate are added to the reaction medium. The mixture is washed with 20 mL of a saturated aqueous NaCl solution. The organic phase is dried over anhydrous magnesium sulphate, filtered and then evaporated to dryness. 175 mg of crude product are obtained, which product is chromatographed on a silica cartridge (12 g, eluent CH$_2$Cl$_2$/MeOH 90/10). 74 mg of expected product Ex5 are recovered.

ES: m/z=458 MNa⁺; m/z=436 MH⁺.

[α]D: +51.4+/−1.1 (c=1.757 mg/0.5 mL MeOH)

$^1$H NMR (400 MHz, DMSO-$d_6$), δ(ppm): 0.96 (s, 9H); 2.73 (s, 3H); 3.23 (s, 3H); from 3.24 to 3.35 (m masked, 2H); 3.43 (m, 1H); 3.51 (m, 1H); 3.69 (d, J=8.0 Hz, 1H); 3.94 (m, 1H); 4.30 (m, 2H); 4.39 (m, 1H); 4.52 (d, J=4.5 Hz, 1H); 5.30 (dd, J=7.0 and 16.0 Hz, 1H); 5.62 (d, J=16.0 Hz, 1H); from 6.95 to 7.04 (m, 2H); 7.10 (broad d, J=8.0 Hz, 1H); 7.17 (m, 1H); 7.98 (d, J=7.5 Hz, 1H); 9.82 (s, 1H).

Ex6: N-(2-oxo-5-phenyl-2,3-dihydro-1H-1,4-benzodiazepin-3-yl)-(E)-(2R,3R,4S,5R)-3,4,5-trihydroxy-2-methoxy-8,8-dimethylnon-6-enamide

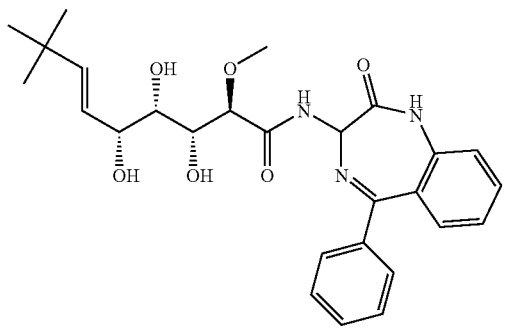

Ex6

Step 1: Preparation of 3-amino-5-phenyl-1,3-dihydro-1,4-benzodiazepin-2-one (14)

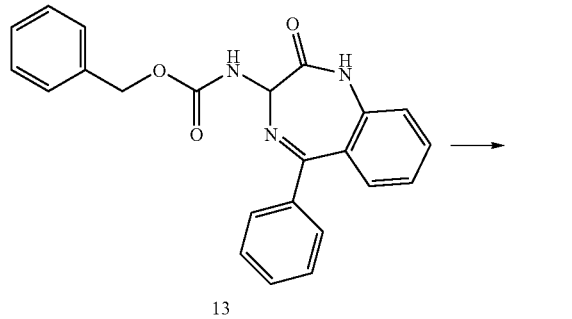

13

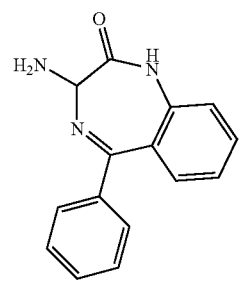

14

38 mg of 10% Pd/C are introduced into a 20 mL round-bottomed flask, with stirring and under an argon atmosphere, containing 7 mL of MeOH and 0.7 g 13 (1.82 mmol) (commercial from Neosystem) and 0.35 mL of formic acid (9.3 mmol). The reaction medium is heated at 50° C. for 6 h. The mixture is filtered on celite, rinsed with MeOH, taken up in 50 mL of $CH_2Cl_2$ and brought to pH 8 with a 32% aqueous ammonia solution. The mixture is extracted with $CH_2Cl_2$ and then washed with water. The organic phase is dried over MgSO4, filtered and evaporated to dryness. 0.437 g of expected product 14 is obtained.

CI: m/z=252 MH⁺.

$^1$H NMR (400 MHz, DMSO-$d_6$), δ(ppm): 4.22 (s, 1H); 7.19 (t, J=7.5 Hz, 1H); 7.25 (d, J=7.5 Hz, 2H); from 7.40 to 7.51 (m, 5H); 7.58 (dt, J=2.0 and 7.5 Hz, 1H); 10.65 (broad s, 1H).

Step 2: Preparation of N-(2-oxo-5-phenyl-2,3-dihydro-1H-1,4-benzodiazepin-3-yl)-(E)-(2R,3R,4S,5R)-3,4,5-trihydroxy-2-methoxy-8,8-dimethylnon-6-enamide (Ex6)

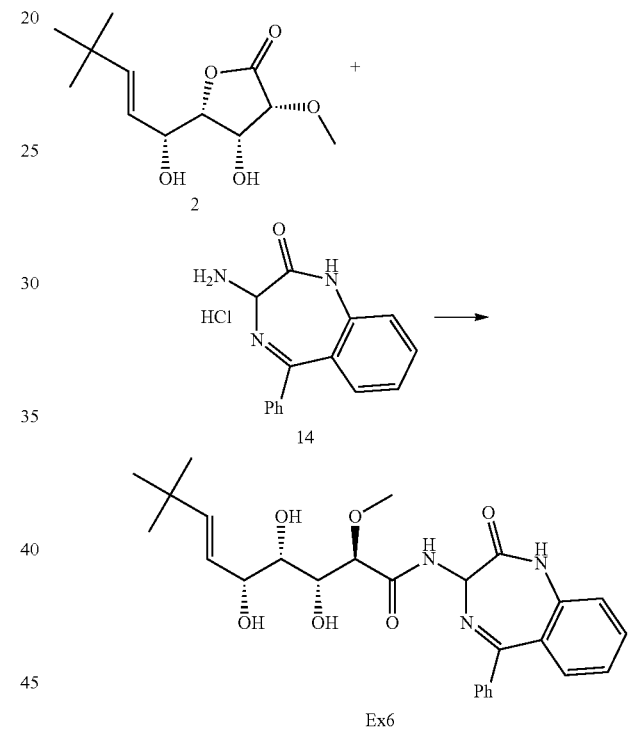

235 mg of 2 (818 μmol), 400 mg of 14 (1.59 mmol), 340 mg of sodium 2-ethylhexanoate (2.04 mmol) in 3.5 mL of THF are successively introduced into a 30 mL round-bottomed flask, with stirring and under an argon atmosphere. The mixture is heated at 60° C. for 5 h and the stirring is maintained at RT for 24 h. 15 mL of $CH_2Cl_2$ are added to the reaction medium. The mixture is washed with twice 10 mL of HCl (1N) and then 10 mL of a saturated aqueous NaCl solution. The organic phase is dried over anhydrous magnesium sulphate, filtered and then evaporated to dryness. 510 mg of crude product are obtained, which product is chromatographed on a silica cartridge (30 g, eluent $CH_2Cl_2$/MeOH 97/3). 73 mg of expected product Ex6 are recovered.

ES: m/z=496 MH+

$^1$H NMR (400 MHz, DMSO-d6), δ(ppm): (a 50%-50% mixture of isomers): 0.96 (s, 4.5H), 0.98 (s, 4.5H); 3.35 (s, 1.5H); 3.36 (s, 1.5H); 3.40 (m, 1H); 3.65 (broad m, 1H); 3.89 (d, J=7.5 Hz, 0.5H); 3.91 (d, J=7.5 Hz, 0.5H); 3.99 (m, 1H); from 4.23 to 4.65 (broad m, 3H); 5.22 (d, J=7.5 Hz, 0.5H);

5.26 (d, J=8.0 Hz, 0.5H); 5.34 (m, 1H); 5.63 (d, J=16.0 Hz, 0.5H); 5.65 (d, J=16.0 Hz, 0.5H); 7.26 (m, 1H); 7.32 (m, 2H); from 7.42 to 7.55 (m, 5H); 7.65 (m, 1H); 8.71 (d, J=8.0 Hz, 0.5H); 8.86 (d, J=7.5 Hz, 0.5H); 10.9 (broad m, 1H)

Ex7: (2R,3R,4S,5R,6E)-N-[(3S)-1-benzyl-4-oxo-2,3,4,5-tetrahydro-1H-1,5-benzodiazepin-3-yl]-3,4,5-trihydroxy-2-methoxy-8,8-dimethynon-6-enamide

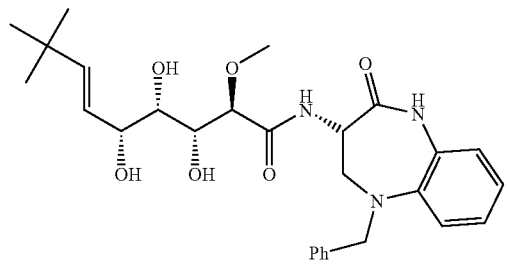

Ex7

Step 1: Preparation of tert-butyl [(3S)-1-benzyl-4-oxo-2,3,4,5-tetrahydro-1H-1,5-benzodiazepin-3-yl] carbamate (15)

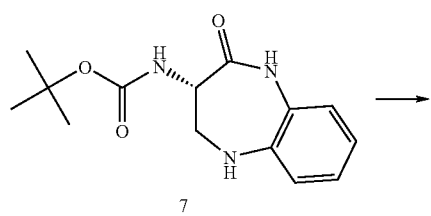

7

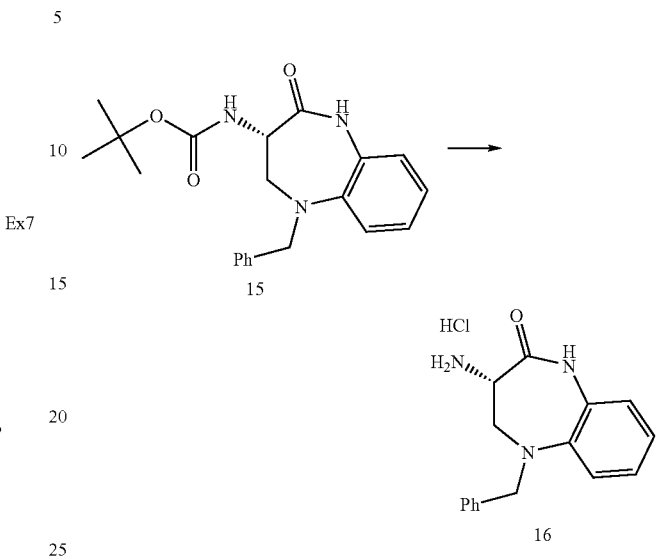

15

In a 5 mL vial, containing 110 mg of 7 (0.397 mmol), 129.2 mg of Cs$_2$CO$_3$ (0.397 mmol) and 136 mg of benzyl iodide (0.793 mmol) and 3.72 mL of methyl isobutyl ketone. The reaction medium is heated at 130° C. for 20 min in a microwave oven (300 Watt, Biotage). The mixture is filtered and evaporated to dryness. The crude product is chromatographed on a silica cartridge (20 g, eluent heptane/AcOEt—in a 25 to 100% AcOEt gradient). 116 mg of expected product 15 are recovered.

ES: m/z=368 MH$^+$ $^1$H NMR (400 MHz, DMSO-d$_6$), δ(ppm): 1.31 (s, 9H); 3.18 (m, 1H); 3.32 (m, 1H); from 4.04 to 4.15 (m, 2H); 4.40 (d, J=14.0 Hz, 1H); from 6.93 to 7.32 (m, 10H); 9.71 (s, 1H).

Step 2: Preparation of (3S)-3-amino-5-benzyl-1,3,4,5-tetrahydro-2H-1,5-benzodiazepin-2-one hydrochloride (16)

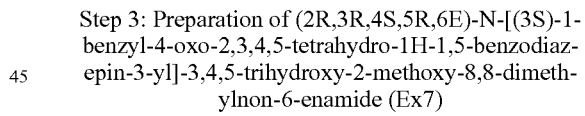

15

16

357.5 mg of 15 (0.97 mmol) prepared according to the procedure described in step 1 are taken up in a 25 mL round-bottomed flask and 6.3 ml of dioxane and 7.5 mL of a solution of hydrochloric acid in dioxane (4M) are added. The medium is stirred overnight at RT under argon. A precipitate forms which is drained and washed with isopropyl ether (15 mL) and dried under vacuum. 280 mg of expected product 16 (white solid) are obtained in hydrochloride form.

ES: m/z=267 MH$^+$ $^1$H NMR (400 MHz, DMSO-d$_6$), δ(ppm): from 3.32 to 3.52 (m partially masked, 2H); 3.95 (m, 1H); 4.17 (d, J=14.0 Hz, 1H); 4.43 (d, J=14.0 Hz, 1H); from 7.01 to 7.38 (m, 9H); 8.29 (broad s, 3H); 10.3 (s, 1H).

Step 3: Preparation of (2R,3R,4S,5R,6E)-N-[(3S)-1-benzyl-4-oxo-2,3,4,5-tetrahydro-1H-1,5-benzodiazepin-3-yl]-3,4,5-trihydroxy-2-methoxy-8,8-dimethylnon-6-enamide (Ex7)

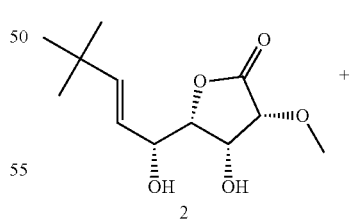

2

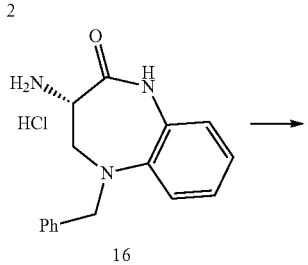

16

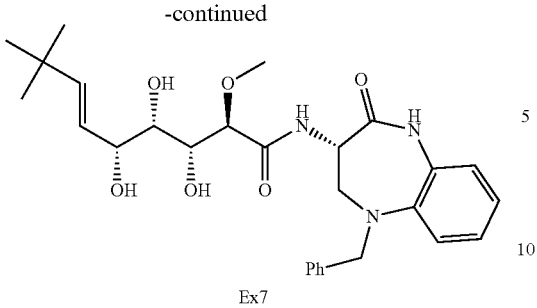

Ex7

67 mg of 2 (274 μmol), 141 mg of 16 (462 μmol) and 296 mg of sodium 2-ethylhexanoate (1.78 mmol) in 1.5 mL of THF are successively introduced into a 10 mL round-bottomed flask, with stirring and under an argon atmosphere. The stirring is maintained at RT for 3 days. The insolubles are filtered, washed with THF and then evaporated to dryness. The crude product is chromatographed on a silica cartridge (20 g, eluent AcOEt/MeOH 95/5). 85 mg of expected product Ex7 are recovered.

ES: m/z=512 MH$^+$

[α]$_D$: +153.4+/−2.4. C=1.572 mg/0.5 mL CH$_3$OH $^1$H NMR (400 MHz, DMSO-d$_6$), δ(ppm): 0.94 (s, 9H); 3.19 (s, 3H); from 3.20 to 3.42 (m partially masked, 3H); 3.49 (m, 1H); 3.64 (d, J=8.0 Hz, 1H); 3.91 (m, 1H); 4.12 (d, J=14.0 Hz, 1H); 4.23 (m, 2H); 4.41 (d, J=14.0 Hz, 1H); 4.45 (m, 1H); 4.50 (d, J=4.0 Hz, 1H); 5.29 (dd, J=7.0 and 16.0 Hz, 1H); 5.61 (d, J=16.0 Hz, 1H); 7.02 (m, 2H); from 7.10 to 7.35 (m, 7H); 8.02 (d, J=8.0 Hz, 1H); 9.83 (s, 1H).

Ex8: (2R,3R,4S,5R,6E)-N-[(3S)-1,5-dimethyl-2-oxo-2,3,4,5-tetrahydro-1H-1,5-benzodiazepin-3-yl]-3,4,5-trihydroxy-2-methoxy-8,8-dimethylnon-6-enamide

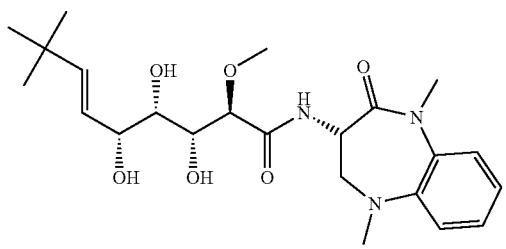

Ex8

Step 1: Preparation of tert-butyl [(3S)-1,5-dimethyl-2-oxo-2,3,4,5-tetrahydro-1H-1,5-benzodiazepin-3-yl]carbamate (17)

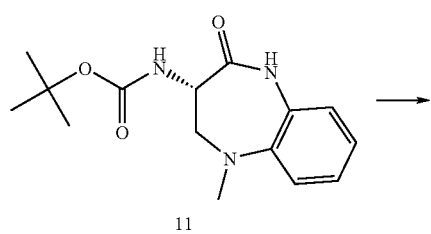

11

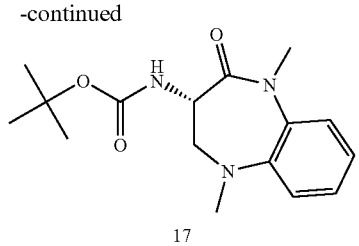

17

36 mg of sodium hydride in suspension at 60% in oil (0.90 mmol) are introduced at −10° C. into a 50 mL round-bottomed flask, with stirring and under an argon atmosphere, containing 10 mL of THF and 265 mg of 11 (0.91 mmol). The medium is stirred for 1 h, and then 148 mg (1.04 mmol) of methyl iodide are added. The medium is kept stirring at RT for 24 h. The mixture is concentrated, and 320 mg of crude product are obtained, which product is chromatographed on a silica cartridge (50 g, eluent heptane/AcOEt—in an AcOEt gradient: 10 to 50%). 235 mg of expected product 17 are recovered.

ES: m/z=328 MNa$^+$; m/z=306 MH$^+$.

$^1$H NMR (400 MHz, DMSO-d$_6$), δ(ppm): 1.33 (s, 9H); 2.69 (s, 3H); 3.03 (m, 1H); 3.21 (s, 3H); 3.35 (m, 1H); 4.04 (m, 1H); 7.03 (d, J=8.5 Hz, 1H); from 7.11 to 7.18 (m, 2H); 7.26 (t, J=8.0 Hz, 1H); 7.35 (d, J=8.0 Hz, 1H).

Step 2: Preparation of (3S)-3-amino-1,5-dimethyl-1,3,4,5-tetrahydro-2H-1,5-benzodiazepin-2-one hydrochloride (18)

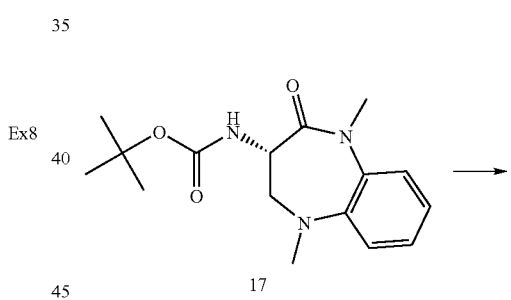

17

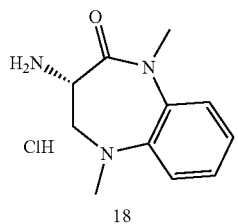

18

206.8 mg of 17 (0.677 mmol) are taken up in a 25 mL round-bottomed flask and 5 mL of a solution of hydrochloric acid in dioxane (4M) are added. The medium is stirred overnight at RT under argon. A precipitate forms. After having evaporated the solvent under vacuum, 213 mg of expected product 18 (white solid) are obtained in hydrochloride form.

ES: m/z=206 MH$^+$.

$^1$H NMR (400 MHz, DMSO-d$_6$), δ(ppm): 2.74 (s, 3H); 3.30 (s, 3H); 3.32 (m, 1H); 3.46 (m, 1H); 3.90 (m partially masked, 1H); from 7.15 to 7.24 (m, 2H); 7.31 (dt, J=1.5 and 7.5 Hz, 1H); 7.41 (dd, J=1.5 and 7.5 Hz, 1H); 8.34 (broad s, 3H).

Step 3: Preparation of (2R,3R,4S,5R,6E)-N-[(3S)-1,5-dimethyl-2-oxo-2,3,4,5-tetrahydro-1H-1,5-benzodiazepin-3-yl]-3,4,5-trihydroxy-2-methoxy-8,8-dimethylnon-6-enamide (Ex8)

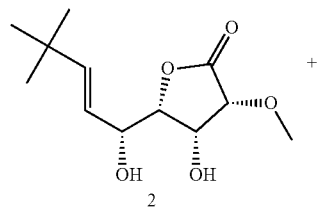

2

+

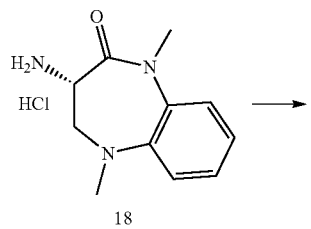

18

↓

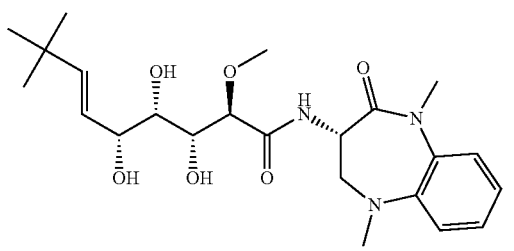

Ex4

208 mg of 2 (852 µmol), 198 mg of 18 (712 µmol) and 473 mg of sodium 2-ethylhexanoate (2.848 mmol) in 5.0 mL of THF are successively introduced into a 25 mL round-bottomed flask, with stirring and under an argon atmosphere. The stirring is maintained at RT for 48 h. The mixture is concentrated and evaporated to dryness. 923 mg of crude product are obtained, which product is chromatographed on a silica cartridge [50 g, eluent AcOEt/AcOEt-isopropanol (50/50), in an AcOEt-isopropanol (50/50) gradient: 0 to 50%]. 172 mg of expected product Ex8 are recovered.

[α]$_D$: +40.1+/−0.8. C=2.550 mg/0.5 mL CH$_3$OH.

ES: m/z=472 MNa$^+$; m/z=450 MH$^+$.

$^1$H NMR (400 MHz, DMSO-d$_6$), δ(ppm): 0.95 (s, 9H); 2.71 (s, 3H); 3.11 (dd, J=7.5 and 10.0 Hz, 1H); 3.21 (s, 3H); 3.24 (s, 3H); from 3.25 to 3.33 (m masked, 1H); 3.37 (dd, J=10.0 and 12.0 Hz, 1H); 3.49 (m, 1H); 3.69 (d, J=8.0 Hz, 1H); 3.92 (m, 1H); 4.32 (m, 2H); 4.40 (m, 1H); 4.54 (broad m, 1H); 5.29 (dd, J=7.0 and 16.0 Hz, 1H); 5.61 (broad d, J=16.0 Hz, 1H); from 7.12 to 7.19 (m, 2H); 7.28 (dt, J=1.5 and 7.5 Hz, 1H); 7.37 (dd, J=1.5 and 7.5 Hz, 1H); 8.03 (d, J=8.0 Hz, 1H).

Ex9: (2R,3R,4S,5R,6E)-N-[(3S)-5-ethyl-4-oxo-2,3,4,5-tetrahydro-1,5-benzoxazepin-3-yl]-3,4,5-trihydroxy-2-methoxy-8,8-dimethylnon-6-enamide

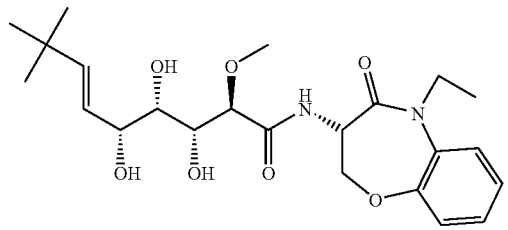

Ex9

Step 1: Preparation of tert-butyl [(3S)-5-ethyl-4-oxo-2,3,4,5-tetrahydro-1,5-benzoxazepin-3-yl]carbamate (19)

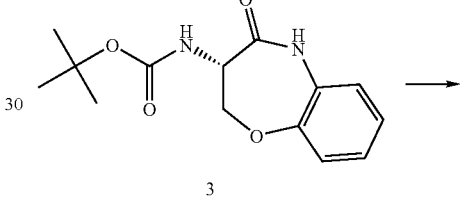

3

↓

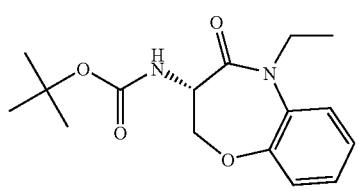

19

57 mg of sodium hydride in suspension at 60% in oil (1.44 mmol) are introduced at 0° C. into a 25 mL round-bottomed flask, with stirring and under an argon atmosphere, containing 6 mL of DMF and 400 mg of 3 (1.44 mmol). The medium is stirred for 1 h, and then 234 mg (1.50 mmol) of ethyl iodide are added. The medium is stirred at RT for 48 h, and then 50 mL of ice-cold water are added, and the mixture is extracted with 50 mL of AcOEt. The organic phase is dried over MgSO4, filtered and evaporated to dryness. 477 mg of crude product are obtained, which product is chromatographed on a silica cartridge (50 g, eluent heptane/AcOEt—in a 25 to 100% AcOEt gradient). 309 mg of expected product 19 (white solid) are recovered.

ES: m/z=307 MH$^+$; 329 MNa$^+$.

$^1$H NMR (400 MHz, DMSO-d$_6$), δ(ppm): 0.99 (t, J=7.0 Hz, 3H); 1.33 (s, 9H); 3.58 (m, 1H); 4.09 (m, 1H); from 4.21 to 4.36 (m, 3H); 7.10 (d, J=8.0 Hz, 1H); 7.19 (dd, J=2.0 and 8.0 Hz, 1H); from 7.23 to 7.34 (m, 2H); 7.48 (dd, J=2.0 and 8.0 Hz, 1H).

Step 2: Preparation of (3S)-3-amino-5-ethyl-2,3-dihydro-1,5-benzoxazepin-4(5H)-one hydrochloride (20)

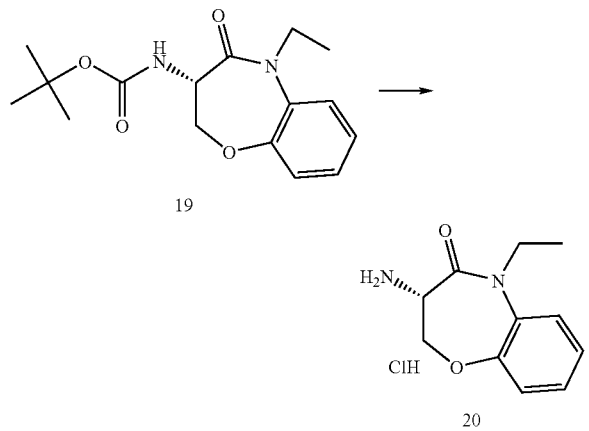

0.286 g of 19 (0.934 mmol) is taken up in a 50 mL round-bottomed flask and 7 mL of dioxane and 7 mL of a solution of hydrochloric acid in dioxane (4M) are added. The medium is stirred overnight at RT under argon. After evaporation of the solvent, the residue is taken up in 1 mL of CH$_2$Cl$_2$ and 10 mL of isopropyl ether. The solid formed is drained and dried under vacuum. 185 mg of expected product 20 (white solid) are thus recovered.

m.p.: 237.9+/−1° C.

$^1$H NMR (400 MHz, DMSO-d$_6$), δ(ppm): 1.05 (t, J=7.0 Hz, 3H); 3.70 (m, 1H); 4.10 (m, 1H); 4.19 (dd, J=8.0 and 10.0 Hz, 1H); 4.40 (t, J=10.0 Hz, 1H); 4.50 (dd, J=8.0 and 10.0 Hz, 1H); from 7.23 to 7.39 (m, 3H); 7.53 (m, 1H); 8.18 (broad m, 3H).

Step 3: Preparation of (2R,3R,4S,5R,6E)-N-[(3S)-5-ethyl-4-oxo-2,3,4,5-tetrahydro-1,5-benzoxazepin-3-yl]-3,4,5-trihydroxy-2-methoxy-8,8-dimethylnon-6-enamide (Ex9)

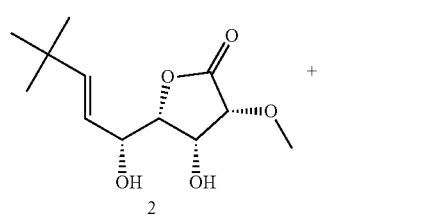

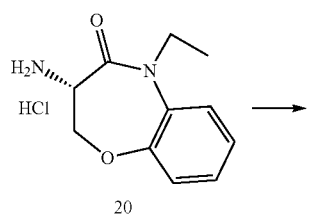

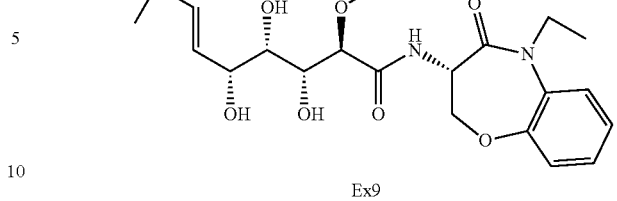

181 mg of 2 (742 μmol), 180 mg of 20 (742 μmol) and 296 mg of sodium 2-ethylhexanoate (1.78 mmol) in 3 mL of THF are successively introduced into a 25 mL round-bottomed flask, with stirring and under an argon atmosphere. The stirring is maintained at RT for 24 h. The mixture is concentrated and 727 mg of crude product are obtained, which product is chromatographed on a silica cartridge [50 g, eluent heptane/AcOEt-heptanel (50/50), in an AcOEt-heptane (50/50) gradient: 0 to 100%]. 177 mg of expected product Ex9 are recovered.

ES: m/z=473 MNa$^+$.

$^1$H NMR (400 MHz, DMSO-d$_6$), δ(ppm): 0.95 (s, 9H); 1.01 (t, J=7.0 Hz, 3H); 3.21 (s, 3H); from 3.23 to 3.35 (m masked, 1H); 3.50 (m, 1H); 3.61 (m, 1H); 3.69 (d, J=8.0 Hz, 1H); 3.92 (m, 1H); 4.09 (m, 1H); from 4.25 to 4.35 (m, 3H); 4.52 (d, J=4.0 Hz, 1H); 4.68 (m, 1H); 5.29 (dd, J=7.0 and 16.0 Hz, 1H); 5.62 (d, J=16.0 Hz, 1H); 7.21 (m, 1H); from 7.25 to 7.35 (m, 2H); 7.50 (m, 1H); 8.10 (d, J=8.0 Hz, 1H).

Ex10: (2R,3R,4S,5R,6E)-N-[(3S)-5-allyl-4-oxo-2,3,4,5-tetrahydro-1,5-benzoxazepin-3-yl]-3,4,5-trihydroxy-2-methoxy-8,8-dimethylnon-6-enamide

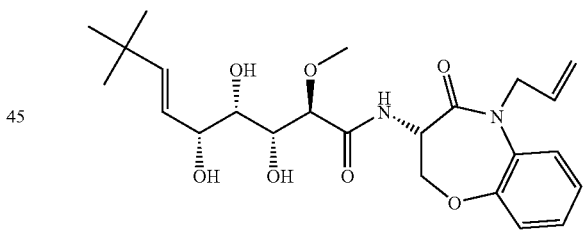

Step 1: Preparation of tert-butyl [(3S)-5-allyl-4-oxo-2,3,4,5-tetrahydro-1,5-benzoxazepin-3-yl]carbamate (21)

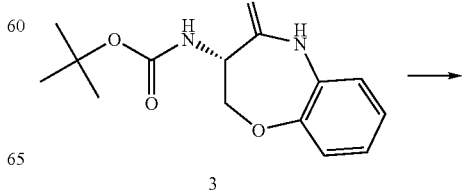

86 mg of sodium hydride in suspension at 60% in oil (2.16 mmol) are introduced at 0° C. into a 25 mL round-bottomed flask, with stirring and under an argon atmosphere, containing 5 mL of DMF and 600 mg of 3 (2.16 mmol). The medium is stirred for 1 h, and then 264 mg (2.18 mmol) of allyl iodide are added. The medium is stirred at 0° C. for 2 h, and then 10 mL of ice-cold water are added, and the mixture is extracted 3 times with 25 mL of AcOEt. The combined organic phases are dried over MgSO4, filtered and evaporated to dryness. The crude product is chromatographed on a silica cartridge (50 g, eluent heptane/AcOEt—in a 5 to 30% AcOEt gradient.) 430 mg of expected product 21 (white solid) are recovered.

$^1$H NMR (400 MHz, DMSO-d$_6$), δ(ppm): 1.34 (s, 9H); from 4.24 to 4.46 (m, 4H); 4.61 (m, 1H); 5.04 (broad d, J=10.0 Hz, 1H); 5.12 (broad d, J=17.0 Hz, 1H); 5.22 (m, 1H); 7.14 (d, J=8.0 Hz, 1H); from 7.17 to 7.32 (m, 3H); 7.46 (m, 1H).

Step 2: Preparation of (3S)-5-allyl-3-amino-2,3-dihydro-1,5-benzoxazepin-4(5H)-one hydrochloride (22)

0.430 g of 21 (1.35 mmol) is taken up in a 50 mL round-bottomed flask and 10 mL of dioxane and 10 mL of a solution of hydrochloric acid in dioxane (4M) are added. The medium is stirred overnight at RT under argon. After evaporation of the solvent, the residue is taken up in 10 mL of CH$_2$Cl$_2$ and then 10 mL of isopropyl ether. The solid formed is drained and dried under vacuum. 350 mg of expected product 22 (white solid) are thus recovered.

m.p.: 202.7+/−1° C.

[α]$_D$: −257.9+/−2.8 (c=2.634 mg/0.5 mL MeOH)

$^1$H NMR (400 MHz, DMSO-d$_6$), δ(ppm): from 4.20 to 4.65 (m, 5H); 5.09 (broad d, J=10.0 Hz, 1H); 5.19 (broad d, J=18.0 Hz, 1H); 5.28 (m, 1H); from 7.21 to 7.38 (m, 3H); 7.50 (m, 1H); 8.25 (broad m, 3H).

Step 3: Preparation of (2R,3R,4S,5R,6E)-N-[(3S)-5-allyl-4-oxo-2,3,4,5-tetrahydro-1,5-benzoxazepin-3-yl]-3,4,5-trihydroxy-2-methoxy-8,8-dimethylnon-6-enamide (Ex10)

224 mg of 2 (916 μmol), 350 mg of 22 (1.374 mmol) and 457 mg of sodium 2-ethylhexanoate (2.748 mmol) in 5 mL of THF are successively introduced into a 25 mL round-bottomed flask, with stirring and under an argon atmosphere. The stirring is maintained at RT for 48 h. The mixture is concentrated and 920 mg of crude product are obtained, which product is chromatographed on a silica cartridge [50 g, eluent heptane/AcOEt, in an AcOEt gradient: 30 to 100%]. 280 mg of expected product Ex10 are recovered.

ES: m/z=461 (M−H$^+$)

[α]$_D$: −114.9+/−1.8. (c=1.999 mg/0.5 mL CH$_3$OH)

$^1$H NMR (400 MHz, DMSO-d$_6$), δ(ppm): 0.95 (s, 9H); 3.21 (s, 3H); 3.29 (m masked, 1H); 3.50 (m, 1H); 3.69 (d, J=8.0 Hz, 1H); 3.92 (m, 1H); from 4.22 to 4.42 (m, 5H); 4.53 (d, J=5.5 Hz, 1H); 4.60 (dd, J=5.5 and 16.0 Hz, 1H); 4.74 (m, 1H); 5.04 (broad d, J=11.0 Hz, 1H); 5.15 (broad d, J=18.0 Hz, 1H); 5.29 (dd, J=7.0 and 16.0 Hz, 1H); 5.62 (d, J=16.0 Hz, 1H); 5.74 (m, 1H); from 7.18 to 7.32 (m, 3H); 7.47 (m, 1H); 8.17 (d, J=8.0 Hz, 1H).

Ex11: (2R,3R,4S,5R,6E)-3,4,5-trihydroxy-2-methoxy-8,8-dimethyl-N-[(3S)-4-oxo-5-propyl-2,3,4,5-tetrahydro-1,5-benzoxazepin-3-yl]non-6-enamide

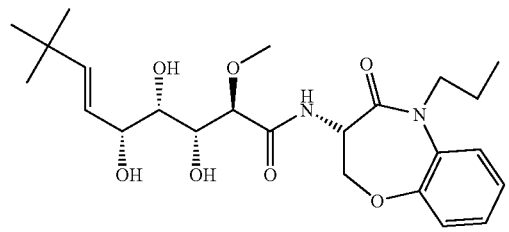

Step 1: Preparation of tert-butyl [(3S)-4-oxo-5-propyl-2,3,4,5-tetrahydro-1,5-benzoxazepin-3-yl]carbamate (23)

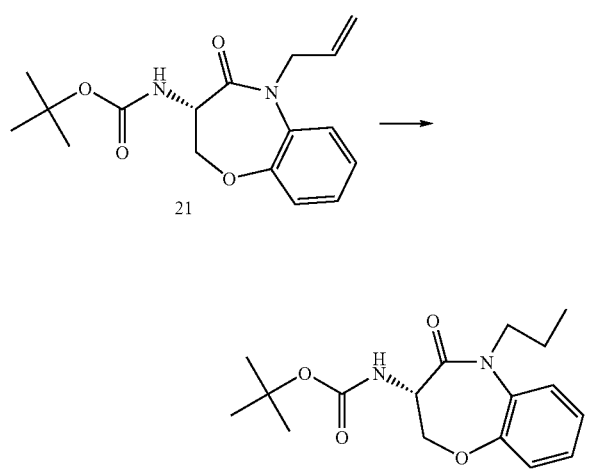

In an autoclave containing 270 mg of 21 (0.848 mmol), 20 mg of Pd/C (10%) and 5 mL of MeOH, hydrogenation is performed at 4 bar for 16 h at 20° C. After filtration of the catalyst on celite and evaporation of the solvent, 257 mg of expected product 23 are obtained, which product is used directly for the next stage.

ES: m/z=321 MH$^+$; 343 MNa$^+$.

$^1$H NMR (400 MHz, DMSO-d$_6$), δ(ppm): 0.75 (t, J=7.5 Hz, 3H); from 1.20 to 1.50 (m, 2H); 1.32 (s, 9H); 3.51 (m, 1H); 4.12 (m, 1H); from 4.22 to 4.38 (m, 3H); 7.08 (d, J=8.0 Hz, 1H); 7.19 (m, 1H); from 7.21 to 7.33 (m, 2H); 7.48 (m, 1H).

Step 2: Preparation of (3S)-3-amino-5-propyl-2,3-dihydro-1,5-benzoxazepin-4(5H)-one hydrochloride (24)

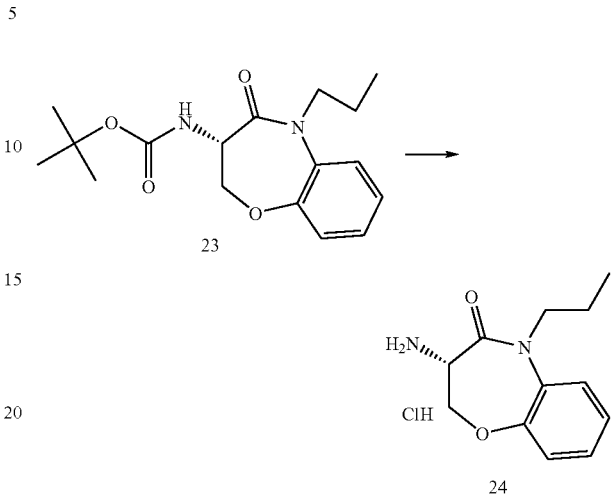

250 mg of 23 (0.78 mmol) are taken up in a 50 mL round-bottomed flask and 5 mL of dioxane and 5.8 mL of a solution of hydrochloric acid in dioxane (4M) are added. The medium is stirred overnight at RT under argon. After evaporation of the solvent, the residue is taken up in 2 mL of CH$_2$Cl$_2$ and then 50 mL of isopropyl ether. The solid formed is drained and dried under vacuum. 185 mg of expected product 24 (white solid) are thus recovered.

m.p.: 220.1+/−1° C.

[α]$_D$: −259.1+/−2.8. (c=2.191 mg/0.5 mL CH$_3$OH)

$^1$H NMR (400 MHz, DMSO-d$_6$), δ(ppm): 0.79 (t, J=7.5 Hz, 3H); from 1.31 to 1.54 (m, 2H); 3.61 (m, 1H); 4.16 (m, 1H); 4.21 (dd, J=7.5 and 10.0 Hz, 1H); 4.41 (t, J=10.0 Hz, 1H); 4.52 (dd, J=7.5 and 10.0 Hz, 1H); from 7.23 to 7.38 (m, 3H); 7.53 (m, 1H); 8.22 (broad m, 3H).

Step 3: Preparation of (2R,3R,4S,5R,6E)-3,4,5-trihydroxy-2-methoxy-8,8-dimethyl-N-[(3S)-4-oxo-5-propyl-2,3,4,5-tetrahydro-1,5-benzoxazepin-3-yl]non-6-enamide (Ex11)

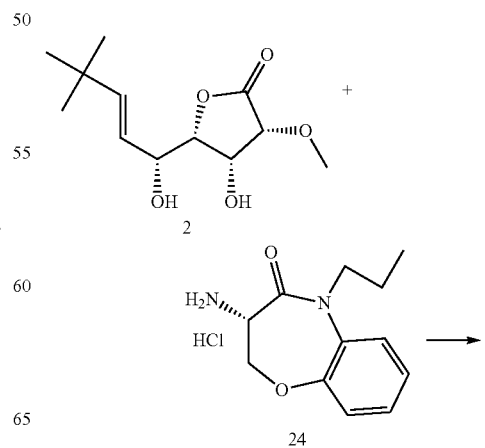

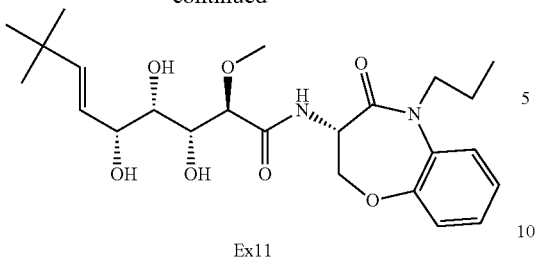
Ex11

134 mg of 2 (549 µmol), 169 mg of 24 (0.659 mmol) and 350 mg of sodium 2-ethylhexanoate (2.11 mmol) in 2 mL of THF are successively introduced into a 25 mL round-bottomed flask, with stirring and under an argon atmosphere. The stirring is maintained at RT for 1 week. The mixture is concentrated under vacuum. The crude product is chromatographed on a silica cartridge [20 g, eluent $CH_2Cl_2/CH_2Cl_2$-MeOH (90/10), in a $CH_2Cl_2$-MeOH (90/10) gradient: 10 to 30%]. 178 mg of expected product Ex11 are recovered.

ES: m/z=463 (M-H$^+$)

[α]D: −114.7+/−1.9. (c=1.737 mg/0.5 mL $CH_3OH$)

$^1$H NMR (400 MHz, DMSO-d$_6$), δ(ppm): 0.78 (t, J=7.5 Hz, 3H); 0.95 (s, 9H); from 1.30 to 1.52 (m, 2H); 3.21 (s, 3H); 3.30 (m masked, 1H); from 3.47 to 3.60 (m, 2H); 3.69 (d, J=8.0 Hz, 1H); 3.92 (m, 1H); 4.13 (m, 1H); from 4.25 to 4.39 (m, 4H); 4.52 (m, 1H); 4.69 (m, 1H); 5.30 (dd, J=7.0 and 16.0 Hz, 1H); 5.62 (d, J=16.0 Hz, 1H); 7.22 (m, 1H); from 7.24 to 7.35 (m, 2H); 7.50 (m, 1H); 8.11 (d, J=8.0 Hz, 1H).

Ex12: (2R,3R,4S,5R,6E)-3,4,5-trihydroxy-N-[(3S)-5-isopropyl-4-oxo-2,3,4,5-tetrahydro-1,5-benzoxazepin-3-yl]-2-methoxy-8,8-dimethylnon-6-enamide

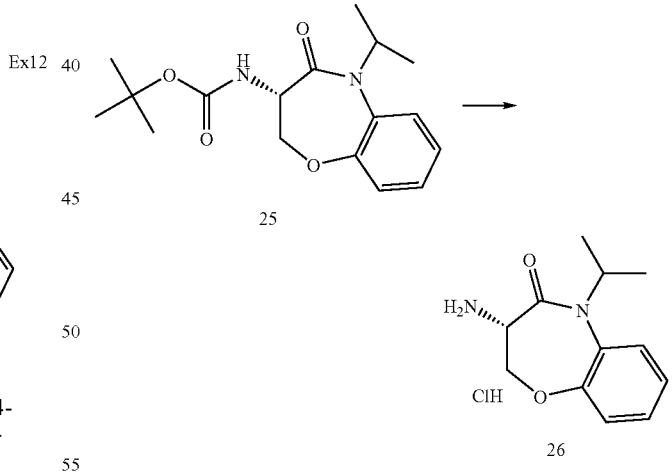

Step 1: Preparation of tert-butyl [(3S)-5-isopropyl-4-oxo-2,3,4,5-tetrahydro-1,5-benzoxazepin-3-yl]carbamate (25)

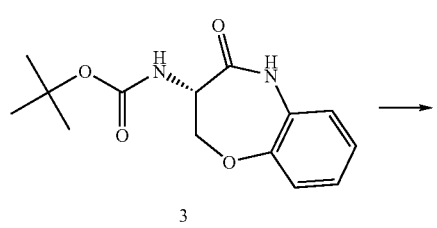

28 mg of sodium hydride in suspension at 60% in oil (0.719 mmol) are introduced at −10° C. into a 10 mL round-bottomed flask, with stirring and under an argon atmosphere, containing 4 mL of DMF and 200 mg of 3 (0.719 mmol). The medium is stirred for 1 h, and then 136 mg (2.23 mmol) of isopropyl iodide are added. The medium is allowed to slowly return to RT, and it is stirred overnight, and then 50 mL of ice-cold water are added and the mixture is extracted with 50 mL of AcOEt. The organic phase is dried over MgSO4, filtered and evaporated to dryness. The crude product is chromatographed on a silica cartridge (20 g, eluent heptane/AcOEt—in an AcOEt 10 to 50% gradient). 97 mg of expected product 25 are recovered.

ES: m/z=321 MH$^+$; 343 MNa$^+$.

$^1$H NMR (400 MHz, DMSO-d$_6$), δ(ppm): 1.03 (d, J=7.5 Hz, 3H); 1.32 (s, 9H); 1.35 (d, J=7.5 Hz, 3H); from 4.10 to 4.30 (m, 3H); 4.60 (m, 1H); 6.99 (d, J=8.0 Hz, 1H); 7.20 (dd, J=2.0 and 8.0 Hz, 1H); from 7.25 to 7.35 (m, 2H); 7.40 (dd, J=2.0 and 8.0 Hz, 1H).

Step 2: Preparation of (3S)-3-amino-5-isopropyl-2,3-dihydro-1,5-benzoxazepin-4(5H)-one hydrochloride (26)

216 mg of 25 (0.67 mmol) are taken up in a 50 mL round-bottomed flask and 2 mL of dioxane and 5.5 mL of a solution of hydrochloric acid in dioxane (4M) are added. The medium is stirred overnight at RT under argon. After evaporation of the solvent, the residue is taken up in 10 mL of isopropyl ether. The solid formed is drained and dried under vacuum. 169 mg of expected product 26 (white solid) are thus recovered.

m.p.: 248.8+/−1° C.

ES: m/z=221 MH$^+$; 243 MNa$^+$.

[α]$_D$: −197.7+/−2.9. (c=1.585 mg/0.5 mL $CH_3OH$)

¹H NMR (400 MHz, DMSO-d₆), δ(ppm): 1.12 (d, J=7.0 Hz, 3H); 1.41 (d, J=7.0 Hz, 3H); 4.09 (dd, J=7.5 and 10.0 Hz, 1H); 4.33 (t, J=10.0 Hz, 1H); 4.42 (dd, J=7.5 and 10.0 Hz, 1H); 4.59 (m, 1H); 7.28 (dd, J=2.0 and 8.0 Hz, 1H); from 7.30 to 7.40 (m, 2H); 7.45 (dd, J=2.0 and 8.0 Hz, 1H); 8.15 (broad m, 3H).

Step 3: Preparation of (2R,3R,4S,5R,6E)-3,4,5-trihydroxy-N-[(3S)-5-isopropyl-4-oxo-2,3,4,5-tetrahydro-1,5-benzoxazepin-3-yl]-2-methoxy-8,8-dimethylnon-6-enamide) (Ex12)

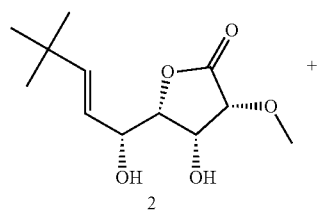

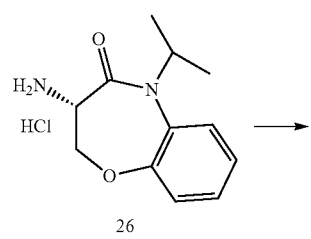

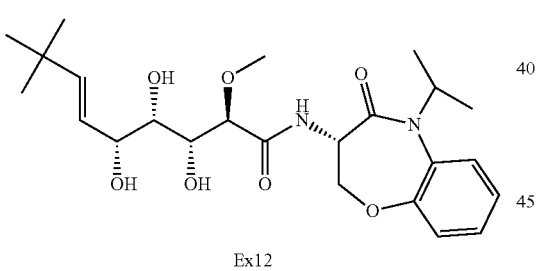

Ex12

172 mg of 2 (704 µmol), 151 mg of 26 (0.588 mmol) and 254 mg of sodium 2-ethylhexanoate (2.11 mmol) in 3 mL of THF are successively introduced into a 25 mL round-bottomed flask. The stirring is maintained at RT for 3 days. The mixture is concentrated under vacuum. The crude product is chromatographed on a silica cartridge [40 g, eluent heptane/AcOEt—in an AcOEt 10 to 100% gradient). 181 mg of expected product Ex12 are recovered.

ES: m/z=463 (M−H⁺)

[α]$_D$: −84.2+/−1.4 (c=2.028 mg/0.5 mL CH₃OH)

¹H NMR (400 MHz, DMSO-d₆), δ(ppm): 0.95 (s, 9H); 1.08 (d, J=7.0 Hz, 3H); 1.37 (d, J=7.0 Hz, 3H); 3.21 (s, 3H); 3.30 (m masked, 1H); 3.49 (m, 1H); 3.68 (d, J=8.0 Hz, 1H); 3.92 (m,1H); from 4.20 to 4.35 (m, 4H); from 4.51 to 4.65 (m, 3H); 5.29 (dd, J=7.5 and 16.0 Hz, 1H); 5.62 (d, J=16.0 Hz, 1H); 7.23 (dd, J=2.0 and 8.0 Hz, 1H); from 7.26 to 7.38 (m, 2H); 7.42 (dd, J=2.0 and 8.0 Hz, 1H); 8.02 (d, J=8.0 Hz, 1H).

Ex13: (2R,3R,4S,5R,6E)-N-[(3S)-5-(3,5-difluorobenzyl)-4-oxo-2,3,4,5-tetrahydro-1,5-benzoxazepin-3-yl]-3,4,5-trihydroxy-2-methoxy-8,8-dimethylnon-6-enamide

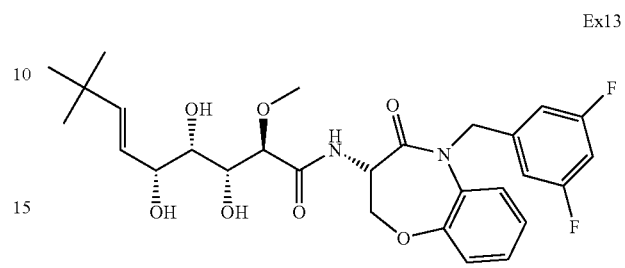

Ex13

Step 1: Preparation of tert-butyl [(3S)-5-(3,5-difluorobenzyl)-4-oxo-2,3,4,5-tetrahydro-1,5-benzoxazepin-3-yl]carbamate (27)

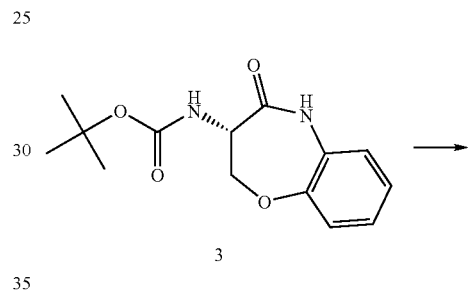

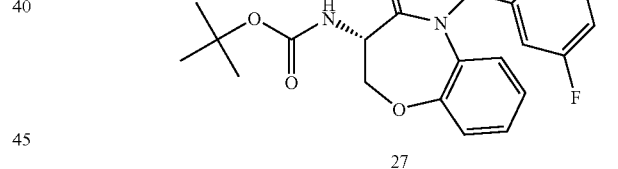

27

A solution of 3 (300 mg, 1.08 mmol) in 1.5 mL of THF is introduced at 20° C. into a 10 mL round-bottomed flask, with stirring and under an argon atmosphere, containing 1 mL of THF and 43 mg of sodium hydride in suspension at 60% in oil (1.08 mmol). The medium is stirred for 1 h, and then 0.446 mg (2.16 mmol) of 3,5-difluorobenzyl bromide is added. The mixture is stirred overnight, and then 5 mL of water are added and the mixture is extracted 3 times with 15 mL of AcOEt. The combined organic phases are dried over MgSO4, filtered and evaporated to dryness. The crude product is chromatographed on a silica cartridge (20 g, eluent heptane/AcOEt—in a 5 to 50% AcOEt gradient). 313 mg of expected product 27 are recovered.

ES: m/z=405 MH⁺

¹H NMR (400 MHz, DMSO-d₆), δ(ppm): 1.35 (s, 9H); from 4.32 to 4.53 (m, 3H); 4.98 (d, J=16.0 Hz, 1H); 5.27 (d, J=16.0 Hz, 1H); 6.91 (m, 2H); 7.04 (tt, J=2.0 and 9.0 Hz, 1H); from 7.18 to 7.30 (m, 4H); 7.43 (m, 1H).

Step 2: Preparation of (3S)-3-amino-5-(3,5-difluorobenzyl)-2,3-dihydro-1,5-benzoxazepin-4(5H)-one hydrochloride (28)

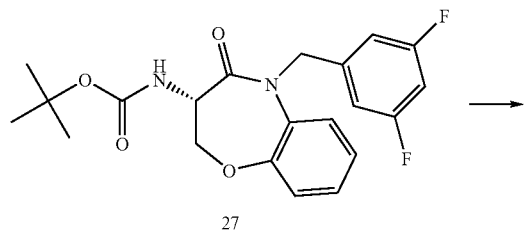

27

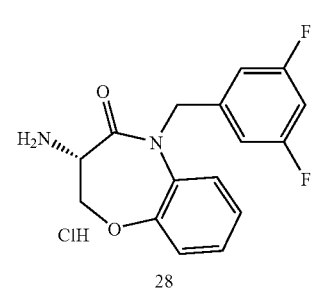

28

300 mg of 27 (0.74 mmol) are taken up in a 50 mL round-bottomed flask and 4.8 mL of dioxane and 5.6 mL of a solution of hydrochloric acid in dioxane (4M) are added. The medium is stirred overnight at RT under argon. After evaporation of the solvent, the residue is taken up in 5 mL of CH$_2$Cl$_2$ and then 100 mL of isopropyl ether. The solid formed is drained and dried under vacuum. 234 mg of expected product 28 (white solid) are thus recovered.

m.p.: 208+/−1° C.
[α]D: −196.5+/−2.6 c=2.294 mg/0.5 mL MeOH
ES: m/z=305 MH$^+$; 327 MNa$^+$.
$^1$H NMR (400 MHz, DMSO-d$_6$), δ(ppm): from 4.28 to 4.62 (m, 3H); 5.09 (d, J=16.0 Hz, 1H); 5.25 (d, J=16.0 Hz, 1H); 6.95 (m, 2H); 7.10 (tt, J=2.0 and 9.0 Hz, 1H); from 7.24 to 7.35 (m, 3H); 7.46 (m, 1H); 8.33 (broad s, 3H).

Step 3: Preparation of (2R,3R,4S,5R,6E)-N-[(3S)-5-(3,5-difluorobenzyl)-4-oxo-2,3,4,5-tetrahydro-1,5-benzoxazepin-3-yl]-3,4,5-trihydroxy-2-methoxy-8,8-dimethylnon-6-enamide (Ex13)

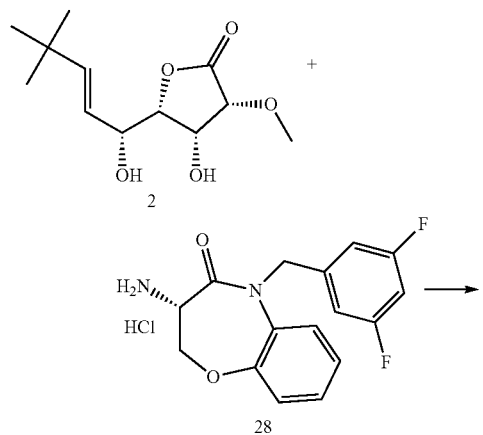

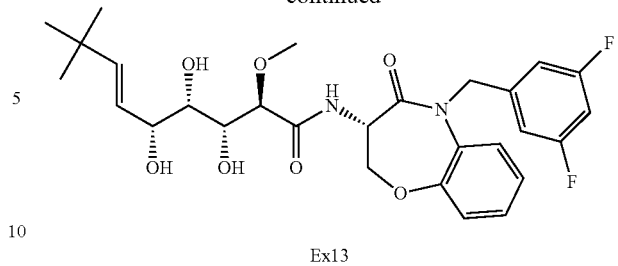

Ex13

132 mg of 2 (540 μmol), 230 mg of 28 (0.675 mmol) and 404 mg of sodium 2-ethylhexanoate (2.43 mmol) in 3.5 mL of THF are successively introduced into a 10 mL round-bottomed flask, with stirring an under an argon atmosphere. The stirring is maintained at RT for 2 days. The mixture is concentrated under vacuum. The crude product is chromatographed on a silica cartridge [40 g, eluent heptane/AcOEt—in a 30 to 100% AcOEt gradient). 96 mg of expected product Ex12 are recovered.

[α]D: −123.4+/−1.8 c=2.065 mg/0.5 mL MeOH
m.p.: 71.6+/−1° C.
ES: ES: m/z=549 MH$^+$.
$^1$H NMR (400 MHz, DMSO-d$_6$), δ(ppm): 0.95 (s, 9H); 3.22 (s, 3H); 3.30 (m masked, 1H); 3.51 (m, 1H); 3.70 (d, J=8.0 Hz, 1H); 3.93 (m, 1H); from 4.21 to 4.55 (m, 5H); 4.80 (m, 1H); 4.98 (d, J=16.0 Hz, 1H); from 5.23 to 5.35 (m, 2H); 5.62 (d, J=16.0 Hz, 1H); 6.92 (m, 2H); 7.07 (tt, J=2.0 and 9.0 Hz, 1H); from 7.20 to 7.30 (m, 3H); 7.48 (m, 1H); 8.28 (d, J=8.0 Hz, 1H).

Ex14: (2R,3R,4S,5R,6E)-7-cyclopentyl-3,4,5-trihydroxy-2-methoxy-N-[(3S)-5-methyl-4-oxo-2,3,4,5-tetrahydro-1,5-benzoxazepin-3-yl]hept-6-enamide

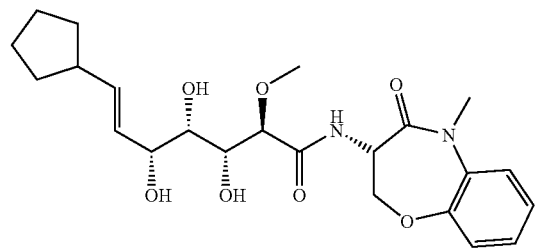

Ex14

Step 1: Preparation of (4R,4aS,7R,7aR)-7-methoxy-2,2-dimethyl-4-vinyltetrahydro-6H-furo[3,2-d][1,3]dioxin-6-one (30)

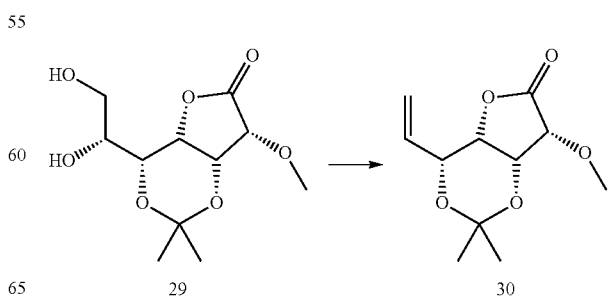

178.2 g of PPh$_3$ (0.679 mol), 84.1 g of imidazole (1.235 mol) and 2430 mL of anhydrous THF are loaded under nitrogen into a 4000 mL round-bottomed flask equipped with mechanical stirring. 156.8 g of twice-sublimed iodine (0.618 mol) are added with care while the temperature of the reaction mixture is maintained at 30° C. This medium is heated under reflux (66° C.) for 1 h, and then 81 g of 29 (0.309 mol) (which may be prepared according to the procedures described in Org. Process Res. Dev. 2003, 7(6), 856-865) are then gradually added at 66° C.+/−2° C. The homogeneous medium thus obtained is heated under reflux for 3 h. The mixture is allowed to return to 20° C.+/−5° C., and then 1000 mL of a 10% NaHCO$_3$ solution are poured in (effervescence, athermic) (pH 8.0-8.5). Next, 185.5 g of Na$_2$S$_2$O$_3$ are added until almost complete decolourization is obtained (appearance of an inorganic precipitate). After stirring at 20° C.+/−5° C. for 30 minutes, the solid is filtered and rinsed with THF. The THF/H$_2$O filtrate is partially concentrated in a rotary evaporator at a temperature of less than 35° C. The aqueous concentrate is saturated with NaCl and extracted with 1500 ml of CH$_2$Cl$_2$. The organic phase is dried over MgSO$_4$, filtered and evaporated to dryness. The residue is taken up in 2000 mL of an H$_2$O/acetone (75/25) mixture, the insolubles are filtered, and rinsed with the H$_2$O/acetone (75/25) mixture. The filtrates are concentrated in a rotary evaporator at 50° C. and 20 mbar, and filtered again on sintered glass (porosity No. 4). The aqueous phase is saturated with NaCl, extracted 3 times with CH$_2$Cl$_2$ (1000 mL, 500 mL and 250 mL). The organic phases are combined, dried over MgSO$_4$, filtered and evaporated to dryness to give 60 g of crude product which is dissolved in 250 mL of CH$_2$Cl$_2$. 30 g of silica are then added to the solution. After stirring for 15 min, the silica is filtered and rinsed twice with CH$_2$Cl$_2$ (250 mL and 100 mL). The filtrate is concentrated to dryness and dried at 1 mbar at 20° C. to give 54.8 g of expected product 30 (white solid).

$^1$H NMR (300 MHz, DMSO-d$_6$), δ(ppm): 5.85 (m, 1H); 5.35 (d, 1H); 5.25 (d, 1H); 4.80 (m, 1H); 4.69 (m, 1H); 4.43 (d, 1H); 4.22 (m, 1H); 3.40 (s, 3H); 1.49 (s, 3H); 1.30 (s, 3H).

Step 2: Preparation of (3R,4R,5S)-4-hydroxy-5-[(1R)-1-hydroxyprop-2-en-1-yl]-3-methoxydihydrofuran-2(3H)-one (31)

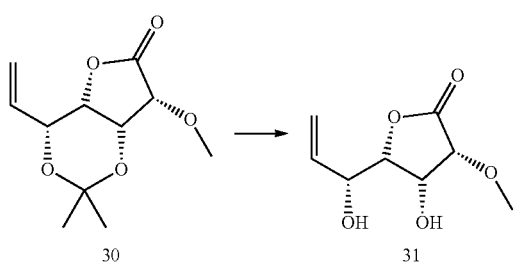

10 mL of TFA are added dropwise at 0° C. to a 100 mL round-bottomed flask containing 1.0 g of 30 (4.38 mmol), 10 mL of water and 14 mL of THF. The medium is allowed to return to RT and stirred overnight. The medium is then concentrated at reduced pressure at RT and 50 mL of water are added, and the mixture is frozen and freeze-dried. The freeze-dried product is impasted in heptane in the presence of a minimum amount of methanol, and after evaporation of the solvents, 778 mg of expected product 31 (white solid) are obtained.

MS: m/z=211 [M+Na]$^+$, 189 [M+H]$^+$ $^1$H NMR (400 MHz, DMSO-d$_6$), δ(ppm): 3.42 (s, 3H); 3.98 (dd, J=2.5 and 9.0 Hz, 1H); from 4.25 to 4.34 (m, 3H); 5.22 (dm, J=10.5 Hz, 1H); 5.29 (d, J=5.0 Hz, 1H); 5.44 (d partially masked, J=16.5 Hz, 1H); 5.46 (m, 1H); 5.97 (m, 1H).

Step 3: Preparation of (3R,4R,5S)-5-[(1R,2E)-3-cyclopentyl-1-hydroxyprop-2-en-1-yl]-4-hydroxy-3-methoxydihydrofuran-2(3H)-one (32)

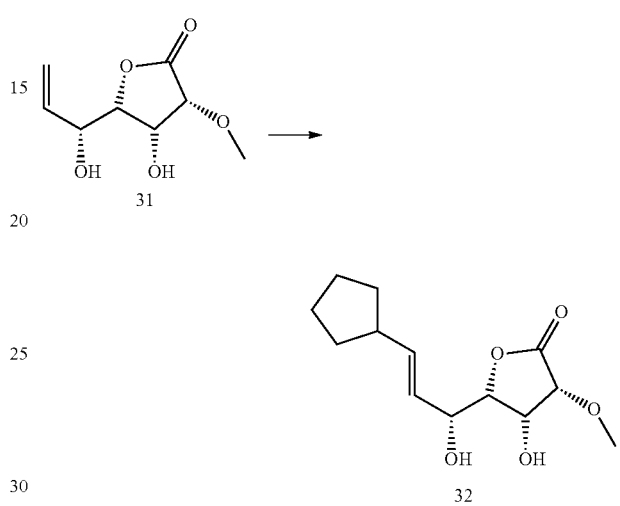

2 g of 31 (10.63 mmol), 4.22 g of vinylcyclopentane (43.92 mmol), 80 mL of CH$_2$Cl$_2$ and 226 mg of 2nd generation Grubb's catalyst (C46H65Cl2N2PRu, MW 848.98, 0.266 mmol) are added to a 250 mL round-bottomed flask. The medium is stirred for 2 h at RT and then heated for 4 h at 45° C. The insoluble material is filtered and then the solvent is evaporated and the crude product (3.39 g) is chromatographed on a silica cartridge (150 g), eluting with a heptane/AcOEt (50/50) mixture. 1.39 g of expected product 32 (white solid) are obtained.

MS: m/z=279 [M+Na]$^+$, 257 [M+H]$^+$ $^1$H NMR (300 MHz, DMSO-d$_6$), δ(ppm): 0.81 (t, J=7.5 Hz, 6H); 1.23 (m, 4H); from 1.32 to 1.49 (m, 2H); 1.78 (m, 1H); 3.42 (s, 3H); 3.97 (d, J=9.0 Hz, 1H); 4.20 to 4.31 (m, 3H); 5.11 to 5.75 (m, 4H).

Step 4: Preparation of (2R,3R,4S,5R,6E)-7-cyclopentyl-3,4,5-trihydroxy-2-methoxy-N-[(3S)-5-methyl-4-oxo-2,3,4,5-tetrahydro-1,5-benzoxazepin-3-yl]hept-6-enamide (Ex14)

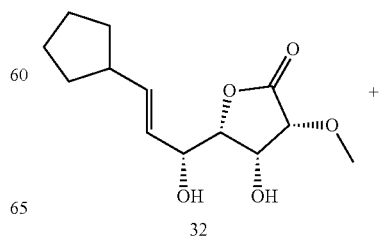

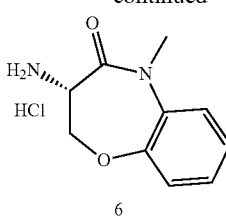

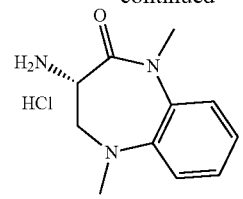

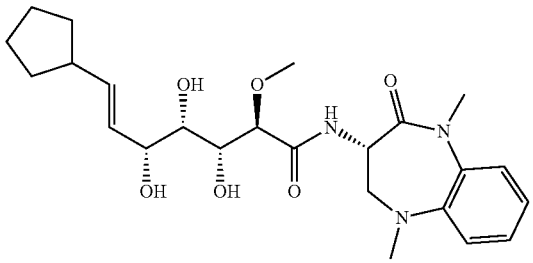

1.9 g of 32 (7.41 mmol), 1.7 g of 6 (7.41 mmol) and 2.59 g of sodium 2-ethylhexanoate (15.57 mmol) in 15.0 mL of THF are successively introduced into a 100 mL round-bottomed flask, with stirring and under an argon atmosphere. The stirring is maintained at RT for 88 h. 45 mL of AcOEt are added to the reaction medium. The medium is successively washed with 15 mL of water, 15 mL of an HCl solution (0.5N) and 10 mL of water. The organic phase is dried over anhydrous magnesium sulphate, filtered and then evaporated to dryness. The crude product is chromatographed on a silica cartridge (330 g, eluent, AcOEt/heptane: 90/10). 2.54 g of expected product Ex14 (white solid) are recovered.

[α]D: −101.8+/−1.7 c=1.775 mg/0.5 mL MeOH m.p.: 85+/−1° C.

Microanalysis: C=61.32% H=6.81% N=6.22%. C=61.48% H=7.25% N=6.27%

$^1$H NMR (400 MHz, DMSO-d$_6$), δ(ppm): 1.21 (m, 2H); from 1.42 to 1.76 (m, 6H); 2.38 (m, 1H); 3.20 (s, 3H); from 3.22 to 3.53 (m partially masked, 5H); 3.68 (d, J=8.0 Hz, 1H); 3.91 (m, 1H); from 4.22 to 4.40 (m, 4H); 4.54 (broad s, 1H); 4.71 (m, 1H); 5.35 (dd, J=7.0 and 16.0 Hz, 1H); 5.58 (dd, J=7.0 and 16.0 Hz, 1H); 7.22 (dd, J=2.0 and 7.5 Hz, 1H); from 7.25 to 7.35 (m, 2H); 7.49 (dd, J=2.0 and 7.5 Hz, 1H); 8.15 (d, J=8.0 Hz, 1H).

Ex15: (2R,3R,4S,5R,6E)-7-cyclopentyl-N-[(3S)-1,5-dimethyl-2-oxo-2,3,4,5-tetrahydro-1H-1,5-benzodiazepin-3-yl]-3,4,5-trihydroxy-2-methoxyhept-6-enamide

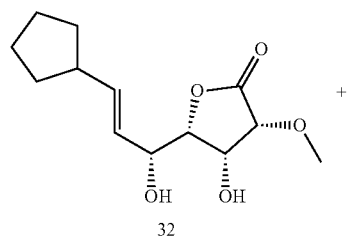

208 mg of 32 (852 μmol), 198 mg of 18 (0.712 mmol) and 473 mg of sodium 2-ethylhexanoate (2.848 mmol) in 5 mL of THF are successively introduced into a 25 mL round-bottomed flask, with stirring and under an argon atmosphere. The stirring is maintained at RT for 2 days. The mixture is concentrated under vacuum. The crude product is chromatographed on a silica cartridge [50 g, eluent AcOEt/AcOEt-isopropanol (50/50), in an AcOEt-isopropanol (50/50) gradient: 0 to 30%]). 172 mg of expected product Ex15 are recovered.

ES: 462 [M+H]$^+$ $^1$H NMR (400 MHz, DMSO-d$_6$), δ(ppm): 1.21 (m, 2H); from 1.45 to 1.77 (m, 6H); 2.39 (m, 1H); 2.71 (s, 3H); 3.11 (dd, J=7.5 and 10.0 Hz, 1H); 3.21 (s, 3H); 3.24 (s, 3H); 3.30 (m partially masked, 1H); 3.38 (dd, J=10.0 and 12.0 Hz, 1H); 3.49 (m, 1H); 3.69 (d, J=8.0 Hz, 1H); 3.92 (m, 1H); 4.29 (d, J=7.5 Hz, 1H); 4.32 (d, J=6.0 Hz, 1H); 4.41 (m, 1H); 4.54 (d, J=4.0 Hz, 1H); 5.36 (dd, J=7.0 and 16.0 Hz, 1H); 5.58 (dd, J=7.0 and 16.0 Hz, 1H); from 7.11 to 7.19 (m, 2H); 7.28 (dt, J=1.5 and 7.5 Hz, 1H); 7.38 (dd, J=1.5 and 7.5 Hz, 1H); 8.04 (d, J=8.0 Hz, 1H).

Ex16: (2R,3R,4S,5R,6E)-7-cyclopentyl-3,4,5-trihydroxy-2-methoxy-N-[(3S)-4-oxo-9-phenyl-2,3,4,5-tetrahydro-1,5-benzoxazepin-3-yl]hept-6-enamide

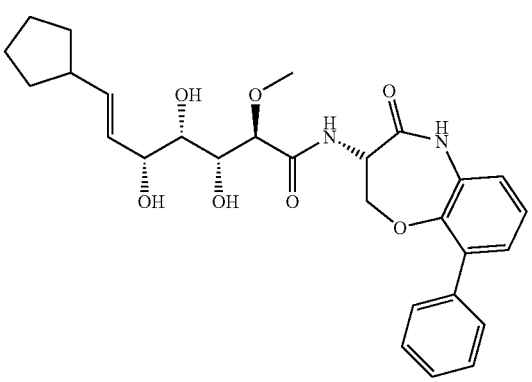

Step 1: Preparation of O-(2-bromo-6-nitrophenyl)-N-(tert-butoxycarbonyl)-L-serine (34)

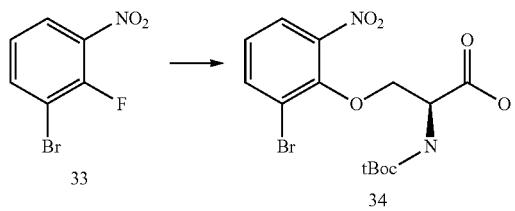

2.00 g of sodium hydride in suspension at 60% in oil (50 mmol) are added in portions, at 0° C., to a 1 L three-necked flask containing 250 ml of DMF and 5.0 g of L-Boc-Serine (24.37 mmol). The mixture is stirred at RT for 4 h. Next, this solution is slowly transferred, at 0° C., to a three-necked flask containing 250 ml of DMF and 5.90 g of 2-fluoro-3-bromonitrobenzene 33 (26.81 mmol). The reaction medium is allowed to return to RT and stirred overnight. 1 L of AcOEt is added and the mixture is washed twice with 500 mL of water saturated with citric acid. The organic phase is dried over MgSO$_4$, filtered and finally evaporated to dryness. The crude product is chromatographed on a silica cartridge (600 g, eluent CH$_2$Cl$_2$/MeOH, in an MeOH gradient: 0.5 to 10%). 4.5 g of expected product 34 (yellow oil) are obtained.

$^1$H NMR (400 MHz, DMSO-d$_6$), δ(ppm): 1.40 (s, 9H); 4.35 (broad s, 3H); 6.93 (broad d, J=8.0 Hz, 1H); 7.32 (t, J=8.0 Hz, 1H); 7.95 (m, 1H); 8.01 (dd, J=1.5 and 8.0 Hz, 1H); 13.0 (broad m, 1H)

Step 2: Preparation of N-(tert-butoxycarbonyl)-O-(3-nitrobiphenyl-2-yl)-L-serine (35)

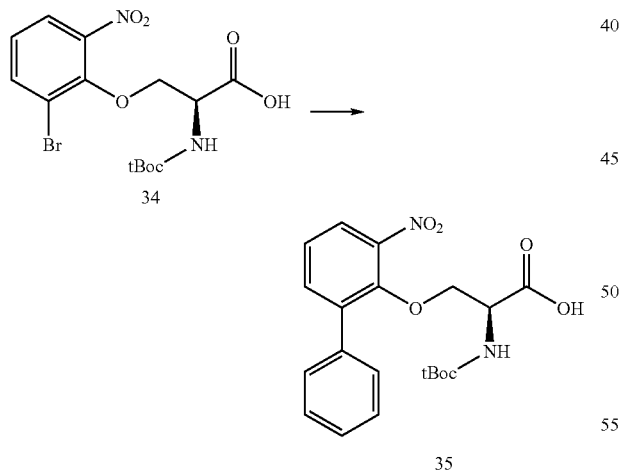

331 mg of phenylboronic acid (2.72 mmol), 50.3 mg of 1,1'-bis(diphenylphosphino)ferrocenepalladium chloride (C$_{35}$H$_{30}$Cl$_4$FeP$_2$Pd, MW 816.65, 0.025 mmol) and 3.22 g of caesium carbonate (9.87 mmol) are introduced into a 100 mL round-bottomed flask, with stirring and under an argon atmosphere, containing 16 mL of water, 5 mL of dioxane and 1 g of 34 (2.47 mmol). The medium is heated at 100° C., with stirring, for 1 h. The dioxane is concentrated and the aqueous phase is acidified to pH 2-3, extracted twice with 50 ml of AcOEt. The combined organic phases are dried over MgSO4, filtered and evaporated to dryness. The crude product is chromatographed on a silica cartridge (150 g, eluent CH$_2$Cl$_2$/MeOH, in an MeOH gradient: 1 to 5%). 500 mg of expected product 35 (yellow oil) are recovered.

$^1$H NMR (400 MHz, DMSO-d$_6$), δ(ppm): 1.37 (s, 9H); 3.72 (dd, J=4.5 and 9.0 Hz, 1H); 3.84 (dd, J=6.0 and 9.0 Hz, 1H); 4.00 (m, 1H); 6.41 (d, J=8.5 Hz, 1H); from 7.38 to 7.52 (m, 4H); 7.56 (broad d, J=8.0 Hz, 2H); 7.68 (dd, J=1.5 and 8.0 Hz, 1H); 7.88 (dd, J=1.5 and 8.0 Hz, 1H); 12.75 (broad m, 1H).

Step 3: Preparation of O-(3-aminobiphenyl-2-yl)-N-(tert-butoxycarbonyl)-L-serine (36)

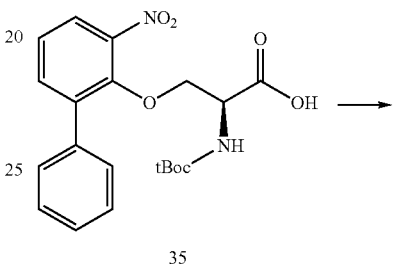

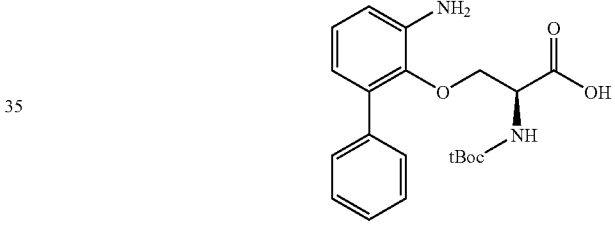

In an autoclave containing 500 mg of 35 (1.243 mmol), 54 mg of Pd/C (10%) and 33 mL of EtOH, hydrogenation is performed at 2 bar for 10 h at 20° C. After filtration of the catalyst on celite, the solvent is evaporated and 284 mg of expected product 36 are obtained, which product is used directly for the next step.

Step 4: Preparation of tert-butyl [(3S)-4-oxo-9-phenyl-2,3,4,5-tetrahydro-1,5-benzoxazepin-3-yl]carbamate (37)

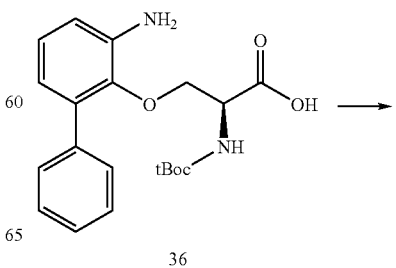

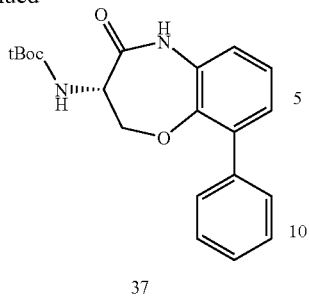

37

0.136 ml of diethyl cyanophosphonate (147.8 mg, 0.906 mmol) is introduced, at 0° C., into a 25 mL three-necked flask containing 284 mg of 36 (0.763 mmol) and 6.2 mL of DMF, followed 10 minutes later by 0.102 ml of TEA (0.731 mmol). The reaction medium is stirred at 0° C. for 2 h. 20 ml of AcOEt are added and then the mixture is washed with twice 20 mL of distilled water. The organic phase is dried over MgSO₄, filtered and then evaporated to dryness. 160 mg of expected product 37 are obtained.

ES: m/z=353 (M-H⁺)

¹H NMR (400 MHz, DMSO-d₆), δ(ppm): 1.37 (s, 9H); from 4.12 to 4.28 (m, 2H); 4.43 (m, 1H); 7.04 (d, J=8.5 Hz, 1H); 7.10 (dd, J=2.0 and 8.0 Hz, 1H); 7.16 (dd, J=2.0 and 8.0 Hz, 1H); 7.22 (t, J=8.0 Hz, 1H); from 7.33 to 7.51 (m, 5H); 9.97 (s, 1H).

Step 4: Preparation of (3S)-3-amino-9-phenyl-2,3-dihydro-1,5-benzoxazepin-4(5H)-one hydrochloride (38)

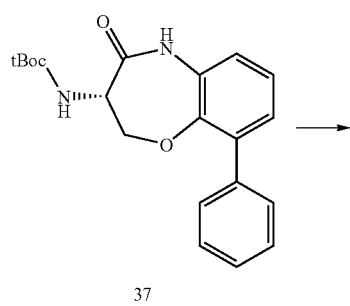

37

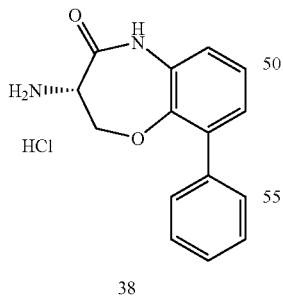

38

3.4 mL of a solution of hydrochloric acid in dioxane (4M) are added to a 25 mL round-bottomed flask containing 160 mg of 37 (0.452 mmol). The mixture is stirred for 4 h at RT under argon. The dioxane is concentrated, and taken up in 15 mL of isopropyl ether. The solid formed is disintegrated. 113 mg of amine 38 (cream-coloured solid) are obtained after filtration in hydrochloride form.

¹H NMR (400 MHz, DMSO-d₆), δ(ppm): from 4.31 to 4.51 (m, 3H); 7.15 (dd, J=2.0 and 8.0 Hz, 1H); 7.19 (dd, J=2.0 and 8.0 Hz, 1H); 7.26 (t, J=8.0 Hz, 1H); from 7.35 to 7.52 (m, 5H); 8.52 (broad s, 3H); 10.55 (s, 1H).

Step 5: Preparation of (2R,3R,4S,5R,6E)-7-cyclopentyl-3,4,5-trihydroxy-2-methoxy-N-[(3S)-4-oxo-9-phenyl-2,3,4,5-tetrahydro-1,5-benzoxazepin-3-yl] hept-6-enamide (Ex16)

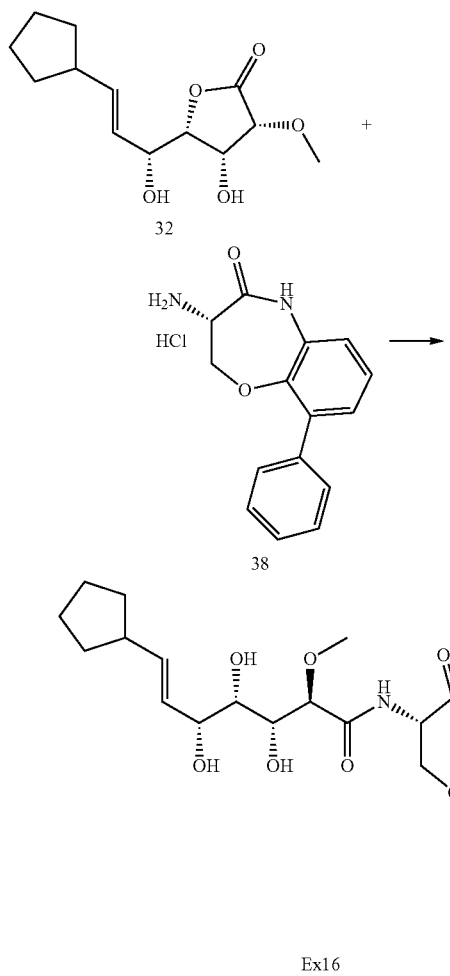

100 mg of 32 (390 μmol), 113 mg of 38 (390 μmol) and 162 mg of sodium 2-ethylhexanoate (0.98 mmol) in 2 mL of THF are successively introduced into a Wheaton tube, with stirring and under an argon atmosphere. The stirring is maintained at RT for 24 h. The reaction medium is concentrated to dryness. The residues are chromatographed on a silica cartridge (8 g, eluent AcOEt). 79 mg of expected product Ex16 are recovered.

MS: m/z=533 [M+Na]⁺, 511 [M+H]⁺

¹H NMR (400 MHz, DMSO-d₆), δ(ppm): 1.21 (m, 2H); from 1.42 to 1.77 (m, 6H); 2.38 (m, 1H); 3.21 (s, 3H); from 3.25 to 3.35 (m masked, 1H); 3.50 (m, 1H); 3.69 (d, J=8.0 Hz, 1H); 3.91 (m, 1H); from 4.15 to 4.33 (m, 4H); 4.52 (d, J=4.5 Hz, 1H); 4.79 (m, 1H); 5.35 (dd, J=7.0 and 16.0 Hz, 1H); 5.59 (dd, J=8.0 and 16.0 Hz, 1H); 7.11 (dd, J=2.0 and 7.5 Hz, 1H); 7.19 (dd, J=2.0 and 7.5 Hz, 1H); 7.23 (t, J=7.5 Hz, 1H); 7.39 (m, 1H); from 7.41 to 7.51 (m, 4H); 8.11 (d, J=8.0 Hz, 1H); 10.1 (s, 1H).

Ex17: (2R,3R,4S,5R,6E)-7-cyclopentyl-3,4,5-trihydroxy-2-methoxy-N-[(3S)-4-oxo-6-phenyl-2,3,4,5-tetrahydro-1,5-benzoxazepin-3-yl]hept-6-enamide

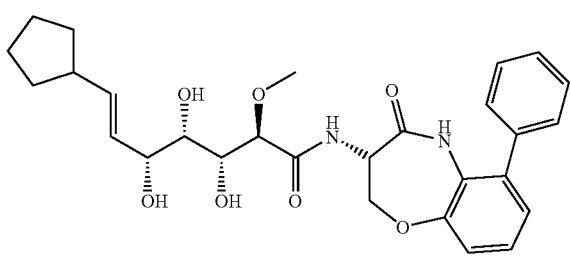

Step 1: Preparation of 3-fluoro-2-nitrobiphenyl (40)

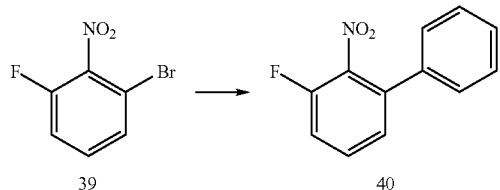

1.1 g of phenylboronic acid (9.0 mmol), 167 mg of 1,1'-bis(diphenylphosphino)ferrocenepalladium chloride (C35H30Cl4FeP2Pd, MW 816.65, 0.025 mmol) and 10.7 g of caesium carbonate (32.7 mmol) are introduced into a 250 mL round-bottomed flask, with stirring under an argon atmosphere, containing 54 mL of water, 18 mL of dioxane and 1.8 g of 39 (8.18 mmol). The medium is heated at 100° C., with stirring, for 1 h. The dioxane is concentrated, and extracted twice with 50 ml of AcOEt. The combined organic phases are dried over MgSO4, filtered and evaporated to dryness. 1.34 g of expected product 40 (yellow oil) are obtained.

$^1$H NMR (300 MHz, DMSO-$d_6$), δ(ppm): 7.40 (m, 2H); from 7.42 to 7.56 (m, 4H); 7.66 (dt, J=2.0 and 9.0 Hz, 1H); 7.78 (dt, J=6.0 and 9.0 Hz, 1H).

Step 2: Preparation of N-(tert-butoxycarbonyl)-O-(2-nitrobiphenyl-3-yl)-L-serine (41)

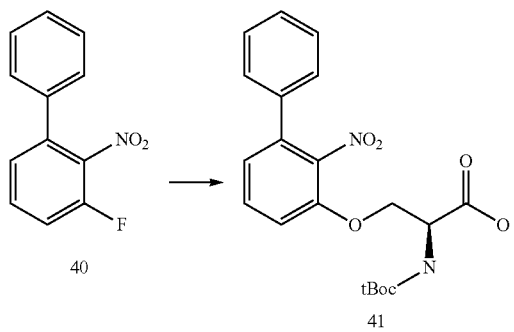

0.735 g of sodium hydride in suspension at 60% in oil (18.4 mmol) is added in portions to a 250 mL three-necked flask containing 64 ml of DMF and 1.26 g of L-Boc-Serine (6.12 mmol), at 0° C. The mixture is stirred for 1 h in the cold state and then for 2 h at RT. Next, the mixture is cooled to 0° C., and a solution of 40 (1.33 g 6.12 mmol) in 50 ml of DMF is added dropwise. The reaction medium is allowed to return to RT and it is stirred overnight. 250 mL of AcOEt are added, and the mixture is washed twice with 250 mL of a saturated aqueous citric acid solution. The organic phase is dried over MgSO4, filtered and finally evaporated to dryness. The crude product is chromatographed on a silica cartridge (150 g, eluent CH2Cl2/MeOH, in an MeOH gradient: 0.5 to 5%). 280 mg of expected product 41 (yellow oil) are obtained.

$^1$H NMR (400 MHz, DMSO-$d_6$), δ(ppm): 1.38 (s, 9H); from 4.28 to 4.49 (m, 3H); 7.03 (broad d, J=80, Hz, 1H); 7.11 (broad d, J=8.0 Hz, 1H); 7.32 (m, 2H); 7.38 (broad d, J=8.0 Hz, 1H); from 7.40 to 7.52 (m, 3H); 7.60 (t, J=8.0 Hz, 1H); 13.05 (broad m, 1H).

Step 3: Preparation of O-(2-aminobiphenyl-3-yl)-N-(tert-butoxycarbonyl)-L-serine (42)

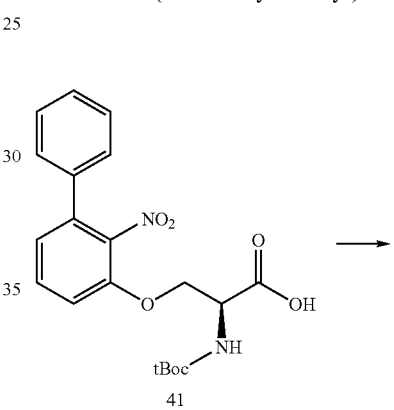

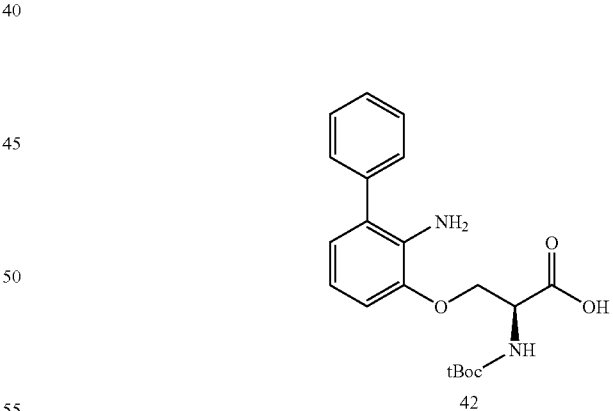

In an autoclave containing 280 mg of 41 (0.696 mmol), 30 mg of Pd/C (10%) and 18 mL of MeOH, hydrogenation is performed at 2 bar for 10 h at 20° C. After filtration of the catalyst on celite, the solvent is evaporated and 260 mg of expected product 42 are obtained, which product is used directly for the next step.

Step 4: Preparation of tert-butyl [(3S)-4-oxo-6-phenyl-2,3,4,5-tetrahydro-1,5-benzoxazepin-3-yl]carbamate (43)

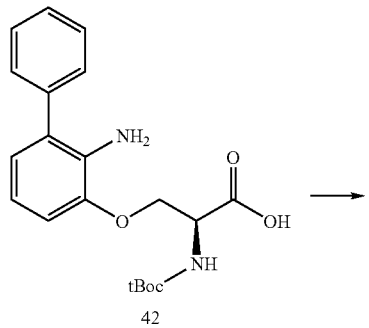

42

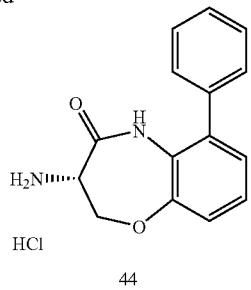

44

2 mL of dioxane and 1.8 mL of a solution of hydrochloric acid in dioxane (4M) are added to a 25 mL round-bottomed flask containing 85 mg of 43 (0.24 mmol). The mixture is stirred for 4 h at RT under argon. The dioxane is concentrated, and taken up in 10 mL of isopropyl ether. The solid formed is disintegrated with isopropyl ether. 60 mg of amine 44 (cream-coloured solid) are obtained after filtration in the hydrochloride form.

$^1$H NMR (300 MHz, DMSO-$d_6$), δ(ppm): from 4.32 to 4.65 (m, 3H); from 7.15 to 7.50 (m, 8H); 8.20 (broad m, 3H); 9.75 (s, 1H).

Step 5: Preparation of (2R,3R,4S,5R,6E)-7-cyclopentyl-3,4,5-trihydroxy-2-methoxy-N-[(3S)-4-oxo-6-phenyl-2,3,4,5-tetrahydro-1,5-benzoxazepin-3-yl]hept-6-enamide (Ex17)

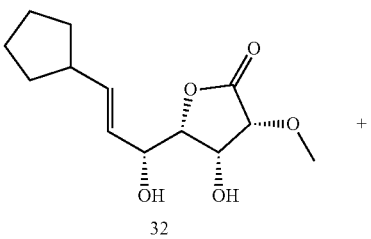

32

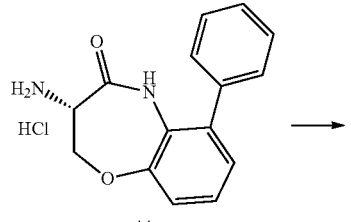

44

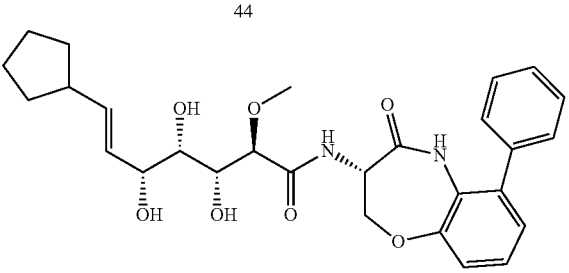

Ex17

53 mg of 32 (207 μmol), 60 mg of 44 (207 μmol), 86 mg of sodium 2-ethylhexanoate (0.52 mmol) in 1 mL of THF are successively introduced into a Wheaton tube, with stirring and under an argon atmosphere. The stirring is maintained at

43

0.143 ml of diethyl cyanophosphonate (156 mg, 0.96 mmol) is introduced, at 0° C., into a 25 mL three-necked flask containing 260 mg of 42 (0.70 mmol) and 6.5 mL of DMF, followed 10 minutes later by 0.109 ml of TEA (0.77 mmol). The reaction medium is stirred at 0° C. for 2 h. 25 ml of AcOEt are added and then the mixture is washed with twice 25 mL of distilled water. The organic phase is dried over MgSO$_4$, filtered and then evaporated to dryness. The crude product is chromatographed on a silica cartridge (24 g, eluent heptane/AcOEt, in an AcOEt gradient: 25 to 75%). 85 mg of expected product 43 are obtained.

ES: m/z=353 (M−H$^+$)

Step 4: Preparation of (3S)-3-amino-6-phenyl-2,3-dihydro-1,5-benzoxazepin-4(5H)-one hydrochloride (44)

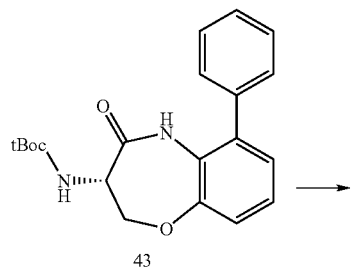

43

RT for 24 h. The reaction medium is concentrated to dryness. The residues are chromatographed on a silica cartridge (4 g, eluent AcOEt). 45 mg of expected product Ex17 (cream-coloured solid) are recovered.

MS: m/z=533 [M+Na]$^+$, 511 [M+H]$^+$ $^1$H NMR (400 MHz, DMSO-d$_6$), δ(ppm): 1.23 (m, 2H); from 1.43 to 1.75 (m, 6H); 2.39 (m, 1H); 3.23 (s, 3H); 3.52 (m, 1H); 3.71 (d, J=8.0 Hz, 1H); 3.93 (m, 1H); from 4.30 to 4.45 (m, 5H); 4.56 (d, J=4.5 Hz, 1H); 4.83 (m, 1H); 5.38 (dd, J=7.5 and 16.0 Hz, 1H); 5.59 (dd, J=8.5 and 16.0 Hz, 1H); from 7.18 to 7.25 (m, 2H); 7.31 (t, J=7.5 Hz, 1H); from 7.36 to 7.50 (m, 5H); 8.19 (d, J=8.0 Hz, 1H); 9.35 (s, 1H).

Ex18: (2R,3R,4S,5R,6E)-7-(2-bromophenyl)-3,4,5-trihydroxy-2-methoxy-N-[(3S)-5-methyl-4-oxo-2,3,4,5-tetrahydro-1,5-benzoxazepin-3-yl]hept-6-enamide

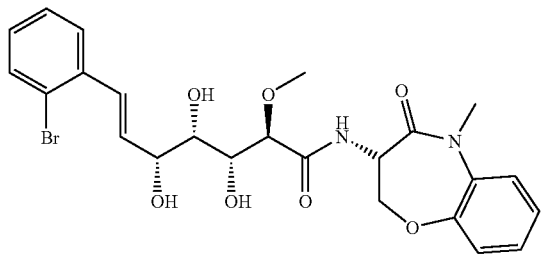

Step 1: Preparation of (3R,4R,5S)-5-[(1R,2E)-3-(2-bromophenyl)-1-hydroxyprop-2-en-1-yl]-4-hydroxy-3-methoxydihydrofuran-2(3H)-one (45)

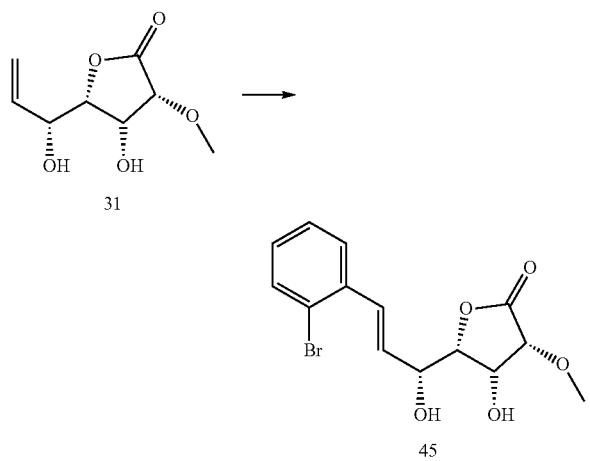

400 mg of 31 (2.13 mmol), 1.56 g of 2-bromostyrene (8.5 mmol), 1 mL of THF, 16 mL of CH$_2$Cl$_2$ and 54 mg of 2nd generation Grubb's catalyst (C46H65Cl2N2PRu, MW 848.98, 0.06 mmol) are added to a 100 mL round-bottomed flask. The medium is stirred for 24 h at RT. The solvent is evaporated, the crude product (1.9 g) is chromatographed on a silica cartridge (90 g), eluting with a CH$_2$Cl$_2$/MeOH (95/5) mixture. 190 mg of expected product 45 are obtained.

$^1$H NMR (300 MHz, DMSO-d$_6$), δ(ppm): 3.42 (s, 3H); 4.10 (dd, J=3.0 and 8.5 Hz, 1H); 4.29 (d, J=4.5 Hz, 1H); 4.47 (m, 1H); 4.51 (m, 1H); 5.56 (d, J=4.5 Hz, 1H); 5.63 (d, J=5.0 Hz, 1H); 6.43 (dd, J=4.5 and 16.0 Hz, 1H); 7.08 (dd, J=1.5 and 16.0 Hz, 1H); 7.22 (dt, J=2.0 and 7.5 Hz, 1H); 7.39 (dt, J=2.0 and 7.5 Hz, 1H); 7.63 (dd, J=2.0 and 7.5 Hz, 1H); 7.69 (dd, J=2.0 and 7.5 Hz, 1H).

Step 2: Preparation of (2R,3R,4S,5R,6E)-7-(2-bromophenyl)-3,4,5-trihydroxy-2-methoxy-N-[(3S)-5-methyl-4-oxo-2,3,4,5-tetrahydro-1,5-benzoxazepin-3-yl]hept-6-enamide (Ex18)

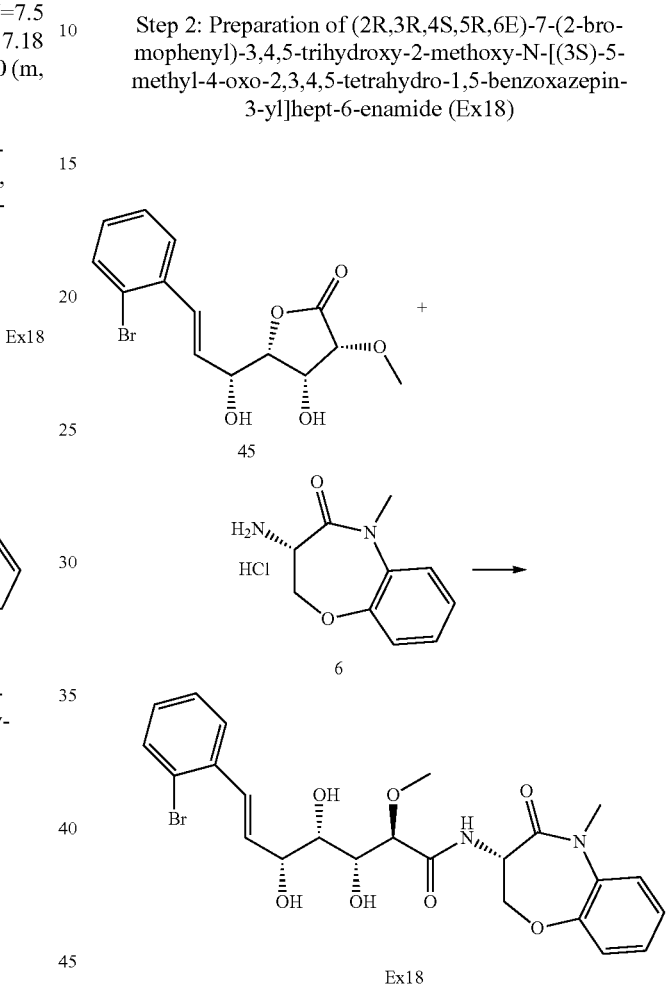

90 mg of 45 (0.22 mmol), 51 mg of 6 (0.22 mmol) and 93 mg of sodium 2-ethylhexanoate (0.56 mmol) in 2.0 mL of THF are successively introduced into a 10 mL round-bottomed flask, with stirring and under an argon atmosphere. The stirring is maintained at RT for 24 h. 20 mL of CH$_2$Cl$_2$ are added to the reaction medium. The mixture is successively washed with 10 mL of an HCl solution (1N), 10 mL of water saturated with NaCl. The organic phase is dried over anhydrous magnesium sulphate, filtered and then evaporated to dryness. The crude product is chromatographed on a silica cartridge (9 g, eluent, AcOEt/heptane:85/15). 49 mg of expected product Ex18 (white solid) are recovered.

ES: m/z=533 (M−H$^+$)

$^1$H NMR (400 MHz, DMSO-d$_6$), δ(ppm): 3.22 (s, 3H); from 3.23 to 3.32 (m partially masked, 3H); 3.48 (m, 1H); 3.59 (m, 1H); 3.72 (d, J=8.0 Hz, 1H); 4.22 (m, 1H); 4.32 (m, 2H); 4.45 (d, J=5.0 Hz, 1H); 4.57 (d, J=5.0 Hz, 1H); 4.71 (m, 1H); 4.99 (d, J=4.0 Hz, 1H); 6.33 (dd, J=6.0 and 16.0 Hz, 1H);

6.82 (d, J=16.0 Hz, 1H); from 7.22 to 7.39 (m, 5H); 7.48 (dd, J=2.0 and 7.5 Hz, 1H); from 7.55 to 7.64 (m, 2H); 8.16 (d, J=8.0 Hz, 1H).

Ex19: (2R,3R,4S,5R,6E)-3,4,5-trihydroxy-2-methoxy-N-[(3S)-5-methyl-4-oxo-2,3,4,5-tetrahydro-1,5-benzoxazepin-3-yl]-7-(3-thienyl)hept-6-enamide

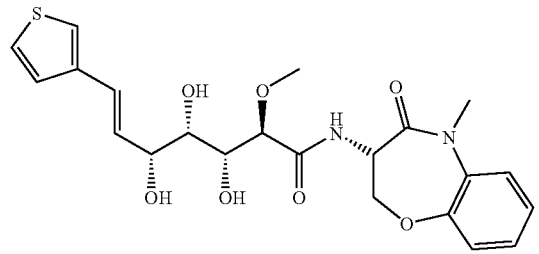

Step 1: Preparation of (3R,4R,5S)-4-hydroxy-5-[(1R,2E)-1-hydroxy-3-(3-thienyl)prop-2-en-1-yl]-3-methoxydihydrofuran-2(3H)-one (45)

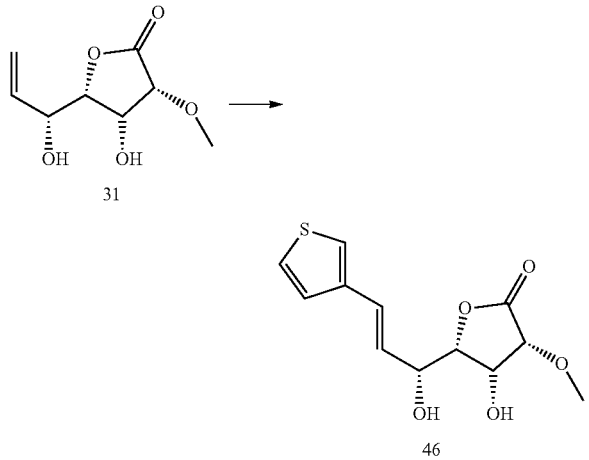

200 mg of 31 (1.06 mmol), 0.486 g of 3-vinylthiophene (4.4 mmol), 8 mL of CH$_2$Cl$_2$ and 27 mg of 2nd generation Grubb's catalyst (C46H65Cl2N2PRu, MW 848.98, 0.03 mmol) are added to a 50 mL round-bottomed flask. The medium is stirred for 24 h at RT, and then heated for 1 h at 40° C. The solvent is evaporated. The crude product is chromatographed on a silica cartridge (20 g, eluent, AcOEt/heptane: 65/35). 100 mg of expected product 46 are obtained.

ES: m/z=269 (M−H$^+$)

$^1$H NMR (400 MHz, DMSO-d$_6$), δ(ppm): 3.41 (s, 3H); 4.07 (dd, J=3.0 and 8.5 Hz, 1H); 4.28 (d, J=4.5 Hz, 1H); 4.39 (m, 1H); 4.42 (m, 1H); 5.40 (d, J=5.5 Hz, 1H); 5.48 (d, J=4.5 Hz, 1H); 6.20 (dd, J=5.0 and 16.0 Hz, 1H); 6.76 (broad d, J=16.0 Hz, 1H); 7.30 (broad d, J=5.0 Hz, 1H); 7.46 (broad d, J=3.0 Hz, 1H); 7.52 (dd, J=3.0 and 5.0 Hz, 1H).

Step 2: Preparation of (2R,3R,4S,5R,6E)-3,4,5-trihydroxy-2-methoxy-N-[(3S)-5-methyl-4-oxo-2,3,4,5-tetrahydro-1,5-benzoxazepin-3-yl]-7-(3-thienyl)hept-6-enamide (Ex19)

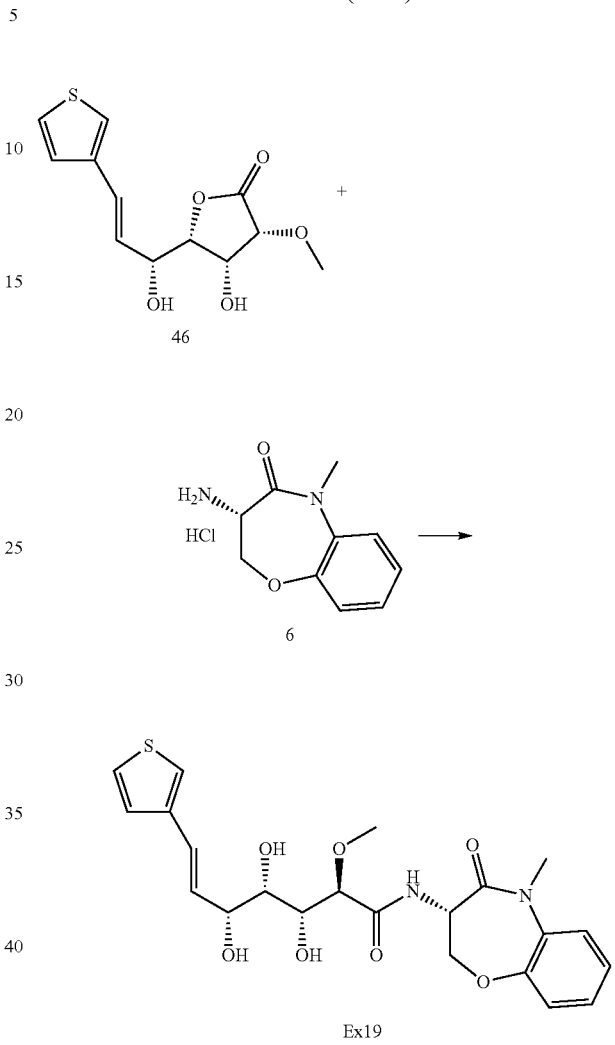

98 mg of 46 (0.36 mmol), 83 mg of 6 (0.36 mmol) and 151 mg of sodium 2-ethylhexanoate (0.91 mmol) in 1.5 mL of THF are successively introduced into a 10 mL round-bottomed flask, with stirring and under an argon atmosphere. The stirring is maintained at RT for 20 h. 20 mL of CH$_2$Cl$_2$ are added to the reaction medium. The mixture is successively washed with 10 mL of an HCl solution (1N) and 10 mL of water saturated with NaCl. The organic phase is dried over anhydrous magnesium sulphate, filtered and then evaporated to dryness. The crude product is chromatographed on a silica cartridge (20 g, eluent, CH$_2$Cl$_2$/isopropanol: 95/5). 67 mg of expected product Ex19 (powder) are recovered.

MS: m/z=485 [M+Na]$^+$, 463 [M+H]$^+$ $^1$H NMR (400 MHz, DMSO-d$_6$), δ(ppm): 3.22 (s, 3H); from 3.22 to 3.33 (m partially masked, 3H); 3.43 (m, 1H); 3.53 (m, 1H); 3.71 (d, J=8.0 Hz, 1H); 4.11 (m, 1H); 4.32 (m, 2H); 4.39 (d, J=7.0 Hz, 1H); 4.44 (d, J=6.0 Hz, 1H); 4.71 (m, 1H); 4.79 (d, J=4.0 Hz, 1H); 6.09 (dd, J=7.0 and 16.0 Hz, 1H); 6.53 (d, J=16.0 Hz, 1H); 7.21 (dd, J=2.0 and 7.5 Hz, 1H); from 7.22 to 7.34 (m, 3H); 7.39 (m, 1H); 7.49 (m, 2H); 8.14 (d, J=8.0 Hz, 1H).

Ex20: (2R,3R,4S,5R,6E)-7-cyclopentyl-2-ethoxy-3,4,5-trihydroxy-N-[(3S)-4-oxo-2,3,4,5-tetrahydro-1,5-benzoxazepin-3-yl]hept-6-enamide

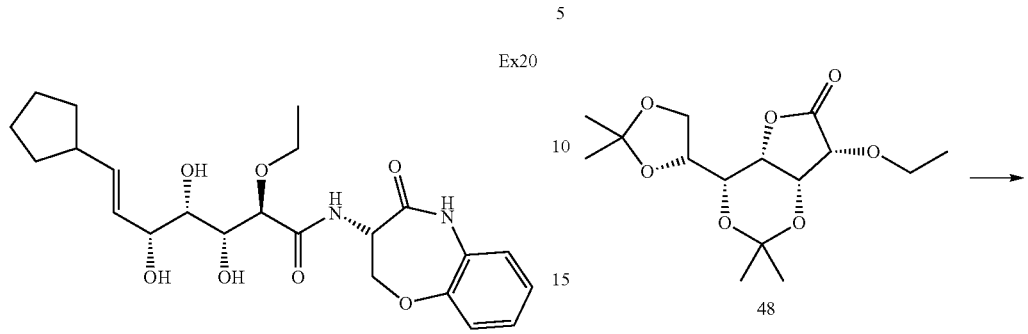

Step 1: Preparation of (4R,4aS,7R,7aR)-4-[(4R)-2,2-dimethyl-1,3-dioxolan-4-yl]-7-ethoxy-2,2-dimethyltetrahydro-6H-furo[3,2-d][1,3]dioxin-6-one (48)

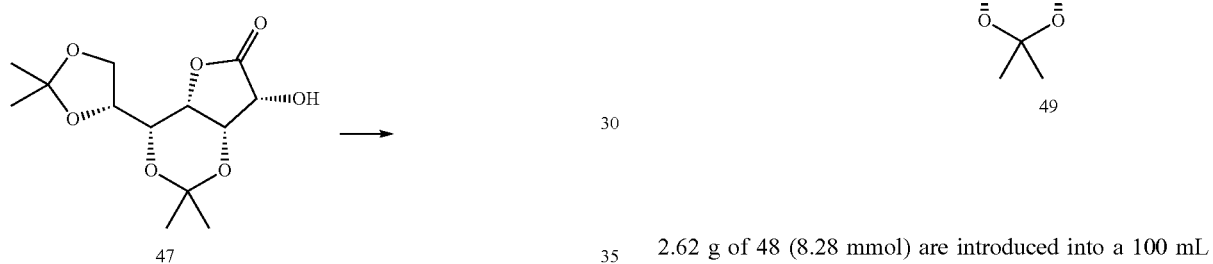

8 mL of iodoethane (15.44 g, 99 mmol), 9.7 g of silver oxide and 180 μl of water are added, at 0° C., to a 100 mL round-bottomed flask containing 24 mL of CH$_2$Cl$_2$ and 4.0 g of 47 (13.87 mmol) (which may be prepared according to the procedures described in Org. Process Res. Dev. 2003, 7(6), 856-865). The round-bottomed flask is immediately covered with aluminium. The reaction medium is allowed to return to RT and it is stirred for 24 h. The medium is diluted with 15 mL of CH$_2$Cl$_2$, and then the black precipitates are filtered. The filtrate is evaporated to dryness and then impasted in 20 mL of ethyl ether. After draining, washing with ether and drying under vacuum at 35° C., 2.64 g of expected product 48 are obtained.

MS: m/z=317 [M+H]$^+$

Step 2: Preparation of (4R,4aS,7R,7aR)-4-[(1R)-1,2-dihydroxyethyl]-7-ethoxy-2,2-dimethyltetrahydro-6H-furo[3,2-d][1,3]dioxin-6-one (49)

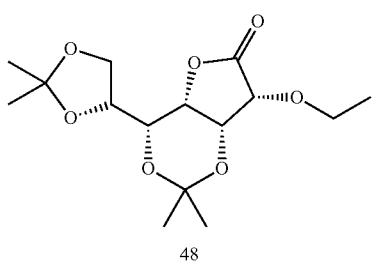

2.62 g of 48 (8.28 mmol) are introduced into a 100 mL three-necked flask containing 16 mL of water and 16 mL of acetic acid. The medium is stirred for 24 h at RT and then the reaction medium is concentrated under vacuum. The residues are disintegrated with 25 mL of isopropyl ether, filtered and dried under vacuum. 2.15 g of expected product 49 (white solid) are obtained.

MS: m/z=299 [M+Na]$^+$, 277 [M+H]$^+$ $^1$H NMR (400 MHz, DMSO-d$_6$), δ(ppm): 1.15 (t, J=7.0 Hz, 3H); 1.25 (s, 3H); 1.41 (s, 3H); 3.35 (m, 1H); from 3.48 to 3.73 (m, 4H); 3.92 (dd, J=2.0 and 9.0 Hz, 1H); 4.37 (t, J=2.0 Hz, 1H); 4.40 (t, J=6.0 Hz, 1H); 4.58 (d, J=4.0 Hz, 1H); 4.74 (dd, J=2.0 and 4.0 Hz, 1H); 4.91 d, J=6.0 Hz, 1H).

Step 3: Preparation of (4R,4aS,7R,7aR)-7-ethoxy-2,2-dimethyl-4-vinyltetrahydro-6H-furo[3,2-d][1,3]dioxin-6-one (50)

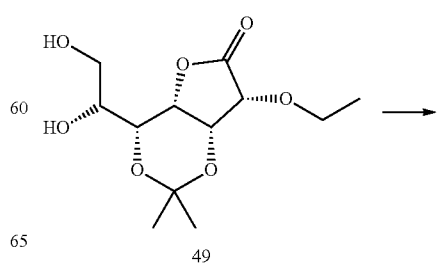

-continued

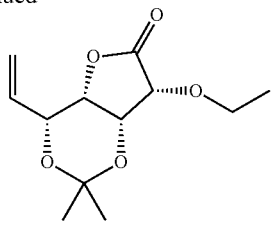

50

2.12 g of imidazole (31.13 mmol) and 10.37 g of triphenylphosphine supported by a styrene copolymer (Fluka, cas: 39319-11-4, 31.13 mmol) are added to a 250 mL three-necked flask containing 2.15 g of 49 (7.78 mmol) and 100 mL of toluene, with stirring and under an argon atmosphere. The medium is heated to the reflux temperature, and 5.93 g of iodine (23.35 mmol) are added in small portions. The heating is continued for 2 h, and then the mixture is cooled, the resin is filtered and washed with 20 mL of toluene and 50 mL of AcOEt. The filtrate is washed twice with 150 mL of a solution of water saturated with NaHCO$_3$. The organic phase is dried over anhydrous magnesium sulphate, filtered and then evaporated to dryness. The crude product is chromatographed on a silica cartridge (250 g, eluent CH$_2$Cl$_2$/MeOH— in a 0 to 10% MeOH gradient). 800 mg of expected product 50 are recovered.

MS: m/z=265 [M+Na]$^+$ $^1$H NMR (400 MHz, DMSO-d$_6$), δ(ppm): 1.14 (t, J=7.0 Hz, 3H); 1.30 (s, 3H); 1.48 (s, 3H); 3.59 (m, 1H); 3.69 (m, 1H); 4.21 (t, J=2.0 Hz, 1H); 4.52 (d, J=4.0 Hz, 1H); 4.68 (m, 1H); 4.77 (dd, J=2.0 and 4.0 Hz, 1H); 5.23 (td, J=2.0 and 10.5 Hz, 1H); 5.34 (td, J=2.0 and 17.0 Hz, 1H); 5.33 (m, 1H).

Step 4: Preparation of (3R,4R,5S)-3-ethoxy-4-hydroxy-5-[(1R)-1-hydroxyprop-2-en-1-yl]dihydrofuran-2(3H)-one (51)

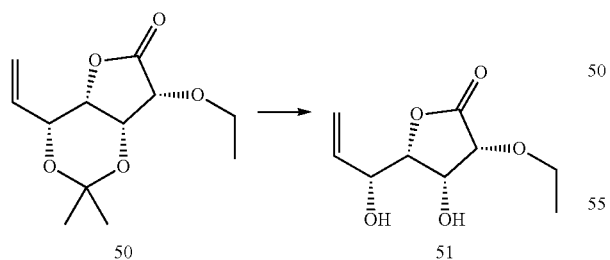

2.8 ml of TFA are added to a 25 mL round-bottomed flask containing 13 mL of water and 800 mg of 50 (3.30 mmol). The medium is stirred for 2 h at RT and then the medium is diluted with 200 mL of water, frozen and freeze-dried. 550 mg of expected product 51 (flaky white solid) are obtained.

$^1$H NMR (400 MHz, DMSO-d$_6$), δ(ppm): 1.18 (t, J=7.0 Hz, 3H); 3.64 (broad q, J=7.0 Hz, 2H); 3.98 dd, J=3.0 and 9.0 Hz, 1H); 4.29 (m, 2H); 4.36 (d, J=4.0 Hz, 1H); 5.21 (td, J=1.5 and 10.5 Hz, 1H); 5.29 (d, J=5.5 Hz, 1H); 5.42 (d, J=4.5 Hz, 1H); 5.43 (td, J=1.5 and 17.5 Hz, 1H); 5.96 (ddd, J=4.5-10.5 and 17.5 Hz, 1H).

Step 5: Preparation of (3R,4R,5S)-5-[(1R,2E)-3-cyclopentyl-1-hydroxyprop-2-en-1-yl]-3-ethoxy-4-hydroxydihydrofuran-2(3H)-one (52)

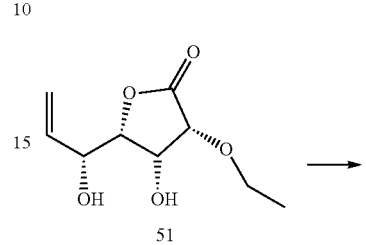

51

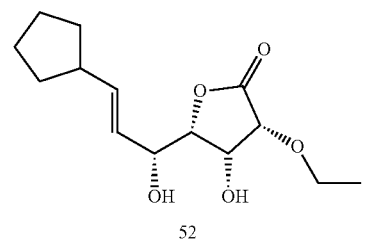

52

550 mg of 51 (2.47 mmol), 0.987 g of vinylcyclopentane (10.26 mmol), 18 mL of CH$_2$Cl$_2$ and 63 mg of 2nd generation Grubb's catalyst (C46H65Cl2N2PRu, MW 848.98, 0.030 mmol) are added to a 50 mL round-bottomed flask. The medium is stirred for 24 h at RT and then the insoluble material is filtered and the solvent is evaporated. The crude product is chromatographed on a silica cartridge (40 g, eluent AcOEt/heptane— in an AcOEt gradient: 50 to 100%). 85 mg of expected product 52 are obtained.

$^1$H NMR (500 MHz, DMSO-d$_6$), δ(ppm): 1.17 (t, J=7.0 Hz, 3H); 1.27 (m, 2H); from 1.47 to 1.79 (m, 6H); 2.44 (m, 1H); 3.62 (q, J=7.0 Hz, 2H); 3.95 (dd, J=2.5 and 9.0 Hz, 1H); from 4.20 to 4.28 (m, 2H); 4.33 (d, J=4.0 Hz, 1H); 5.17 (d, J=5.0 Hz, 1H); 5.35 (d, J=4.5 Hz, 1H); 5.49 (dd, J=5.5 and 16.0 Hz, 1H); 5.81 (dd, J=8.0 and 16.0 Hz, 1H).

Step 6: Preparation of (2R,3R,4S,5R,6E)-7-cyclopentyl-2-ethoxy-3,4,5-trihydroxy-N-[(3S)-4-oxo-2,3,4,5-tetrahydro-1,5-benzoxazepin-3-yl]hept-6-enamide (Ex20)

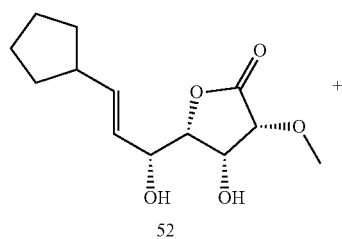

52

+

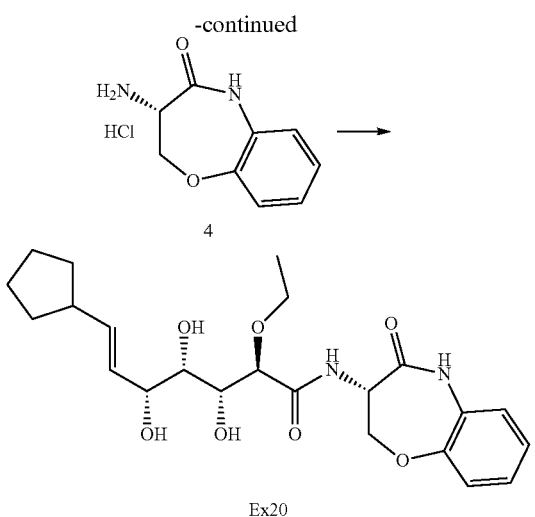

110 mg of 52 (407 µmol), 87 mg of 4 (407 µmol) and 169 mg of sodium 2-ethylhexanoate (1.02 mmol) in 2 mL of THF are successively introduced into a Wheaton tube, with stirring and under an argon atmosphere. The stirring is maintained at RT for 24 h. The reaction medium is concentrated to dryness. The residues are chromatographed on a silica cartridge (8 g, eluent AcOEt). 75 mg of expected product Ex20 are recovered.

MS: m/z=471 [M+Na]$^+$, 449 [M+H]$^+$ $^1$H NMR (400 MHz, DMSO-d$_6$), δ(ppm): 1.10 (t, J=7.0 Hz, 3H); 1.23 (m, 2H); from 1.43 to 1.77 (m, 6H); 2.39 (m, 1H); from 3.23 to 3.55 (m partially masked, 4H); 3.79 (d, J=8.0 Hz, 1H); 3.93 (m, 1H); from 4.23 to 4.40 (m, 4H); 4.55 (d, J=4.5 Hz, 1H); 4.69 (m, 1H); 5.39 (dd, J=7.0 and 16.0 Hz, 1H); 5.59 (dd, J=8.0 and 16.0 Hz, 1H); from 7.13 to 7.18 (m, 4H); 8.09 (d, J=8.0 Hz, 1H); 10.05 (s, 1H).

Biological Activity of the Products Prepared:

On the filing day of the application, it was calculated that the Caco2-TC7 of the product of Example 2 (Papp single point=52·10$^{-7}$ cm·sec$^{-1}$) is better than that of the product of Example 22a (Papp single point=6·10$^{-7}$ cm·sec$^{-1}$) described in Patent Application WO2006/056696.

The antiproliferative activity of the products of the examples of Table 1 was determined by measuring the inhibition of the cellular proliferation of HCT116 cells.

The cells are inoculated into a cell culture medium at a concentration of 10 000 cells per well, in 0.17 mL of medium, and 20 µL of product to be tested, at various concentrations, and 10 µL of thymidine [methyl-14C] (100 µCi/ml—specific activity 47.90 mCi/mmol; NEN Technologies reference NEC568 batch 3550-001) are added, and then the cells are incubated at 37° C. and 5% CO$_2$.

Medium used for the culture of HCT116 cells:DMEM medium 2 mM L-glutamine, 200 IU/ml penicillin, 200 µg/ml streptomycin and 10% (V/V) foetal calf serum (Life Technologies).

After 96 hours, the incorporation of $^{14}$C-thymidine is counted in a Microbeta Wallac Trilux 1450 liquid scintillation counter. The results R are expressed in cpm (counts per minute) and converted to percentage growth inhibition GI % by first subtracting the mean of the number of cpm of the wells without B cells and by then dividing by the number of cpm of the wells of the untreated cells C comprising 20 µL of medium for dilution of the product containing 1% ethanol. (GI %=(R−B)×100/C %).

The IC50 values are calculated with the aid of the equation 205 of the XLFit software (IDBS company, UK) by non-linear regression analysis using the Marquardt algorithm (Donald W. MARQUARDT, J. Soc. industry. appl, vol 11, No. 2, June, 1963).

The products of Table 1 exhibit an IC50 on the HCT116 cells generally less than 30 µM and preferably less than 100 nM. For example, the compound of Example 1 has an IC50 of 60 nM, the compound of Example 2 has an IC50 of 32 nM, the compound of Example 3 has an IC50 of 88 nM, the compound of Example 4 has an IC50 of 45 nM, the compound of Example 5 has an IC50 of 28 nM.

TABLE 1

| Example | Structure |
|---|---|
| Ex1 | 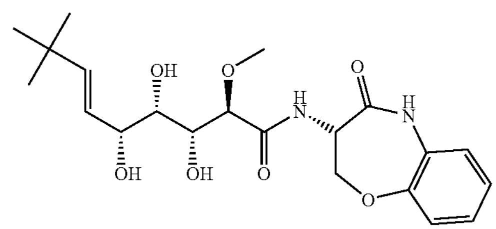 |
| Ex2 | 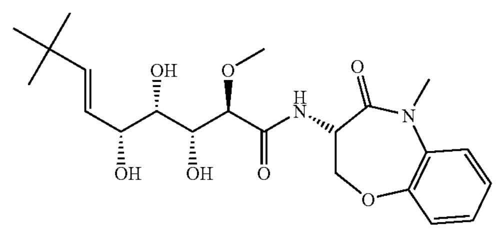 |
| Ex3 | 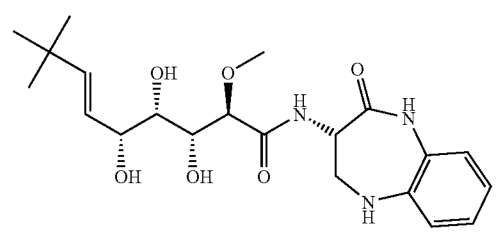 |
| Ex4 | 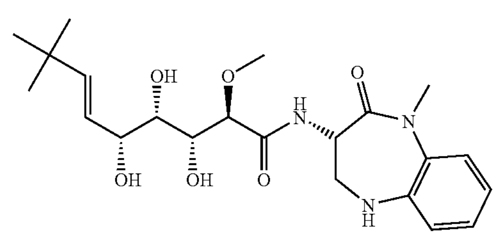 |
| Ex5 | 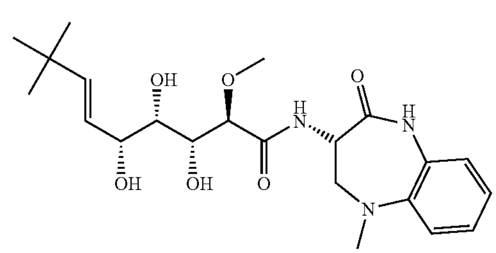 |

TABLE 1-continued

| Example | Structure |
|---|---|
| Ex6 | 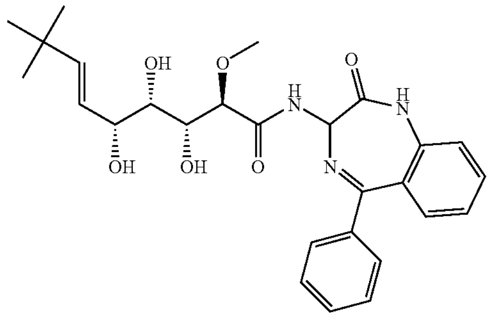 |
| Ex7 | 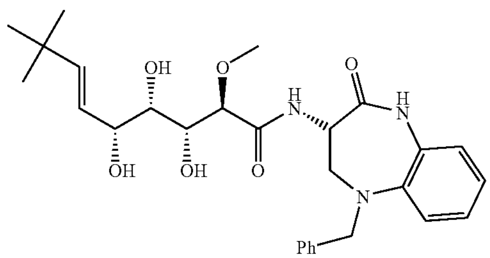 |
| Ex8 | 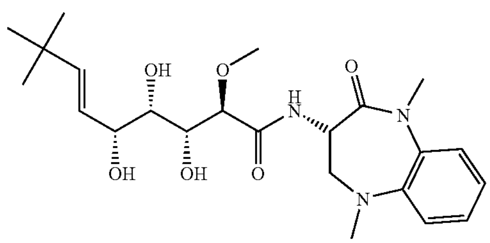 |
| Ex9 | 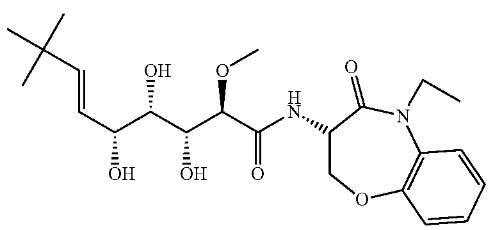 |
| Ex10 | 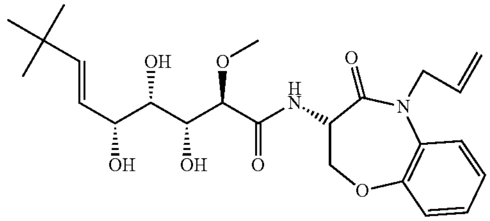 |
| Ex11 | 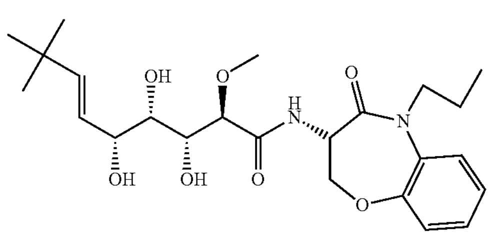 |
| Ex12 | |
| Ex13 | |
| Ex14 | |
| Ex15 | |
| Ex16 | |
| Ex17 | |

TABLE 1-continued

| Example | Structure |
|---|---|
| Ex18 | 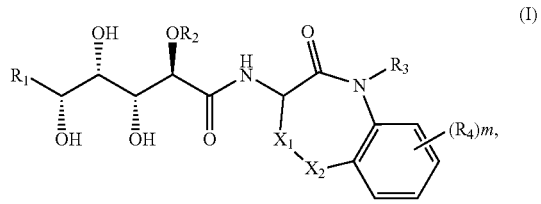 |
| Ex19 | 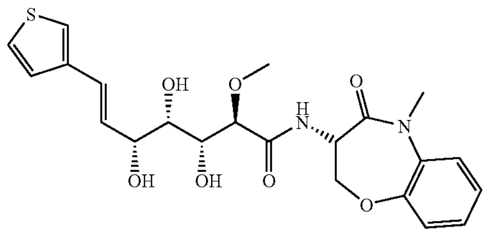 |
| Ex20 | 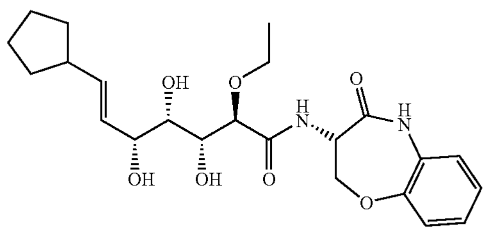 |

What is claimed is:

1. A compound of formula (I)

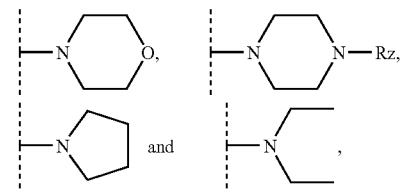

wherein:
a) $R_1$ is independently chosen from the group consisting of (C1-C12)alkyl, (C2-C12)alkenyl, (C2-C12)alkynyl, cycloalkyl, heterocyclyl, aryl, heteroaryl, cycloalkyl (C1-C12)alkyl, cycloalkyl(C2-C12)alkenyl, cycloalkyl (C2-C12)alkynyl, heterocyclyl(C1-C12)alkyl, heterocyclyl(C2-C12)alkenyl, heterocyclyl(C2-C12)alkynyl, aryl(C1-C12)alkyl, aryl(C2-C12)alkenyl, aryl(C2-C12) alkynyl, heteroaryl(C1-C12)alkyl, heteroaryl(C2-C12) alkenyl, and heteroaryl(C2-C12)alkynyl, the aryl group of each $R_1$ being optionally substituted with one or more halogens;
b) $R_2$ is chosen from the group consisting of (C1-C6)alkyl, aryl(C1-C6)alkyl, heteroaryl(C1-C6)alkyl, aryl, heteroaryl, (C1-C6)alkylthio(C1-C6)alkyl, di(C1-C6)alkylamino(C1-C6)alkyl, aryloxy(C1-C6)alkyl, and (C1-C6)alkoxy(C1-C6)alkyl;
c) $R_3$ is chosen from the group consisting of H, COO($R_5$), CONH($R_5$), CO($R_5$), O($R_5$), and $R_5$;
d) $R_4$ is independently chosen from the group consisting of H, F, Cl, Br, N($R_5$)$_2$, NO$_2$, CN, COO($R_5$), CON($R_5$)$_2$, NHCO($R_5$), NHCOO($R_5$), OCONH($R_5$), O($R_5$), and $R_5$ or alternatively two substituents $R_4$ linked to 2 adjacent carbons of the phenyl form together a ring chosen from cycloalkyl, heterocyclyl, aryl and heteroaryl, optionally substituted with one or more $R_4$;
e) $X_1$ is —CH$_2$—; $X_2$ is independently chosen from the group consisting of O, and N($R_5$), or alternatively, $X_1$ and $X_2$ form together a divalent group independently chosen from —N=C($R_5$)— and —N($R_5$)—C($R_5$) ($R_5$)—, it being possible for the two substituents $R_5$ to be identical or different;
f) m has the value 0, 1, 2, 3, or 4;
g) $R_5$ is independently chosen from non-bonding electron doublet, H, (C1-C12)alkyl, (C2-C12)alkenyl, (C2-C12) alkynyl, halo(C1-C12)alkyl, aryl(C1-C12)alkyl, heteroaryl(C1-C12)alkyl, heteroarylaryl(C1-C12)alkyl, aryl, heteroaryl and cycloalkyl, in which each $R_5$ is optionally substituted with at least one substituent chosen from OH, halogen, (C1-C4)alkyl, (C1-C4)alkoxy, aryl(C1-C4)alkyl, aryl, heteroaryl(C1-C4)alkyl, heteroaryl, —N(CH$_3$)$_2$, —NH$_2$, CONH$_2$, each of the Rz is independently chosen from the group consisting of H, COO($R_5$), CONH($R_5$), CON($R_5$)$_2$, CO($R_5$) and $R_5$, in which each $R_5$ is independently chosen from (C1-C4)alkyl, halo(C1-C4)alkyl, aryl(C1-C4) alkyl, and heteroaryl(C1-C4)alkyl, in which each $R_5$ is optionally substituted with one substituent chosen from OH, halogen, (C1-C4)alkyl, (C1-C4)alkoxy, aryl(C1-C4)alkyl, aryl, heteroaryl(C1-C4)alkyl and heteroaryl; or
a pharmaceutically acceptable acid addition salt of such compound, wherein heteroaryl is a monocyclic or polycyclic heteroaromatic substituent containing from 1 to 13 carbon atoms and from 1 to 4 heteroatoms selected from oxygen, sulphur, nitrogen and selenium, and
heterocyclyl is a saturated or partially unsaturated cyclic hydrocarbon based substituent containing from 1 to 13 carbon atoms and from 1 to 4 heteroatoms selected from oxygen, sulphur, nitrogen and selenium.

2. A compound according to claim 1 wherein $R_1$ is chosen from —C($R_6$)=C($R_7$)($R_8$) in which $R_6$, $R_7$, and $R_8$ are independently chosen from H, (C1-C6)alkyl, cycloalkyl, heterocyclyl, aryl and heteroaryl.

3. A compound according to claim 2 wherein $R_1$ is chosen from (E) —CH=CH—CH(CH$_3$)(C$_2$H$_5$), (E) —CH=CH—CH(CH$_3$)$_2$, and (E) —CH=CH—C(CH$_3$)$_3$.

4. A compound according to claim 2, wherein $R_1$ is chosen from (E) —C(CH$_3$)=CH—CH(CH$_3$)(C$_2$H$_5$), (E) —C(CH$_3$)=CH—CH(CH$_3$)$_2$, and (E) —C(CH$_3$)=CH—C(CH$_3$)$_3$.

5. A compound according to claim 1 wherein $R_2$ is methyl.
6. A compound according to claim 2 wherein $R_2$ is methyl.
7. A compound according to claim 1 wherein $R_3$ is H.
8. A compound according to claim 2 wherein $R_3$ is H.
9. A compound according to claim 1 wherein $R_3$ is methyl.
10. A compound according to claim 2 wherein $R_3$ is methyl.

11. A compound according to claim 1 wherein $X_1$ is —$CH_2$— and $X_2$ is O.

12. A compound according to claim 2 wherein $X_1$ is —$CH_2$— and $X_2$ is O.

13. A compound according to claim 1 wherein $X_1$ is —$CH_2$— and $X_2$ is N($R_5$) in which $R_5$ is H or methyl; or $X_1$ and $X_2$ form together a divalent group —N=C($R_5$)—where $R_5$ is phenyl.

14. A compound according to claim 2 wherein $X_1$ is —$CH_2$— and $X_2$ is N($R_5$) in which $R_5$ is H or methyl; or $X_1$ and $X_2$ form together a divalent group —N=C($R_5$)—where $R_5$ is phenyl.

15. A compound according to claim 1 which is:
N-((S)-8-oxo-6,7,8,9-tetrahydro-5-oxa-9-azabenzocyclohepten-7-yl)-(E)-(2R,3R,4S,5R)-3,4,5-trihydroxy-2-methoxy- 8,8-dimethylnon-6-enamide;
N-((S)-9-methyl-8-oxo-6,7,8,9-tetrahydro-5-oxa-9-azabenzocyclohepten-7-yl)-(E)-(2R,3R,4S,5R)-3,4,5-trihydroxy-2-methoxy-8,8-dimethylnon-6-enamide;
N-((S)-2-oxo-2,3,4,5-tetrahydro-1H-1,5-benzodiazepin-3-yl)-(E)-(2R,3R,4S,5R)-3,4,5-trihydroxy-2-methoxy-8,8-dimethylnon-6-enamide;
N-((S)-1-methyl-2-oxo-2,3,4,5-tetrahydro-1H-1,5-benzodiazepin-3-yl)-(E)-(2R,3R,4S,5R)-3,4,5-trihydroxy-2-methoxy-8,8-dimethylnon-6-enamide; or
N-((S)-1-methyl-4-oxo-2,3,4,5-tetrahydro-1H-1,5-benzodiazepin-3-yl)-(E)-(2R,3R,4S,5R)-3,4,5-trihydroxy-2-methoxy-8,8-dimethylnon-6-enamide; or
a pharmaceutically acceptable acid addition salt of such compound.

16. A compound according to claim 1 which is:
(2R,3R,4S,5R,6E)-N-[(3S)-1-benzyl-4-oxo-2,3,4,5-tetrahydro-1H-1,5-benzodiazepin-3-yl]-3,4,5-trihydroxy-2-methoxy-8,8-dimethylnon-6-enamide;
(2R,3R,4S,5R,6E)-N-[(3S)-1,5-dimethyl-2-oxo-2,3,4,5-tetrahydro-1H-1,5-benzodiazepin-3-yl]-3,4,5-trihydroxy-2-methoxy-8,8-dimethylnon-6-enamide;
(2R,3R,4S,5R,6E)-N-[(3S)-5-ethyl-4-oxo-2,3,4,5-tetrahydro-1,5-benzoxazepin-3-yl]-3,4,5-trihydroxy-2-methoxy-8,8-dimethylnon-6-enamide;
(2R,3R,4S,5R,6E)-N-[(3S)-5-allyl-4-oxo-2,3,4,5-tetrahydro-1,5-benzoxazepin-3-yl]-3,4,5-trihydroxy-2-methoxy-8,8-dimethylnon-6-enamide;
(2R,3R,4S,5R,6E)-3,4,5-trihydroxy-2-methoxy-8,8-dimethyl-N-[(3S)-4-oxo-5-propyl-2,3,4,5-tetrahydro-1,5-benzoxazepin-3-yl]non-6-enamide;
(2R,3R,4S,5R,6E)-3,4,5-trihydroxy-N-[(3S)-5-isopropyl-4-oxo-2,3,4,5-tetrahydro-1,5-benzoxazepin-3-yl]-2-methoxy-8,8-dimethylnon-6-enamide;
(2R,3R,4S,5R,6E)-N-[(3S)-5-(3,5-difluorobenzyl)-4-oxo-2,3,4,5-tetrahydro-1,5-benzoxazepin-3-y1]-3,4,5-trihydroxy-2-methoxy-8,8-dimethylnon-6-enamide;
(2R,3R,4S,5R,6E)-7-cyclopentyl-3,4,5-trihydroxy-2-methoxy-N-[(3S)-5-methyl-4-oxo-2,3,4,5-tetrahydro-1,5-benzoxazepin-3-yl]hept-6-enamide;
(2R,3R,4S,5R,6E)-7-cyclopentyl-N-[(3S)-1,5-dimethyl-2-oxo-2,3,4,5-tetrahydro-1H-1,5-benzodiazepin-3-yl]-3,4,5-trihydroxy-2-methoxyhept-6-enamide;
(2R,3R,4S,5R,6E)-7-cyclopentyl-3,4,5-trihydroxy-2-methoxy-N-[(3S)-4-oxo-9-phenyl-2,3,4,5-tetrahydro-1,5-benzoxazepin-3-yl]hept-6-enamide;
(2R,3R,4S,5R,6E)-7-cyclopentyl-3,4,5-trihydroxy-2-methoxy-N-[(3S)-4-oxo-6-phenyl-2,3,4,5-tetrahydro-1,5-benzoxazepin-3-yl]hept-6-enamide;
(2R,3R,4S,5R,6E)-7-(2-bromophenyl)-3,4,5-trihydroxy-2-methoxy-N-[(3S)-5-methyl-4-oxo-2,3 ,4,5-tetrahydro-1,5-b enzoxazepin-3 -yl]hept-6-enamide;
(2R,3R,4S,5R,6E)-3,4,5-trihydroxy-2-methoxy-N-[(3S)-5-methyl-4-oxo-2,3,4,5-tetrahydro-1,5-benzoxazepin-3-yl]-7-(3-thienyl)hept-6-enamide; or
(2R,3R,4S,5R,6E)-7-cyclopentyl-2-ethoxy-3,4,5-trihydroxy-N-[(3S)-4-oxo-2,3,4,5-tetrahydro-1,5-benzoxazepin-3-yl]hept-6-enamide, or
a pharmaceutically acceptable acid addition salt of such compound.

17. A compound according to claim 1 which is
a) in non-chiral form, or
b) in racemic form, or
c) in a form enriched with a stereoisomer, or
d) in a form enriched with an enantiomer;
and which is optionally salified.

18. A pharmaceutical composition comprising a compound according to claim 1 and at least one pharmaceutically acceptable excipient.

19. A pharmaceutical composition comprising a compound according to claim 15 and at least one pharmaceutically acceptable excipient.

20. A pharmaceutical composition comprising a compound according to claim 16 and at least one pharmaceutically acceptable excipient.

21. A process for preparing a compound according to claim (1) of formula (I) comprising the step of subjecting a compound of formula (II)

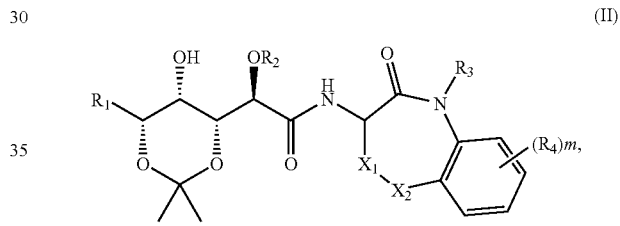

(II)

to hydrolysis so as to obtain a compound of formula (I).

22. A process according to claim 21, further comprising the step of reacting a compound of formula (III)

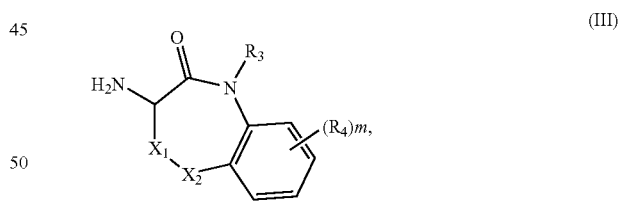

(III)

with a compound of formula (IV)

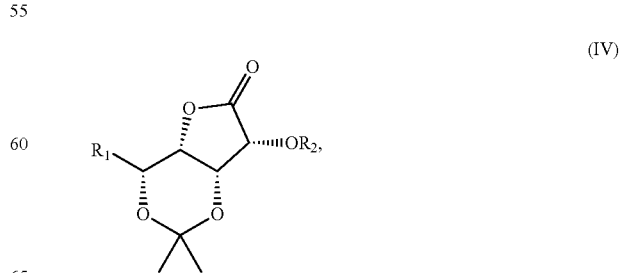

(IV)

in order to obtain a compound of formula (II).

23. A process for preparing a compound according to claim 1 of formula (I) comprising the step of reacting a compound of formula (III)

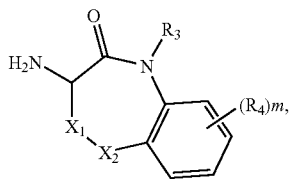
(III)

with a compound of formula (V)

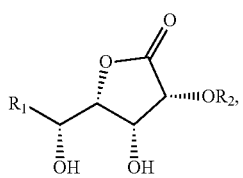
(V)

so as to obtain a compound of formula (I).

24. A method according to claim 23, further comprising the step of subjecting a compound of formula (IV)

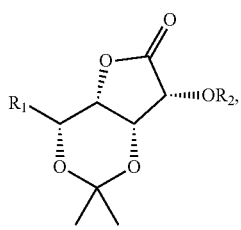
(IV)

to hydrolysis so as to obtain a compound of formula (V)

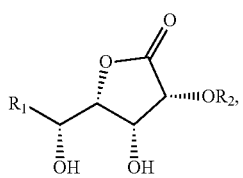
(V)

25. A method according to claim 23, further comprising the steps of subjecting a compound of formula (VII)

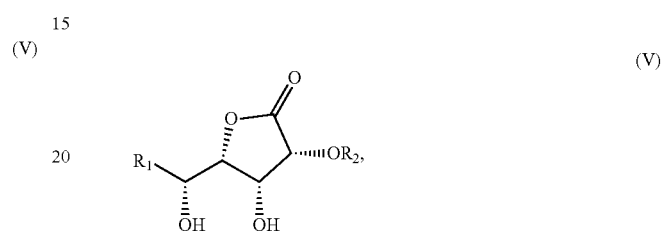
(VII)

to hydrolysis in order to obtain a compound of formula (VI)

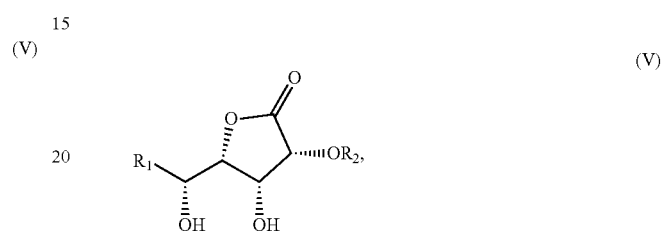
(VI)

and then subjecting to compound of formula (VI) to metathesis to obtain a compound of formula (V)

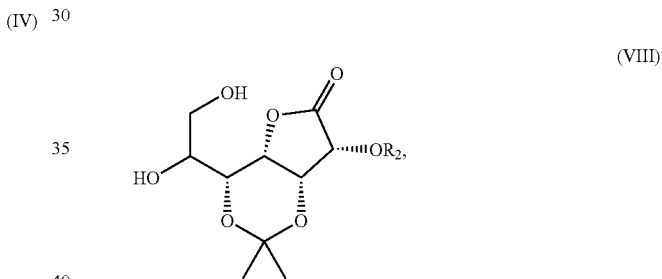
(V)

wherein $R_1$ is —CH═CH—$R'_1$ and $R'_1$ represents a (C1-C6)alkyl, cycloalkyl, heterocyclyl, aryl or heteroaryl group.

26. A process according to claim 25 further comprising the step of subjecting a compound of formula (VIII)

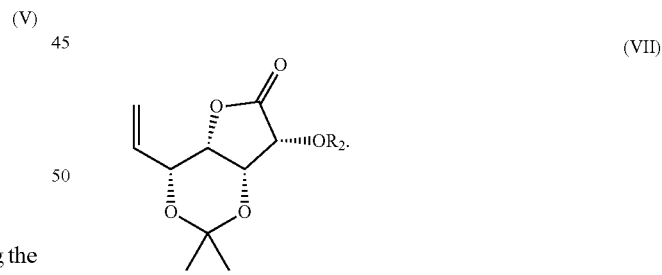
(VIII)

to a double dehydration in order to obtain a compound of formula (VII)

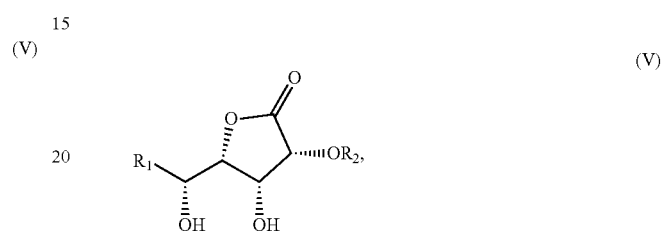
(VII)

27. A compound of formula (II)

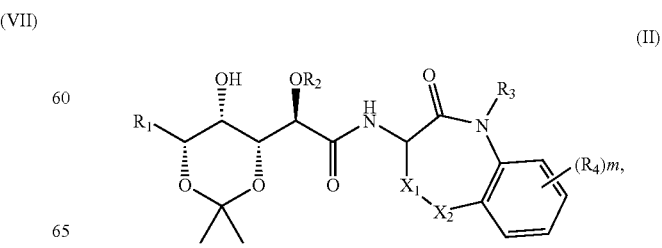
(II)

wherein:
R₁ is independently chosen from the group consisting of (C1-C12)alkyl, (C2-C12)alkenyl, (C2-C12)alkynyl, cycloalkyl, heterocyclyl, aryl, heteroaryl, cycloalkyl (C1-C12)alkyl, cycloalkyl(C2-C12)alkenyl, cycloalkyl (C2-C12)alkynyl, heterocyclyl(C1-C12)alkyl, heterocyclyl(C2-C12)alkenyl, heterocyclyl(C2-C12)alkynyl, aryl(C1-C12)alkyl, aryl(C2-C12)alkenyl, aryl(C2-C12) alkynyl, heteroaryl(C1-C12)alkyl, heteroaryl(C2-C12) alkenyl, and heteroaryl(C2-C12)alkynyl, the aryl group of each R₁ being optionally substituted with one or more halogens;

R₂ is chosen from the group consisting of (C1-C6)alkyl, aryl(C1-C6)alkyl, heteroaryl(C1-C6)alkyl, aryl, heteroaryl, (C1-C6)alkylthio(C1-C6)alkyl, di(C1-C6) alkylamino(C1-C6)alkyl, aryloxy(C1-C6)alkyl, and (C1-C6)alkoxy(C1-C6)alkyl;

R₃ is chosen from the group consisting of H, COO(R₅), CONH(R₅), CO(R₅), O(R₅), and R₅;

R₄ is independently chosen from the group consisting of H, F, Cl, Br, N(R₅)₂, NO₂, CN, COO(R₅), CON(R₅)₂, NHCO(R₅), NHCOO(R₅), OCONH(R₅), O (R₅), and R₅ or alternatively two substituents R₄ linked to 2 adjacent carbons of the phenyl form together a ring chosen from cycloalkyl, heterocyclyl, aryl and heteroaryl, optionally substituted with one or more R₄;

X₁ is —CH₂—; X₂ is independently chosen from the group consisting of O, and N(R₅), or alternatively, X₁ and X₂ form together a divalent group independently chosen from —N=C(R₅)— and —N(R₅)—C(R₅) (R₅)—, it being possible for the two substituents R₅ to be identical or different;

m has the value 0, 1, 2, 3, or 4; and

R₅ is independently chosen from non-bonding electron doublet, H, (C1-C12)alkyl, (C2-C12)alkenyl, (C2-C12)alkynyl, halo(C1-C12)alkyl, aryl(C1-C12)alkyl, heteroaryl(C1-C12)alkyl, heteroarylaryl(C1-C12) alkyl, aryl, heteroaryl and cycloalkyl, in which each R₅ is optionally substituted with at least one substituent chosen from OH, halogen, (C1-C4)alkyl, (C1-C4) alkoxy, aryl(C1-C4)alkyl, aryl, heteroaryl(C1-C4) alkyl, heteroaryl, —N(CH₃)₂, —NH₂, CONH₂,

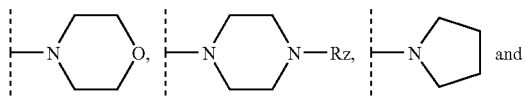

-continued

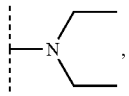

each of the Rz is independently chosen from the group consisting of H, COO(R₅), CONH(R₅), CON(R₅)₂, CO(R₅) and R₅, in which each R₅ is independently chosen from (C1-C4)alkyl, halo(C1-C4)alkyl, aryl (C1-C4)alkyl,and heteroaryl(C1-C4)alkyl, in which each R₅ is optionally substituted with one substituent chosen from OH, halogen, (C1-C4)alkyl, (C1-C4) alkoxy, aryl(C1-C4)alkyl, aryl, heteroaryl(C1-C4) alkyl and heteroaryl; or a pharmaceutically acceptable acid addition salt of such compound wherein heteroaryl is a monocyclic or polycyclic heteroaromatic substituent containing from 1 to 13 carbon atoms and from 1 to 4 heteroatoms selected from oxygen, sulphur, nitrogen and selenium, and heterocyclyl is a saturated or partially unsaturated cyclic hydrocarbon based substituent containing from 1 to 13 carbon atoms and from 1 to 4 heteroatoms selected from oxygen, sulphur, nitrogen and selenium.

28. The compound according to claim 1 wherein heteroaryl is pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo [b]thienyl; indazolyl; benzimidazolyl; azaindolyl; quinolyl; isoquinolyl; carbazolyl; and acridyl.

29. The compound according to claim 1 where heterocyclyl is a saturated or partially unsaturated hydrocarbon based substituent which is monoocyclic and contains 4 or 5 carbon atoms and 1 to 3 heteroatoms.

30. The compound according to claim 27 wherein heteroaryl is pyrrol-1-yl; pyrrol-2-yl; pyrrol-3-yl; furyl; thienyl; imidazolyl; oxazolyl; thiazolyl; isoxazolyl; isothiazolyl; 1,2, 4-triazolyl; oxadiazolyl; thiadiazolyl; tetrazolyl; pyridyl; pyrimidyl; pyrazinyl; 1,3,5-triazinyl;

indolyl; benzo[b]furyl; benzo[b]thienyl; indazolyl; benzimidazolyl; azaindolyl; quinolyl;

isoquinolyl; carbazolyl; and acridyl.

31. The compound according to claim 1 where heterocyclyl is a saturated or partially unsaturated hydrocarbon based substituent which is monoocyclic and contains 4 or 5 carbon atoms and 1 to 3 heteroatoms.

* * * * *